US012070022B2

(12) United States Patent
Fahrenkrug et al.

(10) Patent No.: US 12,070,022 B2
(45) Date of Patent: Aug. 27, 2024

(54) METHODS FOR MAKING GENETIC EDITS

(71) Applicant: Recombinetics, Inc., Eagan, MN (US)

(72) Inventors: Scott C. Fahrenkrug, Minneapolis, MN (US); Daniel F. Carlson, Woodbury, MN (US)

(73) Assignee: RECOMBINETICS, INC., Eagan, MN (US)

( * ) Notice: Subject to any disclaimer, the term of this patent is extended or adjusted under 35 U.S.C. 154(b) by 0 days.

(21) Appl. No.: 17/379,898

(22) Filed: Jul. 19, 2021

(65) Prior Publication Data

US 2022/0056482 A1    Feb. 24, 2022

Related U.S. Application Data

(60) Continuation of application No. 15/923,951, filed on Mar. 16, 2018, now abandoned, which is a division of application No. 14/698,561, filed on Apr. 28, 2015, now abandoned.

(60) Provisional application No. 61/985,327, filed on Apr. 28, 2014.

(51) Int. Cl.
| | | |
|---|---|---|
| C12N 15/63 | (2006.01) | |
| A01K 67/0275 | (2024.01) | |
| A01K 67/0276 | (2024.01) | |
| C12N 9/22 | (2006.01) | |
| C12N 15/79 | (2006.01) | |
| C12N 15/873 | (2010.01) | |
| C12N 15/90 | (2006.01) | |

(52) U.S. Cl.
CPC ...... *A01K 67/0276* (2013.01); *A01K 67/0275* (2013.01); *C12N 9/22* (2013.01); *C12N 15/873* (2013.01); *C12N 15/907* (2013.01); *A01K 2217/07* (2013.01); *A01K 2217/075* (2013.01); *A01K 2217/15* (2013.01); *A01K 2227/101* (2013.01); *A01K 2227/108* (2013.01); *A01K 2267/02* (2013.01)

(58) Field of Classification Search
CPC ........ C12N 15/63; C12N 15/85; C12N 15/86; C12N 15/902; C12N 2510/00; C12N 2310/20; C07H 21/02; C07H 21/04
See application file for complete search history.

(56) References Cited

U.S. PATENT DOCUMENTS

| | | |
|---|---|---|
| 4,873,191 A | 10/1989 | Wagner et al. |
| 6,548,741 B2 | 4/2003 | Desousa et al. |
| 6,613,752 B2 | 9/2003 | Kay et al. |
| 7,709,206 B2 | 5/2010 | Denise et al. |
| 8,106,255 B2 | 1/2012 | Carroll et al. |
| 8,309,791 B2 | 11/2012 | Fahrenkrug et al. |
| 8,518,701 B2 | 8/2013 | Fahrenkrug et al. |
| 8,685,737 B2 | 4/2014 | Serber et al. |
| 8,697,359 B1 | 4/2014 | Zhang |
| 8,697,851 B2 | 4/2014 | Frendewey et al. |
| 8,785,718 B2 | 7/2014 | Fahrenkrug et al. |
| 9,260,723 B2 | 2/2016 | Mali et al. |
| 9,840,713 B2 | 12/2017 | Zhang et al. |
| 2001/0016315 A1 | 8/2001 | Renaville et al. |
| 2005/0003542 A1 | 1/2005 | Kay et al. |
| 2005/0153317 A1 | 7/2005 | Denise et al. |
| 2010/0251395 A1 | 9/2010 | Harris et al. |
| 2011/0023140 A1 | 1/2011 | Bedell et al. |
| 2011/0023159 A1 | 1/2011 | Bedell et al. |
| 2011/0059160 A1 | 3/2011 | Essner et al. |
| 2011/0281306 A1 | 11/2011 | Kim et al. |
| 2011/0287545 A1 | 11/2011 | Cost et al. |
| 2012/0192298 A1 | 7/2012 | Weinstein et al. |
| 2012/0222143 A1 | 8/2012 | Fahrenkrug et al. |
| 2013/0117870 A1 | 5/2013 | Fahrenkrug et al. |
| 2013/0191931 A1 | 7/2013 | Grompe et al. |
| 2013/0212722 A1 | 8/2013 | West |
| 2013/0212725 A1 | 8/2013 | Kuehn et al. |
| 2014/0041066 A1 | 2/2014 | Carlson et al. |
| 2014/0068797 A1 | 3/2014 | Doudna et al. |
| 2014/0123330 A1 | 5/2014 | Carlson et al. |
| 2014/0134662 A1 | 5/2014 | Flavell et al. |
| 2014/0273037 A1 | 9/2014 | Wu |
| 2014/0273226 A1 | 9/2014 | Wu |
| 2014/0338007 A1 | 11/2014 | Fahrenkrug et al. |
| 2014/0351965 A1 | 11/2014 | Fahrenkrug et al. |
| 2014/0359795 A1 | 12/2014 | Fahrenkrug et al. |
| 2014/0359796 A1 | 12/2014 | Fahrenkrug et al. |
| 2015/0013025 A1 | 1/2015 | West |

(Continued)

FOREIGN PATENT DOCUMENTS

| | | |
|---|---|---|
| CN | 102905517 A | 1/2013 |
| CN | 103168101 A | 6/2013 |

(Continued)

OTHER PUBLICATIONS

Frendewey et al., 2015, US 20150159174 A1, effective filing date, Dec. 11, 2013.*
Dickinson et al., 2013 (Molecular Biology of the Cell, vol. 24, No. 24, Abstract No. 1073, p. 1-2).*
Cong et al., 2013 (Science, vol. 339, p. 819-823).*
U.S. Appl. No. 15/923,951 Office Action dated Apr. 2, 2019.
U.S. Appl. No. 15/923,951 Office Action dated Aug. 16, 2019.
U.S. Appl. No. 15/923,951 Office Action dated Jan. 27, 2020.
U.S. Appl. No. 15/923,951 Office Action dated Oct. 20, 2020.
U.S. Appl. No. 15/923,951 Restriction Requirement dated Nov. 15, 2018.
Bedell, et al. In vivo genome editing using a high-efficiency TALEN. Nature. 491.7422 (2012): 114-118.

(Continued)

*Primary Examiner* — Shin Lin Chen
(74) *Attorney, Agent, or Firm* — Wilson Sonsini Goodrich & Rosati

(57) ABSTRACT

The present disclosure relates to methods for making genetic edits in vitro in a non-human vertebrate cell or embryo at a plurality of target chromosomal DNA sites. Methods for making a non-human animal having multiplex genetic edits at a plurality of target chromosomal DNA sites and making a non-human vertebrate animal chimeric for host cells and donor cells are also considered.

13 Claims, 13 Drawing Sheets

Specification includes a Sequence Listing.

(56) References Cited

U.S. PATENT DOCUMENTS

| | | |
|---|---|---|
| 2015/0018604 A1 | 1/2015 | West et al. |
| 2015/0044192 A1 | 2/2015 | Liu et al. |
| 2015/0064149 A1 | 3/2015 | West et al. |
| 2015/0067898 A1 | 3/2015 | Fahrenkrug et al. |
| 2015/0140664 A1 | 5/2015 | Byrne et al. |
| 2015/0156996 A1 | 6/2015 | Fahrenkrug et al. |
| 2016/0024529 A1 | 1/2016 | Carstens |
| 2016/0029604 A1 | 2/2016 | Fahrenkrug et al. |
| 2016/0168592 A1 | 6/2016 | Church et al. |

FOREIGN PATENT DOCUMENTS

| | | |
|---|---|---|
| CN | 103228130 A | 7/2013 |
| CN | 103492578 A | 1/2014 |
| EP | 3138910 B1 | 9/2017 |
| JP | 2010539931 A | 12/2010 |
| JP | 2012510812 A | 5/2012 |
| WO | WO-2011072246 A2 | 6/2011 |
| WO | WO-2011133387 A1 | 10/2011 |
| WO | WO-2012012738 A1 | 1/2012 |
| WO | WO-2012149470 A1 | 11/2012 |
| WO | WO-2013176772 A1 | 11/2013 |
| WO | WO-2013192316 A1 | 12/2013 |
| WO | WO-2014066505 A1 | 5/2014 |
| WO | WO-2014099744 A1 | 6/2014 |
| WO | WO-2014143381 A1 | 9/2014 |
| WO | WO-2014161821 A1 | 10/2014 |
| WO | WO-2014197748 A2 | 12/2014 |
| WO | WO-2015006290 A1 | 1/2015 |
| WO | WO-2015052231 A2 | 4/2015 |
| WO | WO-2015123339 A1 | 8/2015 |

OTHER PUBLICATIONS

Branda et al., Talking About a Revolution: The Impact of Site-Specific Recombinases on Genetic Analyses in Mice. Developmental Cell, 6.1 (Jan. 2004): 7-28.
Carlson et al., "Adding and Subtracting Livestock Genes With Transposons and Nucleases", Transgenic Research, 2 Pages (Nov. 15, 2011).
Carlson et al., Editing Livestock Genomes With Site-Specific Nucleases. Reproduction, Fertility and Development, 26 (Dec. 5, 2013): 74-82.
Carlson et al., Efficient TALEN-Mediated Gene Knockout in Livestock. Proceeding of the National Academy of Sciences, 109.43 (Oct. 23, 2012): 17382-17387.
Carlson et al., Strategies for Selection Marker-Free Swine Transgenesis Using the Sleeping Beauty Transposon System. Transgenic Research, Jan. 9, 2011, 13 Pages.
Carlson et al., Targeting DNA with Fingers and TALENs. Molecular Therapy-Nucleic Acid, 1 (2012): 1-5.
CARLSON. Production of GE livestock using TALENs: an under-the-hood look at TALEN-stimulated HDR. Transgenic Res 23(1):189 (2014). Abstract from the UC Davis Transgenic Animal Research Conference IX, Aug. 11-15, 2013. DOI 10.1007/s11248-013-9761-0.
Cibelli, et al. Cloned transgenic calves produced from nonquiescent fetal fibroblasts. Science, 280 (1998):1256-1258.
Cogoni et al., Gene Silencing in Neurospora crassa Requires a Protein Homologous to RNA-Dependent RNA Polymerase. Nature 399 (May 13, 1999): 166-169.
Cogoni et al., Transgene Silencing of the al-1 Gene in Vegetative Cells of Neurospora in Mediated by a Cytoplasmic Effector and Does Not Depend on DNA-DNA interactions or DNA Methylation. The EMBO Journal. 15.12 (1996): 3153-3163.
Cong et al. Multiplex genome engineering using CRISPR/Cas systems. Science 339(6121):819-23 (2013).
Dicarlo, et al. Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.
Dupuy et al., Mammalian Germ-Line Transgenesis by Transposition Proceeding of the National Academy of Sciences, 99.7 (2002): 4495-4499.
EP15723593.8 Communication pursuant to Article 94(3) EPC dated Sep. 21, 2020.
EP15723593.8 Communication under pursuant to Rule 164(2)(b) and Article 94(3) EPC dated Sep. 19, 2018.
EP15723593.8 Communication under Rule 164(2)(a) EPC dated Jun. 6, 2018.
Feng et al., A Robust TAKENs System For Hightly Efficient Mammalian Genome Editing. Scientific Reports, (Jan. 2014).
Fire et al. Potent and specific genetic interference by double-stranded RNA in Caenorhabditis elegans. Nature 391 (1998): 806-811.
Grobet et al., A Deletion in the Bovine Myostatin Gene Causes the Double-Muscled Phenotype in Cattle, Nature Genetics, 17 (Sep. 17, 1997), p. 71.
Guatelli et al. Isothermal, in vitro amplification of nucleic acids by a multienzyme reaction modeled after retroviral replication. PNAS USA 87(5):1874-1878 (1990).
Hauschild et al., Efficient Generation of a Biallelic Knockout in Pigs Using Zinc-Fingers Nucleases. Proceedings of the National Academy of Sciences, 108 (2011): 12013-12017.
Hruscha et al. Efficient CRISPR/Cas9 genome editing with low off-target effects in zebrafish. Development. Dec. 2013;140(24):4982-7. doi: 10.1242/dev.099085. Epub Nov. 20, 2013.
Hruscha et al., Efficient CRISPR/Cas9 Genome Editing With Low Off-Target Effects in Zebrafish. Research Report Techniques and Resources, (Sep. 25, 2013): 7 Pages.
Hwang et al., Heritable and Precise Zebrafish Genome Editing Using a CRISPR-Cas System. PLoS One, 8.7 (Jul. 2013): 9 Pages.
Jao et al., Efficient Multiplex Biallelic Zebrafish Genome Editing Using a CRISPR Nuclease System. Proceedings of the National Academy of Sciences of the United States of America, 110.34 (Aug. 2013): 13904-13909.
Joung et al. TALENs: a widely applicable technology for targeted genome editing. Nat Rev Mol Cell Biol 14.1 (2013): 49-55.
Kabadi et al. Multiplex CRISPR/Cas9-based genome engineering from a single lentiviral vector. Nucleic Acids Res 42:e147 (2014).
Kambadur et al., Mutations in Myostatin (GDF8) in Double-Muscled Belgian Blue and Piedmontese Cattle. Genome Res., 7 (1997): 910-915.
Kawakami, ToI2: a versatile gene transfer vector in vertebrates. Genome Biology, 8(suppl 1) article s7, S7.1-S7.10 (2007).
Kennerdell et al., Use of dsRNA-Mediated Genetic Interference to Demonstrate that frizzled and frizzled 2 Act in the Wingless Pathway. Cell, 95 (Dec. 23, 1998): 1017-1026.
Kiwaki et al., Correction of Ornithine Transcarbamylase Deficiency in Adult spfash Mice and in OTC-Deficient Human Hepatocytes with Recombinant Adenoviruses Bearing the CAG Promoter. Human Gene Therapy, 7 (May 1, 1996): 821-830.
Kubota et al., Serial Bull Clonging By Somatic Cell Nuclear Transfer. Nature Biotechnology, 22.6 (Jun. 2004): 693-694.
Kuroiwa et al., Sequential Targeting of the Genes Encoding immunoglobulin-u and Prion Protein in Cattle. Nature Genetics, 36.7 (Jul. 2004): 775-780.
Lavitrano et al., Efficient Production by Sperm-Mediated Gene Transfer of Human Decay Accelerating Factor (hDAF) Transgenic Pigs for Xenotransplantation, Proceedings of the National Academy of Science, 99.22 (Oct. 29, 2002): 14230-14235.
Lavitrano et al., Sperm-Mediated Gene Transfer, Reproduction, Fertility and Development, 18 (2006): 19-23.
Li et al. In vivo genome editing restores haemostasis in a mouse model of haemophilia. Nature 475.7355 (2011): 217-221, plus Supplemental Material.
Li P, Biallelic knockout of the α-1,3 galactosyltransferase gene in porcine liver-derived cells using zinc finger nucleases. J Surg Res. 181.1 (May 1, 2013): e39-45. doi: 10.1016/j.jss.2012.06.035. PubMed PMID: 22795272.
Lillico et al., Live Pigs Produced From Genome Edited Zygotes, Scientific Reports 3:2847 (Oct. 10, 2013): 4 pages.

(56) References Cited

OTHER PUBLICATIONS

Lino et al. Delivering CRISPR: a review of the challenges and approaches. Drug Delivery 25(1):1234-1257 (2018). Published online May 25, 2018.
Lo. Transformation by iontophoretic microinjection of DNA: multiple integrations without tandem insertions. Mol. Cell. Biol., 3.10 (1983): 1803-1814.
Lu et al., TALEN-Mediated Gene Mutagenesis in Rhesus and Cynomolgus Monkeys. Cell Stem Cell, 14.3 (Mar. 6, 2014): 323-328.
Lutz et al., Double knockout pigs deficient in N-glycolylneuraminic acid and galactose α-1,3-galactose reduce the humoral barrier to xenotransplantation. Xenotransplantation. 20.1 (Jan.-Feb. 2013): 27-35. doi: 10.1111/xen.12019. PubMed PMID: 23384142.
Ma et al., CRISPR/Cas9 Mediated Multiplex Genome Editing and Heritable Mutagenesis of BmKu70 in Bombyx-mori. Scientific Reports 4:4489 (Mar. 27, 2014). 6 pages.
Ma et al., High Efficiency In Vivo Genome Engineering with a Simplified 15-RVD GoldyTALEN Design. PLOS One, 8.5 (May 2013): 1-8.
Ma et al. Heritable multiplex genetic engineering in rats using CRISPR/Cas9. PLOS One 9(3):e89413 (Mar. 5, 2014). 8 pages. doi: 10.1371/journal.pone.0089413.
Mali et al., RNA-Guided Human Genome Engineering Via Cas9. Science, 339 (Feb. 15, 2013): 823-826.
Mashimo et al., Generation of gene-modified cynomolgus monkey via Cas9/RNA-mediated gene targeting in one-cell embryos. CELL, 156 (2014): 836-843.
Mashimo. Gene targeting technologies in rats: Zinc finger nucleases, transcription activator-like effector nucleases, and clustered regularly interspaced short palindromic repeats. Develop Growth Differ 56:46-52 (2014). doi: 10.1111/dgd.12110.
Matsunari et al. Blastocyst complementation generates exogenic pancreas in vivo in apancreatic cloned pigs. PNAS USA 110 (2013): 4557-4562.
Miskey et al., The Ancient Mariner Sails Again: Transposition of the Human Hsmar1 Element by a Reconstructed Transposase and Activities of the SETMAR Protein on Transposon Ends. Molecular and Cellular Biology, 27.12 (Jun. 2007): 4589-4600.
Miskey et al., The Frog Prince: a reconstructed transposon from Rana pipiens with high transpositional activity in vertebrate cells. Nucleic Acids Res. 31.23 (2003): 6873-6881.
Misquitta et al., Targeted Disruption of Gene Function in *Drosophila* by RNA Interference (RNA-i): A Role for Nautilus in Embryonic Somatic Muscle Formation. Proceedings of the National Academy of Science, 96 (Feb. 1999): 1451-1456.
Moriarity, et al. Simple and efficient methods for enrichment and isolation of endonuclease modified cells. PLoS One. 9.5 (May 5, 2014): e96114. doi: 10.1371/journal.pone.0096114. eCollection 2014.
Nagashima et al., Sex Differentiation and Germ Cell Production in Chimeric Pigs Produced by Inner Cell Mass Injection Into Blastocysts. Biology of Reproduction, 70 (2004): 702-707. Published online before print Nov. 12, 2003.
Ni et al., Efficient Gene Knockout in Goats Using CRISPRICas9 System. PLOS One, 9.9 (Sep. 2014): 1-7.
Niu, et al. Generation of Gene-Modified Cynomolgus Monkey via Cas9/RNA-Mediated Gene Targeting in One-Cell Embryos. Cell. Feb. 13, 2014;156(4):836-43. doi: 10.1016/j.cell.2014.01.027. Epub Jan. 30, 2014.
Orban et al., Tissue and Site-Specific DNA Recombination in Transgenic Mice. Proceedings of the National Academy of Science, 89 (Aug. 1992): 6861-6865.
Pavlopoulos et al., The DNA transposon Minos as a tool for transgenesis and functional genomic analysis in vertebrates and invertebrates. Genome biology 8.1 (suppl 1) article S2 (2007): S2.1-S2.7.
PCT/US2015/027995 International Search Report and Written Opinion dated Sep. 28, 2015.
PCT/US2015/027995 International Preliminary Report on Patentability dated Nov. 1, 2016.
Proudfoot et al., Genome Edited Sheep and Cattle, Transgenic Research, 24 (Sep. 10, 2015): 147-153.
Reyes, et al. Creating class I MHC-null pigs using guide RNA and the Cas9 endonuclease. J Immunol. Dec. 1, 2014;193(11):5751-7. doi: 10.4049/jimmunol.1402059. Epub Oct. 22, 2014.
Romano et al., Quelling: transient inactivation of gene expression in Neurospora crassa by transformation with homologous sequences. Mol. Microbiol., 6.22 (1992): 3343-3353.
SCHNEITER. Genetics, Molecular and Cell Biology of Yeast. Université de Fribourg Suisse (Jan. 2004). 86 pages.
Tan et al., Efficient Nonmeiotic Allele Introgression in Livestock Using Custom Endonucleases. Proceeding of the National Academy of Sciences, (Aug. 13, 2013): 6 pages.
Tan et al., Efficient Non-Meiotic Allele Introgression in Livestock Using TAL Effector Nucleases and The CRISPR- cas9 System. Transgenic Research, 23 (2014): 187-210. Abstract Only.
Tan et al., Gene Targeting of the Swine Myostatin Gene Using rAAV and TALENs. Transgenic Research 21 (2012): 901-925, p. 917. Abstract from the UC Davis Transgenic Animal Research Conference VIII, Aug. 7-10, 2011.
Tan, et al. Precision editing of large animal genomes. Adv Genet. 2012;80:37-97. doi: 10.1016/B978-0-12-404742-6.00002-8.
Tan et al. Efficient nonmeiotic allele introgression in livestock using custom endonucleases. Proceeding of the National Academy of Sciences110(41):16526-16531 (Oct. 8, 2013).
Tan, Genome Engineering in Large Animals for Agricultural and Biomedical Applications, A Dissertation Submitted to the Faculty of University of Minnesota (Aug. 2013).
Thompson, et al. Germ line transmission and expression of a corrected HPRT gene produced by gene targeting in embryonic stem cells. Cell, 56 (1989):313-321.
U.S. Appl. No. 14/698,561 Non-Final Office Action dated Sep. 19, 2017.
U.S. Appl. No. 14/698,561 Restriction Requirement dated Feb. 23, 2017.
Van Der Putten, et al. Efficient insertion of genes into the mouse germ line via retroviral vectors. Proc. Natl. Acad. Sci. USA, 82 (1985): 6148-1652.
Visscher et al., Breeding Objectives for Pasture Based Dairy Production Systems. Livestock Production Science, 40 (1994): 123-137.
Wakayama, et al. Full-term development of mice from enucleated oocytes injected with cumulus cell nuclei. Nature, 394 (1998): 369-374.
Wang et al. One-step generation of mice carrying mutations in multiple genes by CRISPR/Cas-mediated genome engineering. Cell 153:910-918 (2013).
WEISS. Hot prospect for new gene amplifier. Science, 254 (1991): 1292-1293.
Whitworth, et al. Use of the CRISPR/Cas9 system to produce genetically engineered pigs from in vitro-derived oocytes and embryos. Biol Reprod. Sep. 2014;91(3):78, 1-13. doi: 10.1095/biolreprod.114.121723. Epub Aug. 6, 2014.
Wilmut, et al. Viable offspring derived from fetal and adult mammalian cells. Nature, 385 (1997): 810-813.
Xin et al., Highly Efficient Generation of GGTA1 Biallelic Knockout Inbred Mini-Pigs With TALENs. PLOS One, 8.12 (Dec. 2013): 10 Pages.
Xu et al., CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice, Hum Gene Ther., 12 (2001): 563-573.
Yan et al., Generation of Multi-Gene Knockout Rabbits Using The Cas9/gRNA System. Cell Regeneration, 3.12 (2014): 1-11.
Yang et al., Cattle Call For Gene Targeting. Nature, 36.7 (Jul. 2004): 671-672.
Zhang, F. et al. CRISPR/Cas9 for genome editing: Progress, Implications and challenges. Human Molecular Genetics 23(R1):R40-R46 (Mar. 20, 2014).
Zheng et al., Precise Gene Deletion and Replacement Using The CRISPR1Cas9 System in Human Cells. BioTechniques, 57 (Sep. 2014): 115-124.

(56) References Cited

OTHER PUBLICATIONS

Zhou et al. One-step generation of different immunodeficient mice with multiple gene modifications by CRISPR/Cas9 mediated genome engineering. International Journal of Biochemistry and Cell Biology 46:49-55 (Jan. 2014). DOI: https://doi.org/10.1016/j.biocel.2013.10.010.

Pan et al. Chimeric mice production by PLCζ-deletant JM8 cells. Journal of Agricultural University of Hebei, vol. 36, No. 4, pp. 105-109 (Jul. 2013). With English abstract.

Bak et al. Multiplexed genetic engineering of human hematopoietic stem and progenitor cells using CRISPR/Cas9 and AAV6. eLife 2017;6:e27873. 19 pages.

Buehr et al., Capture of authentic embryonic stem cells from rat blastocysts. Cell 135:1287-1298 (2008).

Dickinson et al. Engineering the Caenorhabditis elegans Genome Using Cas9-Triggered Homologous Recombination. Nat Methods. Oct. 2013 ; 10(10): 1028-1034.

Kadandale et al. Germline transformation of Caenorhabditis elegans by injection. Methods Mol Biol. 2009 ; 518: 123-133.

Lee et al. Production of large, defined genome modifications in rats by targeting rat embryonic stem cells. Stem Cell Reports, vol. 18, pp. 394-409 (Jan. 10, 2023).

\* cited by examiner

GENERATION OF HOMOZYGOUS CATTLE EDITED AT MULTIPLE ALLELES a- probability of genotype is 0.001 percent. Binomial prediction for independent derivation of this genotype is K ≥ 2; p<2.55 E -7 or 0.000026%.

a- Top line probability of success. = 0.001 (0.1%). K ≥ 1; p =0.17; 17%.
b- Second line: probability of success 0.00002. K ≥ 1; p =0.0019; or 0.19%
c- Fourth line: probability of success 0.0025. K ≥ 1; p =0.38; or 38 percent.

METHODS FOR MAKING GENETIC EDITS

CROSS REFERENCE TO RELATED APPLICATIONS

This application is a Continuation of U.S. patent application Ser. No. 15/923,951 filed on Mar. 16, 2018; which is a Divisional of U.S. patent application Ser. No. 14/698,561 filed on Apr. 28, 2015; which claims priority to U.S. Provisional Application No. 61/985,327, filed Apr. 28, 2014, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 19, 2021, is named 1000_716_301_SL_ST25.txt and is 14,323 bytes in size.

TECHNICAL FIELD

The technical field relates to gene editing at multiple sites, multiple gene edits in vertebrate cells, and uses thereof.

BACKGROUND

Genetic modifications to cells, and to animals made from such cells, are useful for changing the expression of genes. The field of genetic engineering is very active.

SUMMARY OF THE INVENTION

It would be very useful to make large vertebrate animals that, in a single generation, have multiple changes to their genetic code. As disclosed herein, it is possible to do so by simultaneously editing multiple genes in a cell or embryo. Multiple genes can be targeted for editing using targeted nucleases and homology directed repair (HDR) templates in vertebrate cells or embryos. These cells or embryos can be used for research or to make whole animals. Multiple edits can be made in a single generation that could not be made otherwise, for instance, by breeding or genetic engineering changes made in seriatim

DETAILED DESCRIPTION

Processes for multiplex gene edits are described. Multiple genes can be modified in a cell or embryo that may be used for research or to make whole animals. Other embodiments involve the complementation of cell or organ loss by selective depopulation of host niches. These inventions provide for rapid creation of animals to serve as models, food, and as sources of cellular and acellular products for industry and medicine.

Figure 1A:
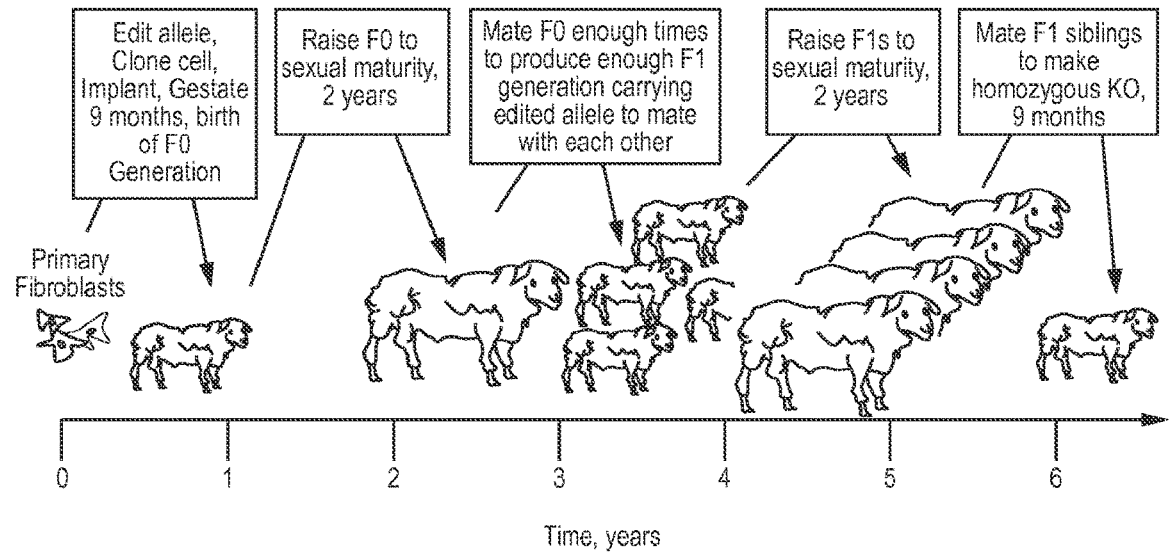
FIG. 1A depicts a process for making animals homozygous for two knockouts using single edits.
Figure 1B:
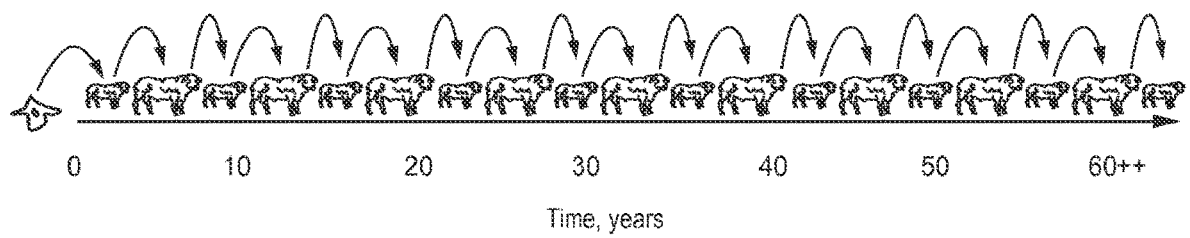
FIG. 1B depicts a hypothetical process of making animals with multiple edits by making of a single edit at a time.

FIG. 1A has a timeline that illustrates why it takes several years using single edits to make livestock that have only two edited alleles, with the time being about six years for cattle. Edited, in this context, refers to choosing gene and altering it. First, a gene of interest has to be edited, for instance knocked out (KO), in cultured somatic cells that are cloned to create a heterozygous calf with a targeted KO. The heterozygotes would be raised to maturity for breeding, about 2 years old for cattle, to generate first-generation (F1) male and female heterozygous calves, which would be bred with each other to generate a homozygous knockout calf (F2). Generating homozygotes with respect to multiple targeted mutations using a conventional approach in cattle would be impractical. The number of required years and the number of required animals to make further edits increases in an approximately exponential fashion, depending on the particular scheme that is used, as illustrated in FIG. 1B. Among the vertebrates, even those animals that have larger numbers of offspring per generation and have shorter gestational times than cattle nonetheless would require overly long times to achieve multiple edits. Swine, for example, have a larger number of offspring per mating and a gestational time that is roughly half that of cattle but the time to make multiple edits can require many years. Moreover, schemes that minimize time with aggressive inbreeding may not be reasonably possible for multiple edits. Also, serial cloning is undesirable from a process and an outcome standpoint, especially if the animals are to be useful as livestock or laboratory models.

Figure 2:
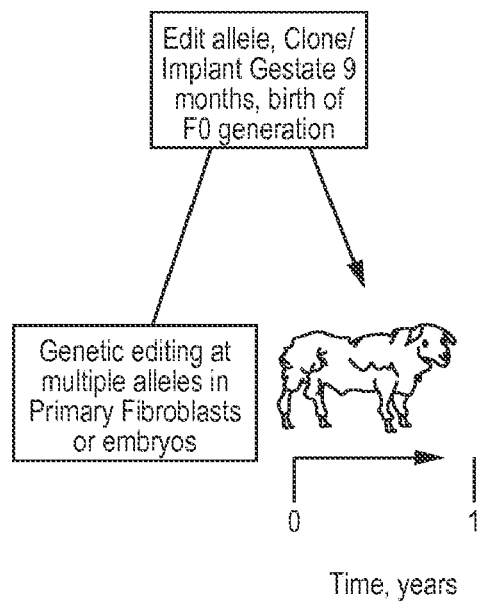
FIG. 2 depicts multiplex gene edits used to establish founders at generation F0

An opportunity presented by the invention is illustrated in FIG. 2, which shows multiple edits being made in a first-generation animal (F0). Embryos are prepared directly or by cloning with two or more edits independently chosen to be heterozygotes or homozygotes and placed in surrogate females to gestate. The resultant animals are F0 generation founders. A plurality of embryos may be prepared and placed in one or more surrogates to produce progeny of both genders, or well-known techniques of embryo-splitting may be used to make a plurality of clonal embryos. Livestock such as pigs that typically produce a litter with both genders may be crossed and propagated.

Multiple alleles can be disrupted or otherwise edited as described herein in a cell or embryo using targeted endonucleases and homology directed repair (HDR). An embodiment is a method of making genetic edits in a vertebrate cell or embryo at a plurality of target chromosomal DNA sites comprising introducing into a vertebrate cell or embryo: a first targeted endonuclease directed to a first target chromosomal DNA site and a first homology directed repair (HDR) template homologous to the first target site sequence; and a second targeted endonuclease directed to a second target chromosomal DNA site and a second HDR template homologous to the second target site sequence, with the first HDR template sequence replacing the native chromosomal DNA sequence at the first target site and the second HDR template sequence replacing the native chromosomal DNA sequence at the second target site sequence.

It was an unexpected and surprising, and not predictable, result to learn that multiple edits such as knockouts or replacements could be obtained. One theorized mechanism is that there are a minority of cells that are receptive to multiple edits because they are at a particular stage in the cell cycle. When exposed to endonucleases and HDR templates, they respond readily. A related theory of operation is that the HDR templating process lends itself to multiple substitutions because activation of cellular repair machinery for one targeted site favors repair, or HDR templating, at other sites as well. HDR has historically been a low efficiency process so that multiple HDR edits were apparently not attempted, observed, or recognized.

Results herein show that too much or too little endonuclease and/or HDR template can have a negative effect, which may have confounded prior research in this area. In fact, the inventors have observed that targeted endonucleases can be designed and made correctly but nonetheless fail because they are too efficient. Further, the population of successfully modified cells often does not improve over time. Artisans modifying cells normally look for longevity of the cell and modification as an indicator of stability and health for successful cloning or other uses. But that expectation has often not been helpful in the multiplexing processes herein. Moreover, the inventors have observed that HR introgression efficiencies are variable in the multiplex approach as compared to a single-locus introgression. Some loci were very sensitive but others had large drops in efficiency. There is apparently interference between the endonucleases but the net effect cannot be explained simply, for instance by positing that the endonucleases are competing for common resource.

There are various well-known techniques to insert many genes randomly or imprecisely into a plurality of locations in chromosomal DNA, or to make many random edits that disrupt a plurality of genes. As is evident, random or imprecise processes are not going to assist the scientist that needs to edit a plurality of specifically targeted genes to achieve an effect. Accordingly, HDR processes taught herein may be readily distinguished by the edits, and resultant organisms, being made only at the intended target sites. One difference is that the inventive HDR editing embodiments can be performed free of insertion of extra gene copies and/or free of disruption of genes other than those targeted by the endonucleases. And the specific edits are made at one location because the HDR template sequence is not copied into sites without appropriate homology. Embodiments include organisms and processes wherein an exogenous allele is copied into chromosomal DNA only at the site of its cognate allele.

An advantage of HDR-based editing is that the edits can be chosen. In contrast, other attempts, by non-homologous end joining (NHEJ) processes, can make indels at multiple positions such that the indels cancel each other out without making a frame shift. This problem becomes significant when multiplexing is involved. But successful use of HDR provides that the edits can be made to ensure that, if desired, the target gene has an intended frame shift. Moreover, allelic replacement requires HDR and cannot be accomplished by NHEJ, vector-driven insertion of nucleic acids, transposon insertions, and the like. Moreover, choosing organism that are free of unwanted edits further increases the degree of difficulty.

It is generally believed, however, that multiplex edits as described herein have not been previously achieved at targeted sites in cells or animals relevant to livestock or large vertebrates. It is well known that cloning animals from high-passage cells creates animals with so much genetic damage that they are not useful as F0 founders of laboratory models or livestock.

And gene editing is a stochastic process; as a result, the field has traditionally emphasized various screening techniques to identify the few percent of cells that have successfully been edited. Since it is a stochastic process, the difficulty of making a plurality of edits can be expected by the artisan to increase in an exponential fashion as the number of intended edits increases.

An embodiment of the invention provides processes for creating multiple targeted gene knockouts or other edits in a single cell or embryo, a process referred to herein as multiplex gene knockouts or editing. The term targeted gene refers to a site of chromosomal DNA that is selected for endonuclease attack by design of the endonuclease system, e.g., a TALENs or CRISPR. The term knockout, inactivated, and disrupted are used interchangeably herein to mean that the targeted site is changed so that the gene expression product is eliminated or greatly reduced so that the gene's expression no longer has a significant impact on the animal as a whole. These terms are sometimes used elsewhere to refer to observably reducing the role of a gene without essentially eliminating its role.

Gene editing, as that term is used herein, refers to choosing a gene and altering it. Random insertions, gene trapping, and the like are not gene editing. Examples of gene edits are, at targeted sites, gene knockouts, adding nucleic acids, removing nucleic acids, elimination of all function, introgression of an allele, a hypermorphic alteration, a hypomorphic alteration, and a replacement of one or more alleles.

A replacement of an allele refers to a non-meiotic process of copying an exogenous allele over an endogenous allele. The term replacement of an allele means the change is made from the native allele to the exogenous allele without indels or other changes except for in some cases degenerate substitutions. The term degenerate substitution means that a base in a codon is changed to another base without changing the amino acid that is coded. The degenerate substitution may be chosen to be in an exon or in an intron. One use for a degenerate substitution is to create a restriction site for easy testing of a presence of the introgressed sequence. The endogenous allele is also referred to herein as the native allele. The term gene is broad and refers to chromosomal DNA that is expressed to make a functional product. Genes have alleles. Genotypes are homozygous if there are two identical alleles at a particular locus and as heterozygous if the two alleles differ. Alleles are alternative forms of a gene (one member of a pair) that are located at a specific position on a specific chromosome. Alleles determine distinct traits. Alleles have basepair (bp) differences at specific positions in their DNA sequences (distinguishing positions or bp) that give rise to the distinct trait and distinguish them from each another, these distinguishing positions serve as allelic markers. Alleles are commonly described, and are described herein, as being identical if they have the same bases at distinguishing positions; animals naturally have certain variations at other bp in other positions. Artisans routinely accommodate natural variations when comparing alleles. The term exactly identical is used herein to mean absolutely no bp differences or indels in a DNA alignment.

A similar test for allelic identity is to align the chromosomal DNA in the altered organism with the chromosomal DNA of the exogenous allele as it is recognized in nature. The exogenous allele will have one or more allelic markers. The DNA alignment upstream and downstream of the markers will be identical for a certain distance. Depending on the desired test, this distance may be from, e.g., 10 to 4000 bp. While an HDR template can be expected to create a sequence that has exactly identical, the bases on either side of the templated area will, of course, have some natural variation. Artisans routinely distinguish alleles despite the presence of natural variations. Artisans will immediately appreciate that all ranges and values between the explicitly stated bounds are contemplated, with any of the following distances being available as an upper or lower limit: 15, 25, 50, 100, 200, 300, 400, 500, 600, 800, 1000, 1200, 1400, 1600, 1800, 2000, 4000.

Artisans are also able to distinguish gene edits to an allele that are a result of gene editing as opposed to sexual reproduction. It is trivial when the allele is from another species that cannot sexually reproduce to mix alleles. And many edits are simply not found in nature. Edits can be also be readily distinguished when alleles are migrated from one breed to the next, even when a replacement is made that exactly duplicates an allele naturally found in another breed. Alleles are stably located on DNA most of the time. But meiosis during gamete formation causes male and female DNAs to occasionally swap alleles, an event called a crossover. Crossover frequencies and genetic maps have been extensively studied and developed. In the case of livestock, the pedigree of an animal can be traced in great detail for many generations. In genetics, a centimorgan (cM, also called a map unit ($\mu$)) is a unit that measures genetic linkage. It is defined as the distance between chromosome positions (loci or markers of loci) for which the expected average number of intervening chromosomal crossovers in a single generation is 0.01. Genes that are close to each other have a lower chance of crossing over compared to genes that are distant from each other on the chromosome. Crossing over is a very rare event when two genes are right next to each other on the chromosome. Crossing over of a single allele relative to its two neighboring alleles is so improbable that such an event must be the product of genetic engineering. Even in the case where animals of the same breeds are involved, natural versus engineered allele replacement can be readily determined when the parents are known. And parentage can be determined with a high degree of accuracy by genotyping potential parents. Parent determination is routine in herds and humans.

Embodiments include multiplex gene editing methods that are simultaneous. The term simultaneous is in contrast to a hypothetical process of treating cells multiple times to achieve multiple edits, as in serial knockouts or serial cloning or intervening cycles of animal breeding. Simultaneous means being present at a useful concentration at the same time, for instance multiple targeted endonucleases being present. The processes can be applied to zygotes and embryos to make organisms wherein all cells or essentially all cells have edited alleles or knockouts. Essentially all cells, in the context of a knockout for instance, refers to knocking the gene out of so many cells that the gene is, for practical purposes, absent because its gene products are ineffective for the organism's function. The processes modify cells, and cells in embryos, over a minimal number cell divisions, preferably about zero to about two divisions. Embodiments include a quick process or a process that takes place over various times or numbers of cell divisions is contemplated, for instance: from 0 to 20 replications (cell divisions). Artisans will immediately appreciate that all values and ranges within the expressly stated limits are contemplated, e.g., about 0 to about 2 replications, about 0 to about 3 replications, no more than about 4 replications, from about 0 to about 10 replications, 10-17; less than about 7 days, less than about 1, about 2, about 3, about 4, about 5, or about 6 days, from about 0.5 to about 18 days, and the like. The term low-passage refers to primary cells that have undergone no more than about 20 replications.

Elsewhere, the inventors have shown that, in a single embryo, maternal, paternal or both alleles can be edited in bovine and porcine embryos, and that template editing of both alleles can therefore occur using HDR in the embryo. These edits were made at the same locus. Specifically, introgression from sister chromatids was detected. Carlson et al., PNAS 43(109):17382-17387, 2012.

Figure 3:
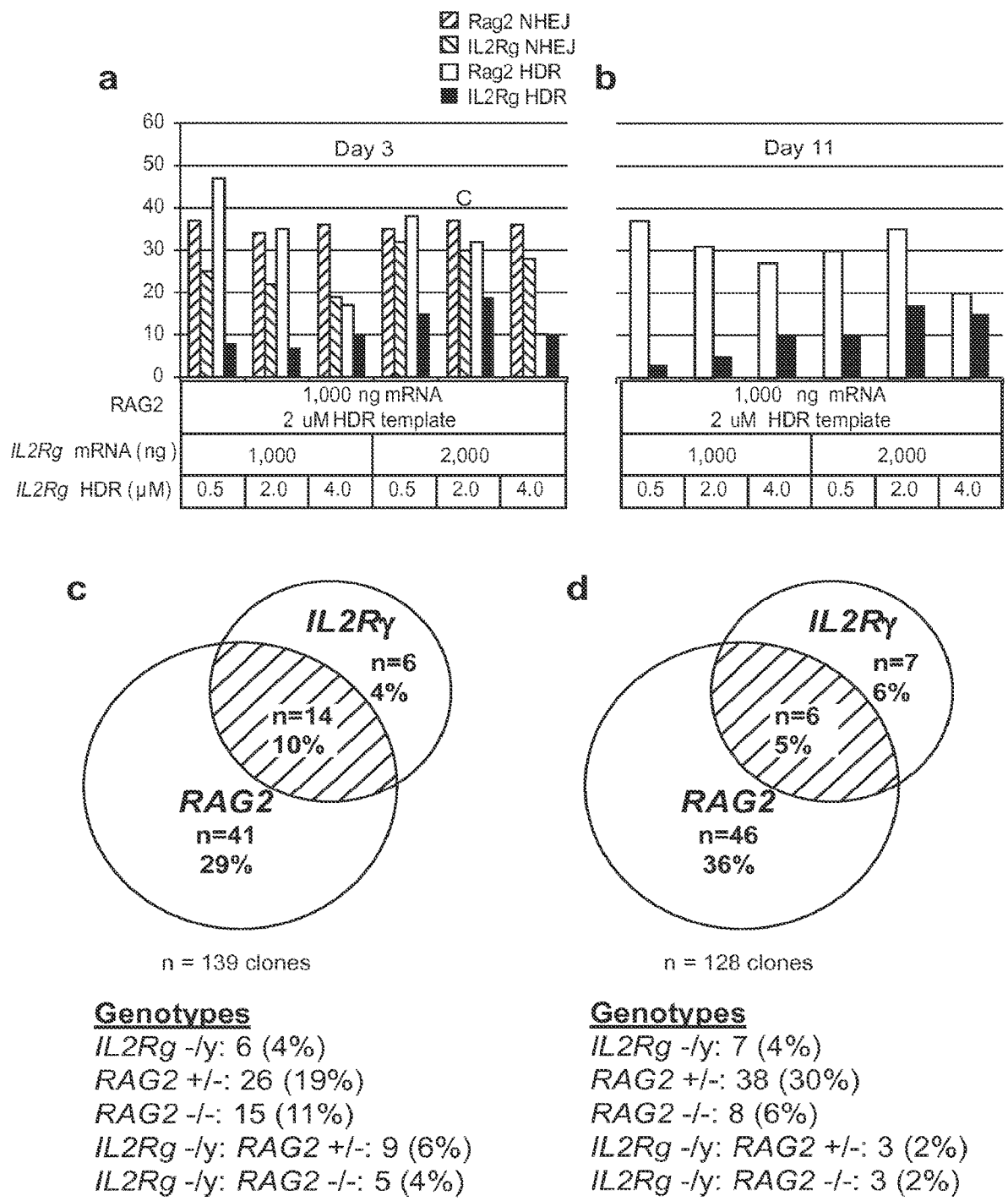
FIG. 3 Multiplex gene editing of swine RAG2 and IL2Rγ. Panel a) Surveyor and RFLP analysis to determine the efficiency of non-homologous end joining (NHEJ) and homology depended repair HDR on cell populations 3 days post transfection. Panel b) RFLP analysis for homology dependent repair on cell populations 11 days post transfection. Panel c) Percentage of colonies positive for HDR at IL2Rγ, RAG2 or both. Cells were plated from the population indicated by a "C" in panel a. Panel d) Colony analysis from cells transfected with TALEN mRNA quantities of 2 and 1 μg for IL2Ry and RAG2 and HDR template at 1 μM for each. Distribution of colony genotypes is shown below.

Example 1, see FIG. 3, describes experiments that attempted, successfully, to use HDR editing to knockout two genes at once and, further, to be able to select cells that are homozygous for both knockouts or heterozygous for each knockout. The term select is used to refer to the ability to identify and isolate the cells for further use; there were no expressible reporter genes anywhere in the process, which is a highly significant advantage that distinguishes this process from many other approaches. Cells were treated to introduce a first and a second targeted endonuclease (each being a TALENs pair) directed to, respectively, a first gene (Recombination Activating Gene 2, RAG2) and a second gene target (Interleukin Receptor 2, gamma, IL2Rg or ILR2γ). The TALENs had to be designed to target intended sites and made in adequate amounts. The treatment of the cells took less than five minutes. Electroporation was used but there are many other suitable protein or DNA introducing-processes described herein. The cells were then cultured so that they formed individual colonies of cells that each descended from a single treated cell. Cells from the various colonies were tested after 3 days or 11 days. The rate of knockout of RAG2 was about six times higher than the rate of knockout of IL2Rg; apparently some genes are more difficult to knockout than others. The efficiency of knocking out both genes was high and cells heterozygous or homozygous for both knockouts were successfully identified. Significantly, dosage of TALEN mRNA and HDR template had specific and non-specific effects. An increase in TALEN mRNA for IL2Rg led to an increase in both NHEJ and HDR for IL2Rg while NHEJ levels for RAG2 were unchanged. An increase in IL2Rg HDR template reduced HDR at the RAG2 locus suggesting a nonspecific inhibition of homology directed repair by escalation of the concentration of oligonucleotide. This dose sensitivity, particularly at these low doses, has possibly lead others away from pursuit of multiplex processes. Cells from Example 1 have been cloned and, at the time of filing, two animals are pregnant with embryos derived from the same.

Figure 4:
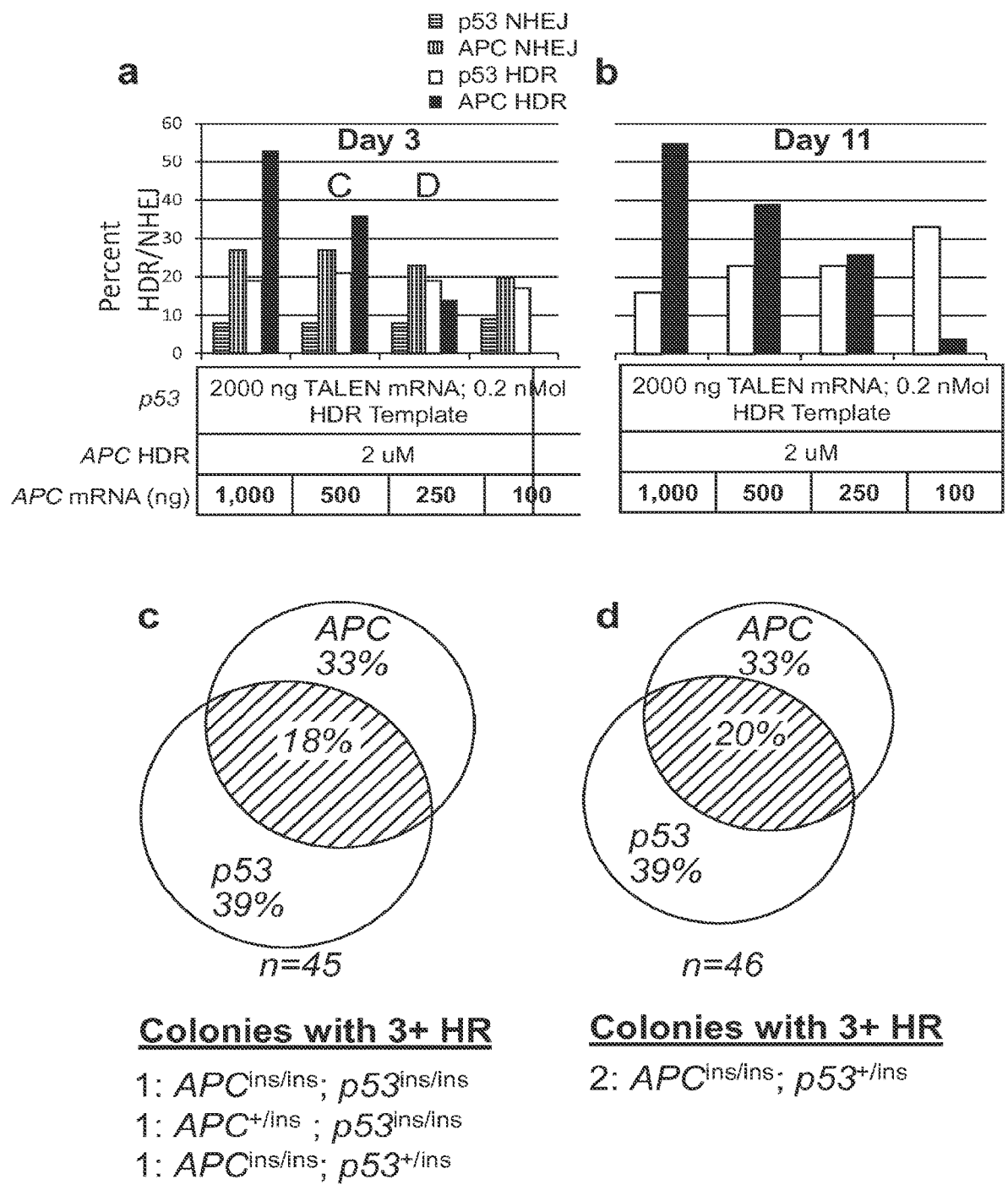
FIG. 4 Multiplex gene editing of swine APC and p53. Panel a) Surveyor and RFLP analysis to determine the efficiency of non-homologous end joining (NHEJ) and homology depended repair HDR on cell populations 3 days post transfection. Panel b) RFLP analysis for homology dependent repair on cell populations 11 days post transfection. Panels c and d) Percentage of colonies positive derived from the indicated cell population (indicated in panel a, "C" and "D") for HDR at APC, p53 or both. Colonies with 3 or more HDR alleles are listed below.

Example 2, see FIG. 4, describes experiments that had the same goal of multiplex HDR editing but for different genes. The first gene target was Adenomatous polyposis coli (APC). The second gene target was p53 (the TP53 gene). Cells homozygous for both knockouts and cells heterozygous for both knockouts were detected and isolated.

Example 3, see FIGS. 5-8, describes multiplex HDR editing to knockout 2-5 genes. There were three experiments, with the number of cell colonies tested for genotype ranging from 72-192 for each experiment. Cells were treated for multiplex knockout of various combinations the genes APC, p53, RAG2, Low Density Lipoprotein Receptor (LDLR), IL2Rg, Kisspeptin Receptor (KISSR or GPR54), and Eukaryotic Translation Initiation Factor 4GI (EIF4GI). The gene LDLR was consistently less amenable to modification than the other genes. As is evident from the results, multiple alleles can be disrupted simultaneously using the TALEN-specified, homology directed repair (HDR). Five TALEN pairs that each resulted in more than 20% HDR/site and their cognate HDR templates were simultaneously co-transfected in three combinations (Table A). A proportion of colonies from each replicate were positive for HDR events in at least four genes and two colonies from replicate-A had HDR events in all five genes. Although simultaneous indel formation in five genes has been demonstrated by Cas9/CRISPR-stimulated NHEJ in mouse ES cells, the precise modification of 5 genes (up to 7 alleles) by targeted nuclease-stimulated HDR is unexpected, surprising, and unrivaled. When the TALENs of replicate were replaced Cas9/CRISPRs (vectors were introduced into cells to express), modification levels were below detection (data not shown); however, other data points to RGEN multiplex, e.g., Example 9 below. Four genes were found to be edited in all experiments and five genes in one experiment.

The speed and efficiency of this process lends itself to scaling-up such that the multiplex knockout of more than 5 genes is achievable without changing the nature of the process. Referring to Table A, about 72 to 192 cells were tested; now that this process has been established it is not unreasonable to increase the number of tests to a very much larger number of cells such that multiplex of larger numbers of genes/alleles can be expected. A number of multiplex genes or alleles may be from 2-25; artisans will immediately appreciate that all ranges and values between the explicitly stated bounds are contemplated, with any of the following being available as an upper or lower limit in combination with each other: 2, 4, 5, 6, 7, 8, 9, 10, 11, 12, 14, 16, 18, 20, 25.

TABLE A

Multiplex HDR in pig fibroblasts

| Genes edited | Rep A # (percent) | Rep B # (percent) | Rep C # (percent) |
|---|---|---|---|
| 5 | 2 (3) | 0 | 0 |
| 4 | 0 | 5 (5) | 4 (2) |
| 3 | 3 (4) | 7 (7) | 14 (7) |
| 2 | 12 (17) | 23 (24) | 41 (21) |
| 1 | 24 (33) | 29 (30) | 47 (24) |
| 1+ | 41 (57) | 63 (66) | 106 (55) |

Genes targeted in each replicate:

| | |
|---|---|
| A. | APC, LDLR, RAG2, IL2Rg, p53. |
| B | APC, LDLR, RAG2, KISSR, EIF4G1 |
| C. | APC, LDLR, RAG2, KISSR, DMD |

As is evident, cells and embryos with multiplex knockouts are embodiments of the invention, as well as animals made thereby.

Example 4 describes some detailed processes for making various animals and refers to certain genes by way of example. Example 5 describes examples of CRISPR/Cas9 design and production.

Example 6 provides further examples of multiplex gene editing with targeted nucleases driving HDR processes. GATA binding protein 4 (GATA4); homeobox protein NKX2-5 (NKX2-5) and Mesoderm Posterior Protein 1 (MESP1) were simultaneously targeted with TALENS and HDR templates to direct frame-shift mutations and premature stop-codons into each gene. The objective was to create biallelic knockouts for each gene for use in complementation studies. The process was about 0.5% efficient as 2 clones had the intended biallelic HDR at each gene. The given genes knocked out singly or in combination genes will cause a failure to thrive genotype and early embryonic lethality without complementation. Artisans will appreciate that knockout of these genes individually and interbreeding of heterozygotes to obtain triple knockouts (about 1/66 chance) for FTT and complementation studies is not feasible in livestock.

Example 7 provides data that TALENs and Cas9/CRISPR can be mixed to perform multiplex editing of genes. Some genes/alleles are more readily targeted by a TALEN, or Cas9/CRISPR and that the situation may arise that multiplexing must be done with a combination of these tools. In this example, the Eukaryotic Translation Initiation Factor 4GI (EIF4GI) was targeted by TALENs and the p65 (RELA) gene was targeted by Cas9/CRISPR. The cells were analyzeD by RFLP assay, indicative of HDR events, and HDR was evident at both sites. Accordingly, TALENs and RGENs may be used together or separately for multiplexing Combinations including, for example, 1, 2, 3 4, 5, 6, 7, 8, 9 or 10 TALENS with 1, 2, 3 4, 5, 6, 7, 8, 9 or 10 RGEN reagents, in any combination.

Chimeras

Chimeras can be made by preparing a host blastocyst and adding a donor cell from a donor animal. The resultant animal will be a chimer that has cells that originate from both the host and the donor. Some genes are required for the embryo to create certain kinds of cells and cell lineages. When such a gene is knocked out in the host cells, the introduction of a donor cell that has the missing gene can result in those cells and cell lineages being restored to the host embryo; the restored cells have the donor genotype. Such a process is referred to as a complementation process.

Matsunari et al., PNAS 110:4557-4562, 2013, described a complementation process for making a donor-derived pig pancreas. They made a host pig blastocyst that was altered to prevent formation of a functional pancreas. They made the host blastocyst by somatic cell cloning. The somatic cell had been modified to overexpress Hes1 under the promoter of Pdx1 (pancreatic and duodenal homeobox 1), which was known to inhibit pancreatic development. The added donor cells to the host blastocyst that did not have this modification; the donor cells supplied the cell lineages needed to make the pancreas. They had already demonstrated elsewhere that functional organs can be generated from pluripotent stem cells (PSCs) in vivo by blastocyst complementation in organogenesis-disabled mouse embryos. They proposed future research using xenogenic pluripotent stem cells (PSCs), including human induced PSCs. Indeed, xenotransplantation has been considered a potential solution to the organ/tissue shortage for greater than 40 years. The fact that no genes were knocked out to disable the formation of the pancreas is significant.

Knocking out even one gene in a large vertebrate is a significant investment of resources using conventional processes. In contrast, overexpression of a gene product in a cell is readily achieved using the present state of the art, for instance, with a plasmid or a vector that places multiple gene cassette copies into the genome. Adding expression of a gene is easier than targeting a gene and knocking it out. The ability to prevent organogenesis by overexpression of a gene product is believed to be unusual at this time. In fact, limitations in the ability to engineer large animal genomes can be significant. Nonetheless, the pig is the preferred donor animal for xenotransplantation due to its similarity in size and physiology to humans as well as its high fecundity and growth rate.

Figure 9:
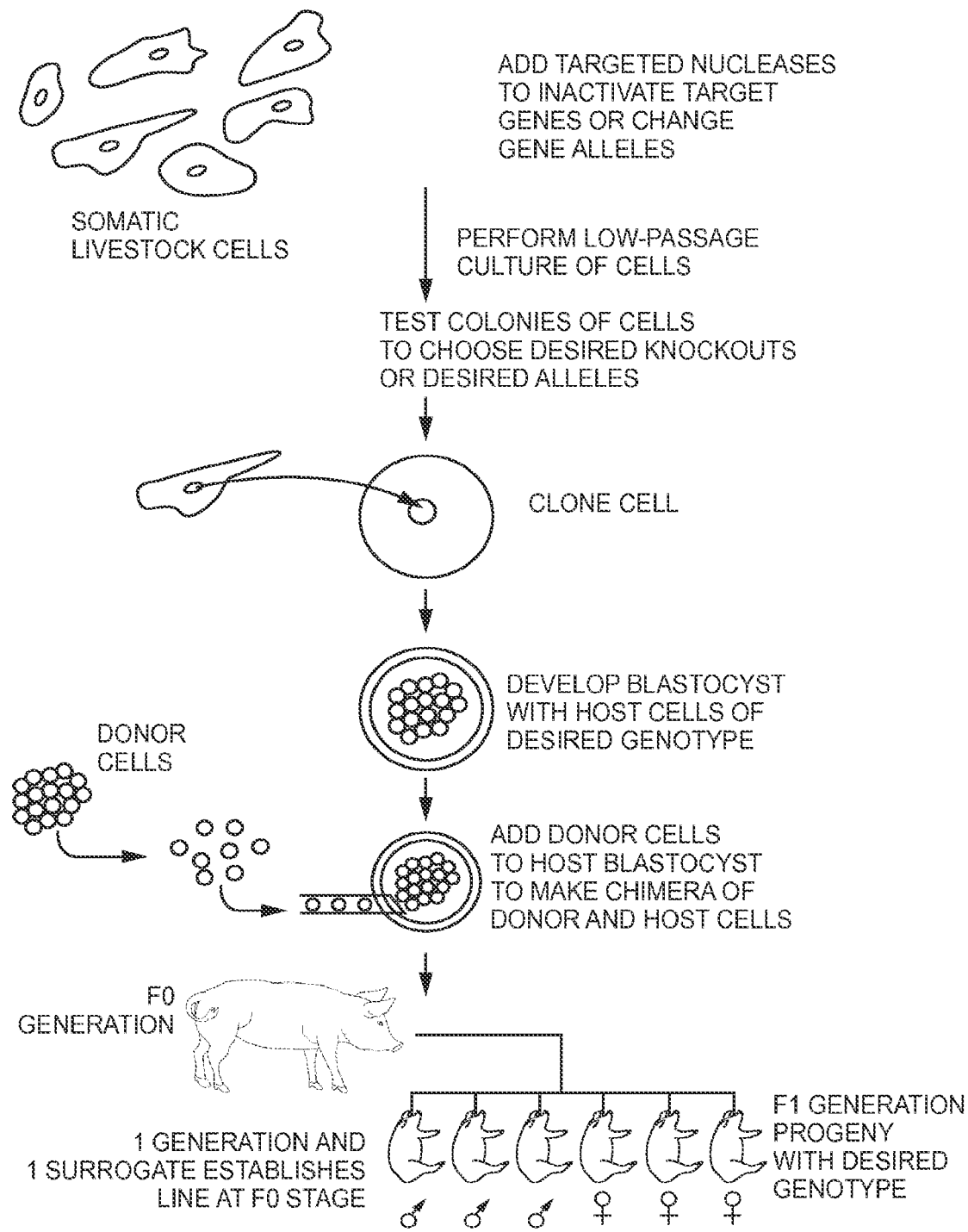
FIG. 9 depicts a process of making an F0 generation chimera with targeted nucleases that produce a desired gene knockout or choice of alleles.

FIG. 9 depicts a multiplex process used herein to make gene knockouts or other gene edits as applied in the context of chimeras. Low-passage primary somatic cells are made with gene knockouts. Cells with exactly the desired distribution of heterozygosity and homozygosity for the knockouts are isolated. These cells are used in cloning to make an embryo that is allowed to develop as a host blastocyst. The term blastocyst is used broadly herein to refer to embryos from two cells to about three weeks. The term embryo is used broadly to refer to animals from zygote to live birth. A donor embryo is established and used as a source of donor cells that provide genes to populate the niche created by the knockouts. The donor cells are introduced into the host blastocyst and reproduce with the host cells to form a chimera having both host and donor cells. The embryo is transferred to a surrogate female and gestated. The progeny of the chimera have host genotypes when the host cells form the gametes. Chimeras have their gender determined by their host blastocyst.

Figure 10:
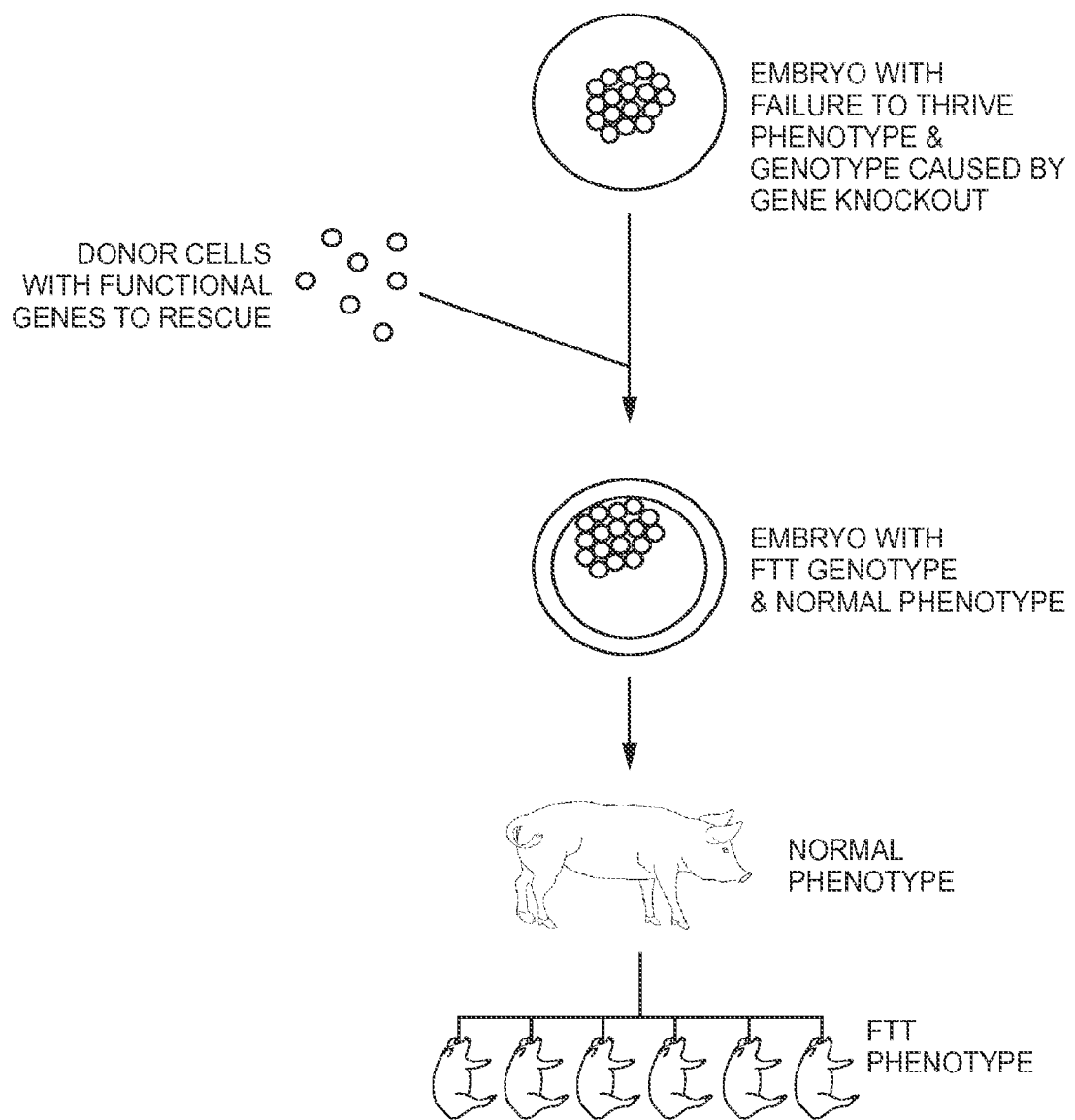
FIG. 10 depicts establishment of an F0 generation animal with a normal phenotype and progeny with a failure to thrive (FTT) phenotype and genotype.

FIG. 10 illustrates a failure to thrive phenotype (FTT) complementation process. FTT refers to animals that are not expected to live to an age of sexual maturity. A host embryo is provided with an FTT genotype and phenotype. Multiplex processes are ideal because the FTTs available by knockout of just one gene are limited and are not known for some organs and tissues. The donor cells provide the genes missing in the FTT and provide the missing cell types. The embryo can be a large vertebrate animal and the knockouts can be multiplex, e.g., 2-25 genes. Moreover, targeted endonucleases can be used to achieve a knockout. In an immunodeficiency embodiment, an IL2Rg−/y RAG2−/− knockout is the FTT because the host is essentially missing immune functions. But the donor cells do not have those genes missing and the resultant chimera has an essentially normal phenotype for purposes of being able to raise and maintain the animal. But the progeny has the FTT phenotype. The animals can thus be maintained and FTT animals conveniently produced. The chimeras can be any combination of heterozygous and homozygous for the knockouts. Processes for making chimera are thus described that are F0 generation animals that produce failure to thrive (FTT) phenotypes when other processes require an additional generation, or more.

Figure 11:
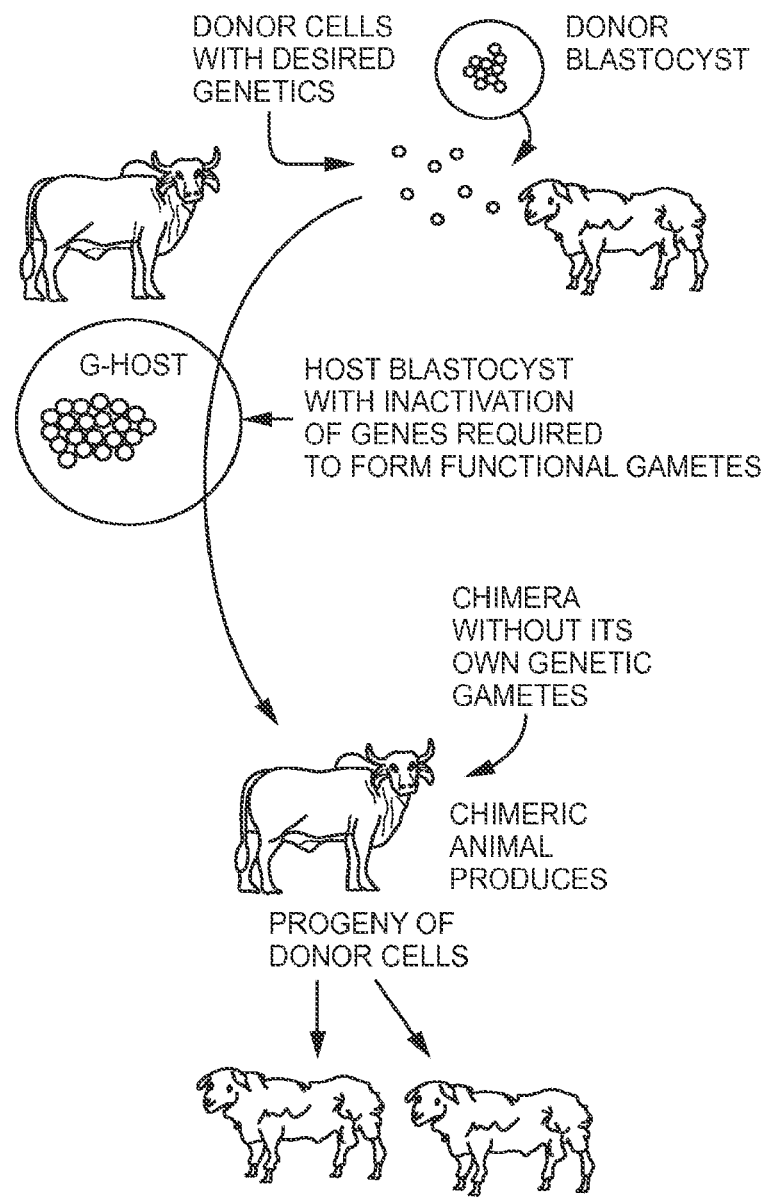
FIG. 11 depicts a process for making chimeric animals with gametes having the genetics of the donor embryo.

Chimera normally pass on the genetics of the host cells. Disclosed herein, however, are alternative chimeras that pass the donor cell genetics to their progeny and not the host cell genetics. It turns out that switching the genetic inheritance can create some useful opportunities. Referring to FIG. 11, an embryo labeled as G⁻ host is depicted. The embryo has been prepared with nonfunctional gametes. A donor blastocyst is prepared and used as a source of donor cells. The donor cells provide the genes and cell lineages that are needed to make donor gametes. The resultant chimera has the gametes of the donor cells and creates progeny having donor cell genetics. In the illustration, the host embryo is a male Brahman bull. The donor cells are from a double-muscled bull. The chimera has a Brahman bull phenotype but its progeny are double muscled. The host and donors may be from the same or different breeds or same or different species. The host has been prepared to be sterile, meaning that it cannot sexually reproduce. Some sterile animals may be used to make gametes that are nonfunctional, e.g., immotile sperm, or not make gametes at all, e.g., with early gametogenesis being disrupted. The donor cells may be, for instance, wild-type cells, cells from animal breeds having desirable traits, or genetically modified cells.

Embodiments of the invention include chimeric sterile animals, such as chimeric livestock, that have a genetic modification to a chromosome that prevents gametogenesis or spermatogenesis. The chromosome may be an X chromosome, a Y chromosome, or an autosome. The modification may include a disruption of an existing gene. The disruption may be created by altering an existing chromosomal gene so that it cannot be expressed, or by genetically expressing factors that will inhibit the transcription or translation of a gene. The term gametogenesis means the production of haploid sex cells (ova and spermatozoa) that each carry one-half the genetic compliment of the parents from the germ cell line of each parent. The production of spermatozoa is spermatogenesis. The fusion of spermatozoa and ova during fertilization results in a zygote cell that has a diploid genome. The term gametogenic cell refers to a progenitor to an ovum or sperm, typically a germ cell or a spermatogonial cell. One embodiment is a knockout of spermatogonial stem cells (SSC) in the host. The animal may be made with donor cells that have desirable genetics and supplies SSC cells that make gametes with the donor genotype. Some genes are disrupted in combination to produce one or more effects that cause infertility, for instance, combinations of: Acr/H1.1/Smcp, Acr/Tnp2/Smcp, Tnp2/H1.1/Smcp, Acr/Hlt/Smcp, Tnp2/Hlt/Smcp (Nayernia K; Drabent B; Meinhardt A; Adham I M; Schwandt I; Muller C; Sancken U; Kleene K C; Engel W Triple knockouts reveal gene interactions affecting fertility of male mice. Mol. Reprod. Dev 70(4):406-16, 2005). Embodiments include a first line of animals with a knockout of a first gene or genes and a second line of animals with a knockout of a second gene or genes so that male progeny of the lines are infertile.

The use of genetic engineering to create genetically modified large vertebrates will accelerate the creation of animals with desirable traits. Traditional livestock breeding is an expensive and time consuming process that involves careful selection of genetic traits and lengthy waits for generational reproduction. Even with careful trait selection, the variations of sexual reproduction present a considerable challenge in cultivating and passing on desirable trait combinations. But creation of chimeras that pass on donor traits creates methods of animal reproduction that allow for rapid dissemination of desirable genetic traits, as well as for protection of the proprietary control of the traits. Embodiments include the production of genetically and genomically sterile animals that can serve as hosts for donated genetic material. Sexual intercourse by the host will lead to reproduction of the donor's genetic material. A group of genetically sterile animals can be used to disseminate identical genes from a single donor by sexual reproduction so that many donor progeny may be rapidly generated. Embodiments include animals that are modified to produce only one gender of animal so that users receiving the animals will not be able to easily breed the animals with the traits.

Embodiments include making a genetic modification to cells or embryos to inactivate a gene or plurality of genes selective for gametogenesis or spermatozoa activity. One process of genetic modification involves introduction of a targeted nuclease, e.g., a Cas9/CRISPR or mRNA for a TALEN pair that specifically binds to the gene. An animal is cloned from the cells or the modified embryo is directly raised in a surrogate mother. The animal may be a livestock animal or other animal. Gametogenesis may be blocked at an early stage. Or spermatozoa activity may be disrupted that is essential for fertility but is not otherwise essential to the animal. The animal is thus sterile because it cannot sexually reproduce; however, ARTs may be used to create progeny from the modified sperm. A donor animal that has desirable genetic traits (as a result of breeding and/or genetic engineering) is selected.

Rapid Establishment of F0 Generation Founder Animal Lines with Two or More Knockouts With multiplex, two, three, or more genes (2-25) may be simultaneously knocked out to produce an F0 generation with the desired combination of alleles. If homozygosity for all of the knockouts creates an FTT, then one option is to make the founders homozygous for all of the knockouts except for one—or whatever the minimum heterozygosity should be for that situation. The one heterozygote gene can allow for a non-FTT phenotype. Alternatively, the multiplex knockouts can be used in combination with complementation to make thriving chimera that have FTT progeny. This process can eliminate generations in the creation of a multiple knockout animal.

In either case, the advantages are large and move many processes into the realm of actually being achievable. Producing animals with knockouts of two loci by conventional breeding is cost prohibitive as only ~6% of offspring would have the desired phenotype in the F2 generation (Table B). In contrast, the multiplex approach enables production of the desired genotype in the F0 generation, a large advantage over conventional knockouts and breeding. It should be stressed that the saving of time and animals is not theoretical: it is an advance that makes some kinds of modifications possible because success is expected instead of failure. Furthermore, to continue the example, breeding between one or two chimeric RG-KO parents would significantly increase the production rate of RG-KO offspring to 25 and 100 percent respectively (Table B).

TABLE B

| Breeding advantage of chimeric pigs. | | |
|---|---|---|
| Male | Female | % RG-KO |
| Chimera-IL2Rg$^{y/-}$; RAG2$^{-/-}$ X | Chimera-IL2Rg$^{-/-}$; RAG2$^{-/-}$ | 100% |
| Chimera- IL2Rg$^{y/-}$; RAG2$^{-/-}$ X | IL2Rg$^{+/-}$; RAG2$^{+/-}$ | 25% |
| IL2Rg$^{y/+}$; RAG2$^{+/-}$ X | IL2Rg$^{+/-}$, RAG2$^{+/-}$ | 6.3% |

Immunodeficient Animals

One group of embodiments relates to immunodeficient pigs or other livestock and processes of making them. These embodiments are examples of multiplex edits, e.g., knockouts, that take advantage of the opportunity to manage selection of homozygous and heterozygous knockout genotypes. These demonstrate the power of multiplex to rapidly establish founder lines. They also include further aspects of the inventions that involve making chimeras.

The pig is the most relevant, non-primate animal model that mimics the size and physiology of humans. Unfortunately, fully immunodeficient pigs are not widely available because (1) multiple gene knockouts (KOs) are required, (2) intercrossing to create multi-locus null animals is extremely costly and depending on the number of Kos may be possible, and (3) only small scale germ-free facilities are available for pigs. Herein, embodiments include large vertebrate animals with a knockout of both RAG2 and IL2Rg (i.e., RG-KO). The term large vertebrate refers to simians, livestock, dogs, and cats. The term livestock refers to animals customarily raised for food, such as cattle, sheep, goats, avian (chicken, turkey), pigs, buffalo, and fish. The genes can be knocked out of somatic cells that are then used for cloning to produce a whole animal. Alternatively, embryos can be treated to knockout the genes, with the animals being derived directly from the embryos. The multiplex gene-targeting platform can simultaneously disrupt of T, B and NK cell development in the pig. Accordingly, animals made without such cells can be made directly with the methods herein, as F0 founders, but the phenotype is FTT.

Agricultural Targets for Multiplex Edits

The editing of food animal genomes can be greatly accelerated by editing numerous loci at the same time, saving generations of animal breeding that would be required to bring together alleles that are generated instead one at a time. In addition, some agricultural traits are complex, meaning that they are manifest as a result of the influence of alleles at more than one gene (from 2 to hundreds). For example, polymorphisms at DGAT, ABCG2, and a polymorphism on chromosome 18 together account for a large portion of the variation in Net Dairy Merit in dairy cattle. Livestock cells or embryos can be subjected to multiplex editing of numerous genes, including various agricultural targets: one or more of ACAN, AMELY, BLG, BMP 1B (FecB), DAZL, DGAT, Eif4GI, GDF8, Horn-poll locus, IGF2, CWC15, KissR/GRP54, OFD1Y, p65, PRLR, Prmd14, PRNP, Rosa, Socs2, SRY, ZFY, β-lactoglobulin, CLPG.

Disease Modeling Targets for Multiplexing:

Some traits, like cancer, are caused on the basis of mutations at multiple genes (see APC/p53). In addition, numerous disease traits are so-called Complex traits that manifest as a result of the influence of alleles at more than one gene. For example, diabetes, metabolism, heart disease, and neurological diseases are considered complex traits. Embodiments include animal models that are heterozygous and homozygous for individual alleles, or in combination with alleles at other genes, in different combinations. For example mature onset diabetes of the young (MODY) loci cause diabetes individually and additively, including; MODY 1 (HNF4α), MODY 2 (GCK), MODY 3 (HNF1α), MODY 4 (Pdx1), MODY 5 (HNF-1β), MODY 6 (eurogenic differentiation 1), MODY 7 (KLF 11), MODY 8 (CEL), MODY 9 (PAX4), MODY 10 (INS), MODY 11 (BLK). Livestock cells or embryos can be subjected to multiplex editing of numerous genes for animal modelling, including various disease modeling targets: APC, ApoE, DMD, GHRHR, HR, HSD11B2, LDLR, NF1, NPPA, NR3C2, p53, PKD1, Rbm20, SCNN1G, tP53, DAZL, FAH, HBB, IL2RG, PDX1, PITX3, Runx1, RAG2, GGTA. Embodiments include cells, embryos, and animals with one or more of the above targets being edited, e.g., KO.

Genes in one species consistently have orthologs in other species. Humans and mice genes consistently have orthologs in livestock, particularly among cows, pigs, sheep, goats, chicken, and rabbits. Genetic orthologs between these species and fish is often consistent, depending upon the gene's function. Biologists are familiar with processes for finding gene orthologs so genes may be described herein in terms of one of the species without listing orthologs of the other species. Embodiments describing the disruption of a gene thus include disruption of orthologs that have the same or different names in other species. There are general genetic databases as well as databases that are specialized to identification of genetic orthologs. Moreover, artisans are familiar with the commonly used abbreviations for genes and using the context to identify which gene is being referred to in case there is more than one abbreviation for a gene or two genes are referred to by the same abbreviation.

Spermatogonial stem cells offer a second method genetic modification of livestock. Genetic modification or gene edits can be executed in vitro in spermatogonial stem cells isolated from donor testes. Modified cells are transplanted into germ cell-depleted testes of a recipient. Implanted spermatogonial stem cells produce sperm that carry the genetic modification(s) that can be used for breeding via artificial insemination or in vitro fertilization (IVF) to derive founder animals.

Complementation of Nullomorphic Cell or Organ Loss by Selective Depopulation of Host Niches.

Multiplex editing can be used to purposefully ablate cells or organs from a specific embryonic or animal niche, creating an environment conducive to better donor cell integration, proliferation, and differentiation, enhancing their contribution by complementation orthologous cells, tissues or organs in the embryo, fetus or animal. The animal with the empty niche is a deficiency carrier because it has been created to have a deficiency that can be filled by donor cells and genes. Specific examples include the recipient-elimination, and donor-rescue of gametogenic cell lineages (DAZL, VASA, MIWI, PIWI, and so forth).

In another embodiment multiplex gene editing can be used to induce congenital alopecia, providing opportunity for donor derived cells to participate in hair folliculogenesis. The genes considered for multiplex gene editing to cause alopecia include those identified in OMIM and the Human Phenotype Ontology database; DCAF17, VDR, PNPLA1, HRAS, Telomerase-vert, DSP, SNRPE, RPL21, LAMA3, UROD, EDAR, OFD1, PEX7, COL3A1, ALOX12B, HLCS, NIPAL4, CERS3, ANTXR1, B3GALT6, DSG4, UBR1, CTC1, MBTPS2, UROS, ABHD5, NOP10, ALMS1, LAMB3, EOGT, SAT1, RBPJ, ARHGAP31, ACVR1, IKBKG, LPAR6, HR, ATR, HTRA1, AIRE, BCS1L, MCCC2, DKC1, PORCN, EBP, SLITRK1, BTK, DOCK6, APCDD1, ZIP4, CASR, TERT, EDARADD, ATP6VOA2, PVRL1, MGP, KRT85, RAG2, RAG-1, ROR2, CLAUDINI, ABCA12, SLA-DRA1, B4GALT7, COL7A1, NHP2, GNA11, WNT5A, USB1, LMNA, EPS8L3, NSDHL, TRPV3, KRAS, TINF2, TGM1, DCLRE1C, PKP1, WRAP53, KDM5C, ECM1, TP63, KRT14, RIPK4. Chimerism with donor cells that have folliculogenic potential may be used to grow human hair follicles. The ablation of organs or tissues in pigs or other vertebrates and growth of organs or tissues from human origins is particularly useful as a source of medical organs or tissues.

Further complementation targets for multiplexing are: PRKDC, BCL11a, BMI1, CCR5, CXCR4, DKK1, ETV2, FLI1, FLK1, GATA2, GATA4, HHEX, KIT, LMX1A, MYF5, MYOD1, MYOG, NKX2-5, NR4A2, PAX3, PDX1, PITX3, Runx1, RAG2, GGTA, HR, HANDII, TBX5.

Embodiments include targeting one, two, or more (2-25) of the above targets in a multiplex approach or by other approaches.

Edited Genes

The methods and inventions described herein with respect to particular targets and targeted endonucleases are broadly applicable. The inventors have prepared primary livestock cells suitable for cloning with edits with all of the following genes.

TABLE C

Primary livestock cells suitable for cloning, produced in swine and/or bovine fibroblasts by targeted endonucleases (TALENs) and HDR knockout.

| Gene ID | Gene Name | Species S: Swine B: Bovine |
|---|---|---|
| ETV2 | Ets Variant 2 | S |
| PDX1 | Pancreatic and duodenal homeobox 1 | S |
| TBX4 | T-box transcription factor TBX4 | S |
| ID2 | DNA-binding protein inhibitor | S |
| SOX2 | SRY (sex determining region Y)-box 2 | S |
| TTF1/NKX2-1 | thyroid transcription factor 1/ NK2 homeobox 1 | S |
| MESP1 | mesoderm posterior 1 homolog | S |
| GATA4 | GATA binding protein 4 | S |
| NKX2-5 | NK2 homeobox 5 | S |
| FAH | Fumarylacetoacetate Hydrolase | S |
| PRKDC | protein kinase, DNA-activated, catalytic polypeptide | S |
| RUNX1 | Runt-related transcription factor 1 | S |
| FLI1 | Friend leukemia integration 1 transcription factor | S |
| PITX3 | Pituitary homeobox 3 | S |
| LMX1A | LIM homeobox transcription factor 1, alpha | S |
| DKK1 | Dickkopf-related protein 1 | S |
| NR4A2/NURR1 | Nuclear receptor subfamily 4, group A, member 2/Nuclear receptor related 1 protein | S |
| FLK1 | Fetal Liver Kinase 1 | S |
| HHEX1 | Hematopoietically-expressed homeobox protein | S |
| BCL11A | B-cell lymphoma/leukemia 11A | S |
| RAG2 | Recombination activating gene 2 | S |
| RAG1 | Recombination activating gene 1 | S |
| IL2RG | Interleukin 2 receptor, gamma | S |
| c-KIT/SCFR | Mast/stem cell growth factor receptor | S |
| BMI1 | polycomb ring finger oncogene | S |
| HANDII | Heart-and neural crest derivatives-expressed protein 2 | S |
| TBX5 | T-box transcription factor 5 | S |
| GATA2 | GATA binding protein 2 | S |
| DAZL | Deleted in Azoospermia like | S, B |
| OLIG1 | oligodendrocyte transcription factor 1 | S |
| OLIG2 | oligodendrocyte transcription factor 2 | S |

Genetically Modified Animals

Animals may be made that are mono-allelic or bi-allelic for a chromosomal modification, using methods that either leave a genetically expressible marker in place, allow for it to be bred out of an animal, or by methods that do not place such a marker in the animal. For instance, the inventors have used methods of homologous dependent recombination (HDR) to make changes to, or insertion of exogenous genes into, chromosomes of animals. Tools such as TALENs and recombinase fusion proteins, as well as conventional methods, are discussed elsewhere herein. Some of the experimental data supporting genetic modifications disclosed herein is summarized as follows. The inventors have previously demonstrated exceptional cloning efficiency when cloning from polygenic populations of modified cells, and advocated for this approach to avoid variation in cloning efficiency by somatic cell nuclear transfer (SCNT) for isolated colonies (Carlson et al., 2011). Additionally, however, TALEN-mediated genome modification, as well as modification by recombinase fusion molecules, provides for a bi-allelic alteration to be accomplished in a single generation. For example, an animal homozygous for a knocked-out gene may be made by SCNT and without inbreeding to produce homozygosity. Gestation length and maturation to reproduction age for livestock such as pigs and cattle is a significant barrier to research and to production. For example, generation of a homozygous knockout from heterozygous mutant cells (both sexes) by cloning and breeding would require 16 and 30 months for pigs and cattle respectively. Some have allegedly reduced this burden with sequential cycles of genetic modification and SCNT (Kuroiwa et al., 2004) however, this is both technically challenging and cost prohibitive, moreover, there are many reasons for avoiding serial cloning for making F0 animals that are to be actually useful for large vertebrate laboratory models or livestock. The ability to routinely generate bi-allelic KO cells prior to SCNT is a significant advancement in large animal genetic engineering. Bi-allelic knockout has been achieved in immortal cells lines using other processes such as ZFN and dilution cloning (Liu et al., 2010). Another group recently demonstrated bi-allelic KO of porcine GGTA1 using commercial ZFN reagents (Hauschild et al., 2011) where bi-allelic null cells could be enriched by FACS for the absence of a GGTA1-dependent surface epitope. While these studies demonstrate certain useful concepts, they do not show that animals or livestock could be modified because simple clonal dilution is generally not feasible for primary fibroblast isolates (fibroblasts grow poorly at low density) and biological enrichment for null cells is not available for the majority of genes.

Targeted nuclease-induced homologous recombination can be used so as to eliminate the need for linked selection markers. TALENs may be used to precisely transfer specific alleles into a livestock genome by homology dependent repair (HDR). In a pilot study, a specific 11 bp deletion (the Belgian Blue allele) (Grobet et al., 1997; Kambadur et al., 1997) was introduced into the bovine GDF8 locus (see U.S. patent application Ser. No. 13/404,662 filed Feb. 24, 2012). When transfected alone, the btGDF8.1 TALEN pair cleaved up to 16% of chromosomes at the target locus. Co-transfection with a supercoiled homologous DNA repair template harboring the 11 bp deletion resulted in a gene conversion frequency (HDR) of up to 5% at day 3 without selection for the desired event. Gene conversion was identified in 1.4% of isolated colonies that were screened. These results demonstrated that TALENs can be used to effectively induce HDR without the aid of a linked selection marker.

Homology Directed Repair (HDR)

Homology directed repair (HDR) is a mechanism in cells to repair ssDNA and double stranded DNA (dsDNA) lesions. This repair mechanism can be used by the cell when there is an HDR template present that has a sequence with significant homology to the lesion site. Specific binding, as that term is commonly used in the biological arts, refers to a molecule that binds to a target with a relatively high affinity compared to non-target tissues, and generally involves a plurality of non-covalent interactions, such as electrostatic interactions, van der Waals interactions, hydrogen bonding, and the like. Specific hybridization is a form of specific binding between nucleic acids that have complementary sequences. Proteins can also specifically bind to DNA, for instance, in TALENs or CRISPR/Cas9 systems or by Gal4 motifs. Introgression of an allele refers to a process of copying an exogenous allele over an endogenous allele with a template-guided process. The endogenous allele might actually be excised and replaced by an exogenous nucleic acid allele in some situations but present theory is that the process is a copying mechanism. Since alleles are gene pairs, there is significant homology between them. The allele might be a gene that encodes a protein, or it could have other functions such as encoding a bioactive RNA chain or providing a site for receiving a regulatory protein or RNA.

The HDR template is a nucleic acid that comprises the allele that is being introgressed. The template may be a dsDNA or a single-stranded DNA (ssDNA). ssDNA templates are preferably from about 20 to about 5000 residues although other lengths can be used. Artisans will immediately appreciate that all ranges and values within the explicitly stated range are contemplated; e.g., from 500 to 1500 residues, from 20 to 100 residues, and so forth. The template may further comprise flanking sequences that provide homology to DNA adjacent to the endogenous allele or the DNA that is to be replaced. The template may also comprise a sequence that is bound to a targeted nuclease system, and is thus the cognate binding site for the system's DNA-binding member. The term cognate refers to two biomolecules that typically interact, for example, a receptor and its ligand. In the context of HDR processes, one of the biomolecules may be designed with a sequence to bind with an intended, i.e., cognate, DNA site or protein site.

Targeted Endonuclease Systems

Genome editing tools such as transcription activator-like effector nucleases (TALENs) and zinc finger nucleases (ZFNs) have impacted the fields of biotechnology, gene therapy and functional genomic studies in many organisms. More recently, RNA-guided endonucleases (RGENs) are directed to their target sites by a complementary RNA molecule. The Cas9/CRISPR system is a REGEN. tracrRNA is another such tool. These are examples of targeted nuclease systems: these system have a DNA-binding member that localizes the nuclease to a target site. The site is then cut by the nuclease. TALENs and ZFNs have the nuclease fused to the DNA-binding member. Cas9/CRISPR are cognates that find each other on the target DNA. The DNA-binding member has a cognate sequence in the chromosomal DNA. The DNA-binding member is typically designed in light of the intended cognate sequence so as to obtain a nucleolytic action at nor near an intended site. Certain embodiments are applicable to all such systems without limitation; including, embodiments that minimize nuclease re-cleavage, embodiments for making SNPs with precision at an intended residue, and placement of the allele that is being introgressed at the DNA-binding site.

TALENs

The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA or a TALEN-pair.

The cipher for TALs has been reported (PCT Application WO 2011/072246) wherein each DNA binding repeat is responsible for recognizing one base pair in the target DNA sequence. The residues may be assembled to target a DNA sequence. In brief, a target site for binding of a TALEN is determined and a fusion molecule comprising a nuclease and a series of RVDs that recognize the target site is created. Upon binding, the nuclease cleaves the DNA so that cellular repair machinery can operate to make a genetic modification at the cut ends. The term TALEN means a protein comprising a Transcription Activator-like (TAL) effector binding domain and a nuclease domain and includes monomeric TALENs that are functional per se as well as others that require dimerization with another monomeric TALEN. The dimerization can result in a homodimeric TALEN when both monomeric TALEN are identical or can result in a heterodimeric TALEN when monomeric TALEN are different. TALENs have been shown to induce gene modification in immortalized human cells by means of the two major eukaryotic DNA repair pathways, non-homologous end joining (NHEJ) and homology directed repair. TALENs are often used in pairs but monomeric TALENs are known. Cells for treatment by TALENs (and other genetic tools) include a cultured cell, an immortalized cell, a primary cell, a primary somatic cell, a zygote, a germ cell, a primordial germ cell, a blastocyst, or a stem cell. In some embodiments, a TAL effector can be used to target other protein domains (e.g., non-nuclease protein domains) to specific nucleotide sequences. For example, a TAL effector can be linked to a protein domain from, without limitation, a DNA 20 interacting enzyme (e.g., a methylase, a topoisomerase, an integrase, a transposase, or a ligase), a transcription activators or repressor, or a protein that interacts with or modifies other proteins such as histones. Applications of such TAL effector fusions include, for example, creating or modifying epigenetic regulatory elements, making site-specific insertions, deletions, or repairs in DNA, controlling gene expression, and modifying chromatin structure.

The term nuclease includes exonucleases and endonucleases. The term endonuclease refers to any wild-type or variant enzyme capable of catalyzing the hydrolysis (cleavage) of bonds between nucleic acids within a DNA or RNA molecule, preferably a DNA molecule. Non-limiting examples of endonucleases include type II restriction endonucleases such as FokI, HhaI, HindIII, NotI, BbvCl, EcoRI, BglII, and AlwI. Endonucleases comprise also rare-cutting endonucleases when having typically a polynucleotide recognition site of about 12-45 base pairs (bp) in length, more preferably of 14-45 bp. Rare-cutting endonucleases induce DNA double-strand breaks (DSBs) at a defined locus. Rare-cutting endonucleases can for example be a targeted endonuclease, a chimeric Zinc-Finger nuclease (ZFN) resulting from the fusion of engineered zinc-finger domains with the catalytic domain of a restriction enzyme such as FokI or a chemical endonuclease. In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of ortho-phenanthroline, a DNA cleaving molecule, and triplex-forming oligonucleotides (TFOs), known to bind specific DNA sequences. Such chemical endonucleases are comprised in the term "endonuclease" according to the present invention. Examples of such endonuclease include I-See I, I-Chu L I-Cre I, I-Csm I, PI-See L PI-Tti L PI-Mtu I, I-Ceu I, I-See IL I-See III, HO, PI-Civ I, PI-Ctr L PI-Aae I, PI-Bsu I, PI-Dha I, PI-Dra L PI-Mav L PI-Meh I, PI-Mfu L PI-Mfl I, PI-Mga L PI-Mgo I, PI-Min L PI-Mka L PI-Mle I, PI-Mma I, PI-30 Msh L PI-Msm I, PI-Mth I, PI-Mtu I, PI-Mxe I, PI-Npu I, PI-Pfu L PI-Rma I, PI-Spb I, PI-Ssp I, PI-Fae L PI-Mja I, PI-Pho L PI-Tag L PI-Thy I, PI-Tko I, PI-Tsp I, I-MsoI.

A genetic modification made by TALENs or other tools may be, for example, chosen from the list consisting of an insertion, a deletion, insertion of an exogenous nucleic acid fragment, and a substitution. The term insertion is used broadly to mean either literal insertion into the chromosome or use of the exogenous sequence as a template for repair. In general, a target DNA site is identified and a TALEN-pair is created that will specifically bind to the site. The TALEN is delivered to the cell or embryo, e.g., as a protein, mRNA or by a vector that encodes the TALEN. The TALEN cleaves the DNA to make a double-strand break that is then repaired, often resulting in the creation of an indel, or incorporating sequences or polymorphisms contained in an accompanying exogenous nucleic acid that is either inserted into the chromosome or serves as a template for repair of the break with a modified sequence. This template-driven repair is a useful process for changing a chromosome, and provides for effective changes to cellular chromosomes.

The term exogenous nucleic acid means a nucleic acid that is added to the cell or embryo, regardless of whether the nucleic acid is the same or distinct from nucleic acid sequences naturally in the cell. The term nucleic acid fragment is broad and includes a chromosome, expression cassette, gene, DNA, RNA, mRNA, or portion thereof. The cell or embryo may be, for instance, chosen from the group consisting non-human vertebrates, non-human primates, cattle, horse, swine, sheep, chicken, avian, rabbit, goats, dog, cat, laboratory animal, and fish.

Some embodiments involve a composition or a method of making a genetically modified livestock and/or artiodactyl comprising introducing a TALEN-pair into livestock and/or an artiodactyl cell or embryo that makes a genetic modification to DNA of the cell or embryo at a site that is specifically bound by the TALEN-pair, and producing the livestock animal/artiodactyl from the cell. Direct injection may be used for the cell or embryo, e.g., into a zygote, blastocyst, or embryo. Alternatively, the TALEN and/or other factors may be introduced into a cell using any of many known techniques for introduction of proteins, RNA, mRNA, DNA, or vectors. Genetically modified animals may be made from the embryos or cells according to known processes, e.g., implantation of the embryo into a gestational host, or various cloning methods. The phrase "a genetic modification to DNA of the cell at a site that is specifically bound by the TALEN", or the like, means that the genetic modification is made at the site cut by the nuclease on the TALEN when the TALEN is specifically bound to its target site. The nuclease does not cut exactly where the TALEN-pair binds, but rather at a defined site between the two binding sites.

Some embodiments involve a composition or a treatment of a cell that is used for cloning the animal. The cell may be a livestock and/or artiodactyl cell, a cultured cell, a primary cell, a primary somatic cell, a zygote, a germ cell, a primordial germ cell, or a stem cell. For example, an embodiment is a composition or a method of creating a genetic modification comprising exposing a plurality of primary cells in a culture to TALEN proteins or a nucleic acid encoding a TALEN or TALENs. The TALENs may be introduced as proteins or as nucleic acid fragments, e.g., encoded by mRNA or a DNA sequence in a vector.

Zinc Finger Nucleases

Zinc-finger nucleases (ZFNs) are artificial restriction enzymes generated by fusing a zinc finger DNA-binding domain to a DNA-cleavage domain. Zinc finger domains can be engineered to target desired DNA sequences and this enables zinc-finger nucleases to target unique sequences within complex genomes. By taking advantage of endogenous DNA repair machinery, these reagents can be used to alter the genomes of higher organisms. ZFNs may be used in method of inactivating genes.

A zinc finger DNA-binding domain has about 30 amino acids and folds into a stable structure. Each finger primarily binds to a triplet within the DNA substrate. Amino acid residues at key positions contribute to most of the sequence-specific interactions with the DNA site. These amino acids can be changed while maintaining the remaining amino acids to preserve the necessary structure. Binding to longer DNA sequences is achieved by linking several domains in tandem. Other functionalities like non-specific FokI cleavage domain (N), transcription activator domains (A), transcription repressor domains (R) and methylases (M) can be fused to a ZFPs to form ZFNs respectively, zinc finger transcription activators (ZFA), zinc finger transcription repressors (ZFR, and zinc finger methylases (ZFM). Materials and methods for using zinc fingers and zinc finger nucleases for making genetically modified animals are disclosed in, e.g., U.S. Pat. No. 8,106,255; U.S. 2012/0192298; U.S. 2011/0023159; and U.S. 2011/0281306.

Vectors and Nucleic Acids

A variety of nucleic acids may be introduced into cells, for knockout purposes, for inactivation of a gene, to obtain expression of a gene, or for other purposes. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained.

The target nucleic acid sequence can be operably linked to a regulatory region such as a promoter. Regulatory regions can be porcine regulatory regions or can be from other species. As used herein, operably linked refers to positioning of a regulatory region relative to a nucleic acid sequence in such a way as to permit or facilitate transcription of the target nucleic acid.

In general, type of promoter can be operably linked to a target nucleic acid sequence. Examples of promoters include, without limitation, tissue-specific promoters, constitutive promoters, inducible promoters, and promoters responsive or unresponsive to a particular stimulus. In some embodiments, a promoter that facilitates the expression of a nucleic acid molecule without significant tissue- or temporal-specificity can be used (i.e., a constitutive promoter). For example, a beta-actin promoter such as the chicken beta-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes simplex virus thymidine kinase (HSV-TK) promoter, the SV40 promoter, or a cytomegalovirus (CMV) promoter. In some embodiments, a fusion of the chicken beta actin gene promoter and the CMV enhancer is used as a promoter. See, for example, Xu et al., Hum. Gene Ther. 12:563, 2001; and Kiwaki et al., Hum. Gene Ther. 7:821, 1996.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable expressed markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyl-transferase (XGPRT). Such markers are useful for selecting stable transformants in culture. Other selectable markers include fluorescent polypeptides, such as green fluorescent protein or yellow fluorescent protein.

In some embodiments, a sequence encoding a selectable marker can be flanked by recognition sequences for a recombinase such as, e.g., Cre or Flp. For example, the selectable marker can be flanked by loxP recognition sites (34-bp recognition sites recognized by the Cre recombinase) or FRT recognition sites such that the selectable marker can be excised from the construct. See, Orban et al., Proc. Natl. Acad. Sci., 89:6861, 1992, for a review of Cre/lox technology, and Brand and Dymecki, Dev. Cell, 6:7, 2004. A transposon containing a Cre- or Flp-activatable transgene interrupted by a selectable marker gene also can be used to obtain transgenic animals with conditional expression of a transgene. For example, a promoter driving expression of the marker/transgene can be either ubiquitous or tissue-specific, which would result in the ubiquitous or tissue-specific expression of the marker in F0 animals (e.g., pigs). Tissue specific activation of the transgene can be accomplished, for example, by crossing a pig that ubiquitously expresses a marker-interrupted transgene to a pig expressing Cre or Flp in a tissue-specific manner, or by crossing a pig that expresses a marker-interrupted transgene in a tissue-specific manner to a pig that ubiquitously expresses Cre or Flp recombinase. Controlled expression of the transgene or controlled excision of the marker allows expression of the transgene.

In some embodiments, the exogenous nucleic acid encodes a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and FLAG™ tag (Kodak, New Haven, CT).

Nucleic acid constructs can be introduced into embryonic, fetal, or adult artiodactyl/livestock cells of any type, including, for example, germ cells such as an oocyte or an egg, a progenitor cell, an adult or embryonic stem cell, a primordial germ cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to an exogenous nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al., Nucleic Acids Res. 31:6873, 2003); Tol2 (Kawakami, Genome Biology 8(Suppl. 1):S7, 2007; Minos (Pavlopoulos et al., Genome Biology, 8(Suppl. 1):S2, 2007); Hsmar1 (Miskey et al., Mol Cell Biol., 27:4589, 2007); and Passport have been developed to introduce nucleic acids into cells, including mice, human, and pig cells. The Sleeping Beauty transposon is particularly useful. A transposase can be delivered as a protein, encoded on the same nucleic acid construct as the exogenous nucleic acid, can be introduced on a separate nucleic acid construct, or provided as an mRNA (e.g., an in vitro-transcribed and capped mRNA).

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). The term transgenic is used broadly herein and refers to a genetically modified organism or genetically engineered organism whose genetic material has been altered using genetic engineering techniques. A knockout artiodactyl is thus transgenic regardless of whether or not exogenous genes or nucleic acids are expressed in the animal or its progeny.

Genetically Modified Animals

Animals may be modified using TALENs or other genetic engineering tools, including recombinase fusion proteins, or various vectors that are known. A genetic modification made by such tools may comprise disruption of a gene. The term disruption of a gene refers to preventing the formation of a functional gene product. A gene product is functional only if it fulfills its normal (wild-type) functions. Disruption of the gene prevents expression of a functional factor encoded by the gene and comprises an insertion, deletion, or substitution of one or more bases in a sequence encoded by the gene and/or a promoter and/or an operator that is necessary for expression of the gene in the animal. The disrupted gene may be disrupted by, e.g., removal of at least a portion of the gene from a genome of the animal, alteration of the gene to prevent expression of a functional factor encoded by the gene, an interfering RNA, or expression of a dominant negative factor by an exogenous gene. Materials and methods of genetically modifying animals are further detailed in U.S. Pat. No. 8,518,701; U.S. 2010/0251395; and U.S. 2012/0222143 which are hereby incorporated herein by reference for all purposes; in case of conflict, the instant specification is controlling. The term trans-acting refers to processes acting on a target gene from a different molecule (i.e., intermolecular). A trans-acting element is usually a DNA sequence that contains a gene. This gene codes for a protein (or microRNA or other diffusible molecule) that is used in the regulation the target gene. The trans-acting gene may be on the same chromosome as the target gene, but the activity is via the intermediary protein or RNA that it encodes. Embodiments of trans-acting gene are, e.g., genes that encode targeting endonucleases. Inactivation of a gene using a dominant negative generally involves a trans-acting element. The term cis-regulatory or cis-acting means an action without coding for protein or RNA; in the context of gene inactivation, this generally means inactivation of the coding portion of a gene, or a promoter and/or operator that is necessary for expression of the functional gene.

Various techniques known in the art can be used to inactivate genes to make knock-out animals and/or to introduce nucleic acid constructs into animals to produce founder animals and to make animal lines, in which the knockout or nucleic acid construct is integrated into the genome. Such techniques include, without limitation, pronuclear microinjection (U.S. Pat. No. 4,873,191), retrovirus mediated gene transfer into germ lines (Van der Putten et al., Proc. Natl. Acad. Sci. USA, 82:6148-6152, 1985), gene targeting into embryonic stem cells (Thompson et al., Cell, 56:313-321, 1989), electroporation of embryos (Lo, Mol. Cell. Biol., 3:1803-1814, 1983), sperm-mediated gene transfer (Lavitrano et al., Proc. Natl. Acad. Sci. USA, 99:14230-14235, 2002; Lavitrano et al., Reprod. Fert. Develop., 18:19-23, 2006), and in vitro transformation of somatic cells, such as cumulus or mammary cells, or adult, fetal, or embryonic stem cells, followed by nuclear transplantation (Wilmut et al., Nature 385:810-813, 1997; and Wakayama et al., Nature 394:369-374, 1998). Pronuclear microinjection, sperm mediated gene transfer, and somatic cell nuclear transfer are particularly useful techniques. An animal that is genomically modified is an animal wherein all of its cells have the genetic modification, including its germ line cells. When methods are used that produce an animal that is mosaic in its genetic modification, the animals may be inbred and progeny that are genomically modified may be selected. Cloning, for instance, may be used to make a mosaic animal if its cells are modified at the blastocyst state, or genomic modification can take place when a single-cell is modified. Animals that are modified so they do not sexually mature can be homozygous or heterozygous for the modification, depending on the specific approach that is used. If a particular gene is inactivated by a knockout modification, homozygousity would normally be required. If a particular gene is inactivated by an RNA interference or dominant negative strategy, then heterozygosity is often adequate.

Typically, in pronuclear microinjection, a nucleic acid construct is introduced into a fertilized egg; 1 or 2 cell fertilized eggs are used as the pronuclei containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18-gauge needles and under vacuum. Follicular fluid and aspirated oocytes can be rinsed through pre-filters with commercial TL-HEPES (Minitube, Verona, WI). Oocytes surrounded by a compact cumulus mass can be selected and placed into TCM-199 OOCYTE MATURATION MEDIUM (Minitube, Verona, WI) supplemented with 0.1 mg/mL cysteine, 10 ng/mL epidermal growth factor, 10% porcine follicular fluid, 50 µM 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium, which will not contain cAMP, PMSG or hCG and incubated for an additional 22 hours. Matured oocytes can be stripped of their cumulus cells by vortexing in 0.1% hyaluronidase for 1 minute.

For swine, mature oocytes can be fertilized in 500 µl Minitube PORCPRO IVF MEDIUM SYSTEM (Minitube, Verona, WI) in Minitube 5-well fertilization dishes. In preparation for in vitro fertilization (IVF), freshly-collected or frozen boar semen can be washed and resuspended in PORCPRO IVF Medium to $4 \times 10^5$ sperm. Sperm concentrations can be analyzed by computer assisted semen analysis (SPERMVISION, Minitube, Verona, WI). Final in vitro insemination can be performed in a 10 µl volume at a final concentration of approximately 40 motile sperm/oocyte, depending on boar. Incubate all fertilizing oocytes at 38.7° C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs can be injected into one of the pronuclei. Then the injected eggs can be transferred to a recipient female (e.g., into the oviducts of a recipient female) and allowed to develop in the recipient female to produce the transgenic animals. In particular, in vitro fertilized embryos can be centrifuged at 15,000×g for 5 minutes to sediment lipids allowing visualization of the pronucleus. The embryos can be injected with using an Eppendorf FEMTOJET injector and can be cultured until blastocyst formation. Rates of embryo cleavage and blastocyst formation and quality can be recorded.

Embryos can be surgically transferred into uteri of asynchronous recipients. Typically, 100-200 (e.g., 150-200) embryos can be deposited into the ampulla-isthmus junction of the oviduct using a 5.5-inch TOMCAT© catheter. After surgery, real-time ultrasound examination of pregnancy can be performed.

In somatic cell nuclear transfer, a transgenic artiodactyl cell (e.g., a transgenic pig cell or bovine cell) such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic cell into an enucleated oocyte arrested at meiosis 2. In some conventions, oocytes arrested at meiosis-2 are termed eggs. After producing a porcine or bovine embryo (e.g., by fusing and activating the oocyte), the embryo is transferred to the oviducts of a recipient female, about 20 to 24 hours after activation. See, for example, Cibelli et al., Science 280:1256-1258, 1998, and U.S. Pat. No. 6,548,741. For pigs, recipient females can be checked for pregnancy approximately 20-21 days after transfer of the embryos.

Standard breeding techniques can be used to create animals that are homozygous for the exogenous nucleic acid from the initial heterozygous founder animals. Homozygosity may not be required, however. Transgenic pigs described herein can be bred with other pigs of interest. In some embodiments, a nucleic acid of interest and a selectable marker can be provided on separate transposons and provided to either embryos or cells in unequal amount, where the amount of transposon containing the selectable marker far exceeds (5-10 fold excess) the transposon containing the nucleic acid of interest. Transgenic cells or animals expressing the nucleic acid of interest can be isolated based on presence and expression of the selectable marker. Because the transposons will integrate into the genome in a precise and unlinked way (independent transposition events), the nucleic acid of interest and the selectable marker are not genetically linked and can easily be separated by genetic segregation through standard breeding. Thus, transgenic animals can be produced that are not constrained to retain selectable markers in subsequent generations, an issue of some concern from a public safety perspective.

Once transgenic animal have been generated, expression of an exogenous nucleic acid can be assessed using standard techniques. Initial screening can be accomplished by Southern blot analysis to determine whether or not integration of the construct has taken place. For a description of Southern analysis, see sections 9.37-9.52 of Sambrook et al., Molecular Cloning, A Laboratory Manual, second edition, Cold Spring Harbor Press, Plainview; NY., 1989. Polymerase chain reaction (PCR) techniques also can be used in the initial screening. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example PCR Primer: A Laboratory Manual, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis, Genetic Engineering News 12:1, 1992; Guatelli et al., Proc. Natl. Acad. Sci. USA, 87:1874, 1990; and Weiss, Science 254:1292, 1991. At the blastocyst stage, embryos can be individually processed for analysis by PCR, Southern hybridization and splinkerette PCR (see, e.g., Dupuy et al. Proc Natl Acad Sci USA, 99:4495, 2002).

Expression of a nucleic acid sequence encoding a polypeptide in the tissues of transgenic pigs can be assessed using techniques that include, for example, Northern blot analysis of tissue samples obtained from the animal, in situ hybridization analysis, Western analysis, immunoassays such as enzyme-linked immunosorbent assays, and reverse-transcriptase PCR (RT-PCR).

Interfering RNAs

A variety of interfering RNA (RNAi) are known. Double-stranded RNA (dsRNA) induces sequence-specific degradation of homologous gene transcripts. RNA-induced silencing complex (RISC) metabolizes dsRNA to small 21-23-nucleotide small interfering RNAs (siRNAs). RISC contains a double stranded RNAse (dsRNase, e.g., Dicer) and ssRNase (e.g., Argonaut 2 or Ago2). RISC utilizes antisense strand as a guide to find a cleavable target. Both siRNAs and microRNAs (miRNAs) are known. A method of disrupting a gene in a genetically modified animal comprises inducing RNA interference against a target gene and/or nucleic acid such that expression of the target gene and/or nucleic acid is reduced.

For example, the exogenous nucleic acid sequence can induce RNA interference against a nucleic acid encoding a polypeptide. For example, double-stranded small interfering RNA (siRNA) or small hairpin RNA (shRNA) homologous to a target DNA can be used to reduce expression of that DNA. Constructs for siRNA can be produced as described, for example, in Fire et al., Nature 391:806, 1998; Romano and Masino, Mol. Microbiol. 6:3343, 1992; Cogoni et al., EMBO J. 15:3153, 1996; Cogoni and Masino, Nature, 399:166, 1999; Misquitta and Paterson Proc. Natl. Acad. Sci. USA, 96:1451, 1999; and Kennerdell and Carthew, Cell, 95:1017, 1998. Constructs for shRNA can be produced as described by McIntyre and Fanning (2006) BMC Biotechnology 6:1. In general, shRNAs are transcribed as a single-stranded RNA molecule containing complementary regions, which can anneal and form short hairpins.

The probability of finding a single, individual functional siRNA or miRNA directed to a specific gene is high. The predictability of a specific sequence of siRNA, for instance, is about 50% but a number of interfering RNAs may be made with good confidence that at least one of them will be effective.

Embodiments include an in vitro cell, an in vivo cell, and a genetically modified animal such as a livestock animal that express an RNAi directed against a gene, e.g., a gene selective for a developmental stage. The RNAi may be, for instance, selected from the group consisting of siRNA, shRNA, dsRNA, RISC and miRNA.

Inducible Systems

An inducible system may be used to control expression of a gene. Various inducible systems are known that allow spatiotemporal control of expression of a gene. Several have been proven to be functional in vivo in transgenic animals. The term inducible system includes traditional promoters and inducible gene expression elements.

An example of an inducible system is the tetracycline (tet)-on promoter system, which can be used to regulate transcription of the nucleic acid. In this system, a mutated Tet repressor (TetR) is fused to the activation domain of herpes simplex virus VP16 trans-activator protein to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A. The agent that is administered to the animal to trigger the inducible system is referred to as an induction agent.

The tetracycline-inducible system and the Cre/loxP recombinase system (either constitutive or inducible) are among the more commonly used inducible systems. The tetracycline-inducible system involves a tetracycline-controlled transactivator (tTA)/reverse tTA (rtTA). A method to use these systems in vivo involves generating two lines of genetically modified animals. One animal line expresses the activator (tTA, rtTA, or Cre recombinase) under the control of a selected promoter. Another set of transgenic animals express the acceptor, in which the expression of the gene of interest (or the gene to be modified) is under the control of the target sequence for the tTA/rtTA transactivators (or is flanked by loxP sequences). Mating the two strains of mice provides control of gene expression.

The tetracycline-dependent regulatory systems (tet systems) rely on two components, i.e., a tetracycline-controlled transactivator (tTA or rtTA) and a tTA/rtTA-dependent promoter that controls expression of a downstream cDNA, in a tetracycline-dependent manner. In the absence of tetracycline or its derivatives (such as doxycycline), tTA binds to tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. Administration of tetracycline or its derivatives allows temporal control of transgene expression in vivo. rtTA is a variant of tTA that is not functional in the absence of doxycycline but requires the presence of the ligand for transactivation. This tet system is therefore termed tet-ON. The tet systems have been used in vivo for the inducible expression of several transgenes, encoding, e.g., reporter genes, oncogenes, or proteins involved in a signaling cascade.

The Cre/lox system uses the Cre recombinase, which catalyzes site-specific recombination by crossover between two distant Cre recognition sequences, i.e., loxP sites. A DNA sequence introduced between the two loxP sequences (termed floxed DNA) is excised by Cre-mediated recombination. Control of Cre expression in a transgenic animal, using either spatial control (with a tissue- or cell-specific promoter) or temporal control (with an inducible system), results in control of DNA excision between the two loxP sites. One application is for conditional gene inactivation (conditional knockout). Another approach is for protein overexpression, wherein a floxed stop codon is inserted between the promoter sequence and the DNA of interest. Genetically modified animals do not express the transgene until Cre is expressed, leading to excision of the floxed stop codon. This system has been applied to tissue-specific oncogenesis and controlled antigene receptor expression in B lymphocytes. Inducible Cre recombinases have also been developed. The inducible Cre recombinase is activated only by administration of an exogenous ligand. The inducible Cre recombinases are fusion proteins containing the original Cre recombinase and a specific ligand-binding domain. The functional activity of the Cre recombinase is dependent on an external ligand that is able to bind to this specific domain in the fusion protein.

Embodiments include an in vitro cell, an in vivo cell, and a genetically modified animal such as a livestock animal that comprise a gene under control of an inducible system. The genetic modification of an animal may be genomic or mosaic. The inducible system may be, for instance, selected from the group consisting of Tet-On, Tet-Off, Cre-lox, and Hiflalpha. An embodiment is a gene set forth herein.

Dominant Negatives

Genes may thus be disrupted not only by removal or RNAi suppression but also by creation/expression of a dominant negative variant of a protein which has inhibitory effects on the normal function of that gene product. The expression of a dominant negative (DN) gene can result in an altered phenotype, exerted by a) a titration effect; the DN PASSIVELY competes with an endogenous gene product for either a cooperative factor or the normal target of the endogenous gene without elaborating the same activity, b) a poison pill (or monkey wrench) effect wherein the dominant negative gene product ACTIVELY interferes with a process required for normal gene function, c) a feedback effect, wherein the DN ACTIVELY stimulates a negative regulator of the gene function.

Founder Animals, Animal Lines, Traits, and Reproduction

Founder animals (F0 generation) may be produced by cloning and other methods described herein. The founders can be homozygous for a genetic modification, as in the case where a zygote or a primary cell undergoes a homozygous modification. Similarly, founders can also be made that are heterozygous. The founders may be genomically modified, meaning that the cells in their genome have undergone modification. Founders can be mosaic for a modification, as may happen when vectors are introduced into one of a plurality of cells in an embryo, typically at a blastocyst stage. Progeny of mosaic animals may be tested to identify progeny that are genomically modified. An animal line is established when a pool of animals has been created that can be reproduced sexually or by assisted reproductive techniques, with heterogeneous or homozygous progeny consistently expressing the modification.

In livestock, many alleles are known to be linked to various traits such as production traits, type traits, workability traits, and other functional traits. Artisans are accustomed to monitoring and quantifying these traits, e.g., Visscher et al., Livestock Production Science, 40:123-137, 1994, U.S. Pat. No. 7,709,206, US 2001/0016315, US 2011/0023140, and US 2005/0153317. An animal line may include a trait chosen from a trait in the group consisting of a production trait, a type trait, a workability trait, a fertility trait, a mothering trait, and a disease resistance trait. Further traits include expression of a recombinant gene product.

Recombinases

Embodiments of the invention include administration of a targeted nuclease system with a recombinase (e.g., a RecA protein, a Rad51) or other DNA-binding protein associated with DNA recombination. A recombinase forms a filament with a nucleic acid fragment and, in effect, searches cellular DNA to find a DNA sequence substantially homologous to the sequence. For instance, a recombinase may be combined with a nucleic acid sequence that serves as a template for HDR. The recombinase is then combined with the HDR template to form a filament and placed into the cell. The recombinase and/or HDR template that combines with the recombinase may be placed in the cell or embryo as a protein, an mRNA, or with a vector that encodes the recombinase. The disclosure of US 2011/0059160 (U.S. patent application Ser. No. 12/869,232) is hereby incorporated herein by reference for all purposes; in case of conflict, the specification is controlling. The term recombinase refers to a genetic recombination enzyme that enzymatically catalyzes, in a cell, the joining of relatively short pieces of DNA between two relatively longer DNA strands. Recombinases include Cre recombinase, Hin recombinase, RecA, RAD51, Cre, and FLP. Cre recombinase is a Type I topoisomerase from P1 bacteriophage that catalyzes site-specific recombination of DNA between loxP sites. Hin recombinase is a 21 kD protein composed of 198 amino acids that is found in the bacteria *Salmonella*. Hin belongs to the serine recombinase family of DNA invertases in which it relies on the active site serine to initiate DNA cleavage and recombination. RAD51 is a human gene. The protein encoded by this gene is a member of the RAD51 protein family which assists in repair of DNA double strand breaks. RAD51 family members are homologous to the bacterial RecA and yeast Rad51. Cre recombinase is an enzyme that is used in experiments to delete specific sequences that are flanked by loxP sites. FLP refers to Flippase recombination enzyme (FLP or Flp) derived from the 2p plasmid of the baker's yeast *Saccharomyces cerevisiae*.

Herein, "RecA" or "RecA protein" refers to a family of RecA-like recombination proteins having essentially all or most of the same functions, particularly: (i) the ability to position properly oligonucleotides or polynucleotides on their homologous targets for subsequent extension by DNA polymerases; (ii) the ability topologically to prepare duplex nucleic acid for DNA synthesis; and, (iii) the ability of RecA/oligonucleotide or RecA/polynucleotide complexes efficiently to find and bind to complementary sequences. The best characterized RecA protein is from *E. coli*; in addition to the original allelic form of the protein a number of mutant RecA-like proteins have been identified, for example, RecA803. Further, many organisms have RecA-like strand-transfer proteins including, for example, yeast, *Drosophila*, mammals including humans, and plants. These proteins include, for example, Rec1, Rec2, Rad51, Rad51B, Rad51C, Rad51D, Rad51E, XRCC2 and DMC1. An embodiment of the recombination protein is the RecA protein of *E. coli*. Alternatively, the RecA protein can be the mutant RecA-803 protein of *E. coli*, a RecA protein from another bacterial source or a homologous recombination protein from another organism.

Compositions and Kits

The present invention also provides compositions and kits containing, for example, nucleic acid molecules encoding site-specific endonucleases, CRISPR, Cas9, ZNFs, TALENs, RecA-gal4 fusions, polypeptides of the same, compositions containing such nucleic acid molecules or polypeptides, or engineered cell lines. An HDR may also be provided that is effective for introgression of an indicated allele. Such items can be used, for example, as research tools, or therapeutically.

EXAMPLES

Methods are as follows unless otherwise noted.
Tissue Culture and Transfection.

Pig were maintained at 37 at 5% $CO_2$ in DMEM supplemented with 10% fetal bovine serum, 100 I.U./ml penicillin and streptomycin, and 2 mM L-Glutamine. For transfection, all TALENs and HDR templates were delivered through transfection using the NEON Transfection system (Life Technologies). Briefly, low passage Ossabaw, Landrace reaching 100% confluence were split 1:2 and harvested the next day at 70-80% confluence. Each transfection was comprised of 500,000-600,000 cells resuspended in buffer "R" mixed with TALEN mRNA and oligos and electroporated using the 100 µl tips that provide a 100 µl working_volume by the following parameters: input Voltage; 1800V; Pulse Width; 20 ms; and Pulse Number; 1. Typically, 1-2 µg of TALEN mRNA and 1-4 µM of HDR templates (single stranded oligonucleotides) specific for the gene of interest were included in each transfection. Deviation from those amounts is indicated in the figures and legends. After transfection, cells were plated in a well of a 6-well dish for three days and cultured at either 30° C. After three days, cell populations were plated for colony analysis and/or expanded and at 37° C. until at least day 10 to assess stability of edits.
Surveyor Mutation Detection and RFLP Analysis.

PCR flanking the intended sites was conducted using PLATINUM Taq DNA polymerase HiFi (Life Technologies) with 1 µl of the cell lysate according to the manufacturer's recommendations. The frequency of mutation in a population was analysed with the SURVEYOR Mutation Detection Kit (Transgenomic) according to the manufacturer's recommendations using 10 µl of the PCR product as described above. RFLP analysis was performed on 10 µl of the above PCR reaction using the indicated restriction enzyme. Surveyor and RFLP reactions were resolved on a 10% TBE polyacrylamide gels and visualized by ethidium bromide staining. Densitometry measurements of the bands were performed using IMAGEJ; and mutation rate of Surveyor reactions was calculated as described in Guschin et al., 2010(1). Percent homology directed repair (HDR) was calculated by dividing the sum intensity of RFLP fragments by the sum intensity of the parental band+RFLP fragments. RFLP analysis of colonies was treated similarly except that the PCR products were amplified by 1× MYTAQ RED MIX (Bioline) and resolved on 2.5% agarose gels.
Dilution Cloning:

Three days post transfection, 50 to 250 cells were seeded onto 10 cm dishes and cultured until individual colonies reached circa 5 mm in diameter. At this point, 6 ml of TRYPLE (Life Technologies) 1:5 (vol/vol) diluted in PBS was added and colonies were aspirated, transferred into wells of a 24-well dish well and cultured under the same conditions. Colonies reaching confluence were collected and divided for cryopreservation and genotyping.
Sample Preparation:

Transfected cells populations at day 3 and 10 were collected from a well of a 6-well dish and 10-30% were resuspended in 50 µl of 1× PCR compatible lysis buffer: 10 mM Tris-Cl pH 8.0, 2 mM EDTA, 0.45% TRYTON X-100 (vol/vol), 0.45% TWEEN-20(vol/vol) freshly supplemented with 200 µg/ml Proteinase K. The lysates were processed in a thermal cycler using the following program: 55° C. for 60 minutes, 95° C. for 15 minutes. Colony samples from dilution cloning were treated as above using 20-30 µl of lysis buffer.

TABLE D

Listing of Endonuclease binding sequences and HDR templates.

| Gene | Example | Endonuclease | HDR Template |
|---|---|---|---|
| Example | | L: repeat-variable diresidue (RVD) code for left TALEN monomer<br>R: RVD code for right TALEN monomer<br>OR<br>Cas9/CRISPR, sgRNA:<br>gRNA sequence, 5' to 3' | ssDNA oligo sequence, 5' to 3' |

TABLE D-continued

Listing of Endonuclease binding sequences and HDR templates.

| Gene | Example | Endonuclease | HDR Template |
|---|---|---|---|
| IL2Rγ | 1, 3 | L: HD HD HD NI NI NI NN NN NG NG HD NI NN NG NN NG NG NG (SEQ ID NO: 4) R: HD HD NI NI NN NG NN HD NI NI NG NG HD NI NG NN NG NI HD NG (SEQ ID NO: 5) | TTCCACTCTACCCCCCCAAAGG TTCAGTGTTTTGTGTAAGCTTCAA TGTTGAGTACATGAATTGCACTT GGGACAGCAGCTCTGAGCTC (SEQ ID NO: 27) |
| RAG2 | 1, 3 | L: NI HD HD NG NG HD HD NG HD HD NG HD NG HD HD NN HD NG (SEQ ID NO: 6) R: HD NG NI NI NN HD NG NN HD NG NG NG NN NI NI NG (SEQ ID NO: 7) | CTCTAAGGATTCCTGCCACCTTCC TCCTCTCCGCTACCCAGACTAAG CTTTGCACATTCAAAAGCAGCTT AGGGTCTGAAAAACATCAGT (SEQ ID NO: 28) |
| APC | 2, 3 | L: NN NN NI NI NN NI NI NN NG NI NG HD NI NN HD HD NI NG (SEQ ID NO: 8) R: NN NI HD HD HD NI NN NI NI NG NG HD NG NN NG (SEQ ID NO: 9) | CCAGATCGCCAAAGTCACGGAAG AAGTATCAGCCATTCATCCCTCC CAGTGAAGCTTACAGAAATTCTG GGTCGACCACGGAGTTGCACT (SEQ ID NO: 29) |
| P53 | 2, 3 | L: NN NN HD NI HD HD HD NN NG NN HD HD NN HD NN HD (SEQ ID NO: 10) R: HD NI NG NN NG NI HD NG HD NG NN NI HD NG NG (SEQ ID NO: 11) | AGCTCGCCACCCCGCCGGGCAC CCGTGTCCGCGCCATGGCCATCT AAGCTTAAAGAAGTCAGAGTACA TGCCCGAGGTGGTGAGGCGCT (SEQ ID NO: 30) |
| KISSR | 3 | L: NN HD NG HD NG NI HD NG HD NG NI HD HD HD HD (SEQ ID NO: 12) R: NN HD NI HD NG NI NG NN NI NI NN NG HD NN HD HD HD NI (SEQ ID NO: 13) | GTGCTGCGTGCCCTTTACTGCTCT ACTCTACCCCTACCAGCCTAAG CTTGTGCTGGGCGACTTCATGTG CAAGTTCCTCAACTACATCC (SEQ ID NO: 31) |
| EIF4GI | 3, 7 | L: HD HD NN NG HD HD NG NG NG NN HD HD NI NI HD HD NG NG (SEQ ID NO: 14) R: NG NN NN NN NN NN HD HD HD NI HD NN NN NG NG NN HD NG (SEQ ID NO: 15) | CCCAGACTTCACTCCGTCCTTTGC CGACTTCGGCCGACCAGCCCTTA GCAACCGTGGGCCCCAAGGGGT GGGCCAGGTGGGGAGCTGCC (SEQ ID NO: 32) |
| LDLR | 3 | L: HD NG HD HD NG NI HD NI NI NN NG NN NN NI NG NG NG (SEQ ID NO: 16) R: HD NN NN NI HD HD HD NN NG HD HD NG NG NN HD NI HD NG (SEQ ID NO: 17) | CCGAGACGGGAAATGCACCTCCT ACAAGTGGATTTGTGATGGATCC GAACACCGAGTGCAAGGACGGG TCCGCTGAGTCCCTGGAGACGT (SEQ ID NO: 33) |
| DMD | 3 | L: NN NN NI HD NG NN NI HD HD NI HD NG NI NG NG (SEQ ID NO: 18) R: NI NN NI NN NI NI NG NN NG NN NN NG HD HD NI NN HD (SEQ ID NO: 19) | AAAGTGGCCTGGCCCAACCCCTG GACTGACCACTCGAGTATTGAAG CACGTAAGTATGCTGGACCACAT TCTCTATGGCTGTAGACATTC (SEQ ID NO: 34) |
| NKX2-5 | 6 | L: HD NN HD NI NN NN HD NI HD NI NN NN NG HD NG NI HD (SEQ ID NO: 20) R: NI HD HD NN HD NG NN HD NG NN HD NG NG NN NI (SEQ ID NO: 21) | CTCTTTTCGCAGGCACAGGTCTA CGAGCTGGAGCGACGCTTCTAAG CTTGCAGCAGCGGTACCTGTCGG CTCCCGAGCGTGACCAGTTGG (SEQ ID NO: 35) |
| MESP1 | 6 | L: NN HD NN NN NG NG NN HD NG HD HD HD HD NN HD HD (SEQ ID NO: 22) R: NN NN HD HD NN NN NN NN HD NN NN HD NN NI HD HD (SEQ ID NO: 23) | TGCGGTTGCTCCCCGCCTCGTCC CCGTAAGCTTGACTCCTGGTGCA GCGCCCCGGCCAG (SEQ ID NO: 36) |
| GATA4 | 6 | L: NI NG NN NG NG NG NN NI NG NN NI HD NG NG HD (SEQ ID NO: 24) | AACCCTGTGTCGTTTCCCACCCA GTAGATATGTTTGATGACTAAGC TTCTCGGAAGGCAGAGAGTGTGT |

TABLE D-continued

Listing of Endonuclease binding sequences and HDR templates.

| Gene | Example | Endonuclease | HDR Template |
|---|---|---|---|
| | | R: NN NN HD HD HD NN HD NI NN NG NG NN NI HD NI HD (SEQ ID NO: 25) | CAACTGCGGGGCCATGTCCAC (SEQ ID NO: 37) |
| P65 | 7 | Cas9/CRISPR, sgRNA: CGTCACCAACGGTCTCCTC TCGG (SEQ ID NO: 26) | GCTCCCACTCCCCTGGGGGCCTC TGGGCTCACCAACGGTCTCCTCC CGGGGGACGAAGACTTCTCCTCC ATTGCGGACATGGACTTCTCA (SEQ ID NO: 38) |

Example 1 Multiplex Gene Editing

Six conditions of TALEN mRNA and HIDR templates directed to pig RAG2 and IL2Rγ were co-transfected into pig fibroblasts. A fixed quantity of RAG2 mRNA and template were used for each transfection whereas the quantity of IL2Rg TALEN mRNA and HIDR template is altered for each condition as indicated. The dosage of TALEN mRNA and HIDR template has both on and off target effects. An increase in TALEN mRNA for IL2Rγ led to an increase in both NHEJ and HIDR for IL2Rγ while NHEJ levels for RAG2 were unchanged. An increase in IL2Rγ HIDR template reduced HIDR at the RAG2 locus suggesting a non-specific inhibition of homology directed repair by escalation of the concentration of oligonucleotide. Colonies with bi-allelic HIDR at RAG2 and IL2Rγ were obtained at four and two percent from two conditions (FIG. 3 panel, c, panel d) which is at and above the expected frequency of two percent. The expected frequency is calculated by multiplication of day 3 HIDR levels which treats each HDR allele as an independent event. Referring to FIG. 3, Multiplex gene editing of swine RAG2 and IL2Rγ. a). SURVEYOR and RFLP analysis to determine the efficiency of non-homologous end joining (NHEJ) and homology depended repair HIDR on cell populations 3 days post transfection. b). RFLP analysis for homology dependent repair on cell populations 11 days post transfection. c). Percentage of colonies positive for HDR at IL2Rγ, RAG2 or both. Cells were plated from the population indicated by a "C" in panel a. Distribution of colony genotypes is shown below. d). Colony analysis from cells transfected with TALEN mRNA quantities of 2 and 1 µg for IL2Rγ and RAG2 and HDR template at 1 µM for each. Distribution of colony genotypes is shown below.

Example 2 Multiplex Gene Editing

Four conditions of TALEN mRNA and HDR templates directed to pig APC and p53 were co-transfected into pig fibroblasts. The quantity of APC mRNA was sequentially reduced from left to right (FIG. 4 panel b); the remaining of the quantities remained constant as indicated. Percent HDR reduced in a linear manor with reduction of APC mRNA. There was little effect on p53 HDR with altered dosage of APC TALENs. Genotyping of colonies revealed a higher than expected union of clones with HDR allele in both APC and p53 relative to the day 11 values; 18 and 20 percent versus 13.7 and 7.1 percent for FIG. 4 panel c and FIG. 4 panel d, respectively. Referring to FIG. 4 Multiplex gene editing of swine APC and p53. Panel a). Surveyor and RFLP analysis to determine the efficiency of non-homologous end joining (NHEJ) and homology depended repair HDR on cell populations 3 days post transfection. Panel b). RFLP analysis for homology dependent repair on cell populations 11 days post transfection. Panels c) and d). Percentage of colonies positive derived from the indicated cell population (indicated in panel a, "C" and "D") for HDR at APC, p53 or both. Colonies with 3 or more HDR alleles are listed below.

Example 3 Multiplex with at Least Three Genes

Figure 6:
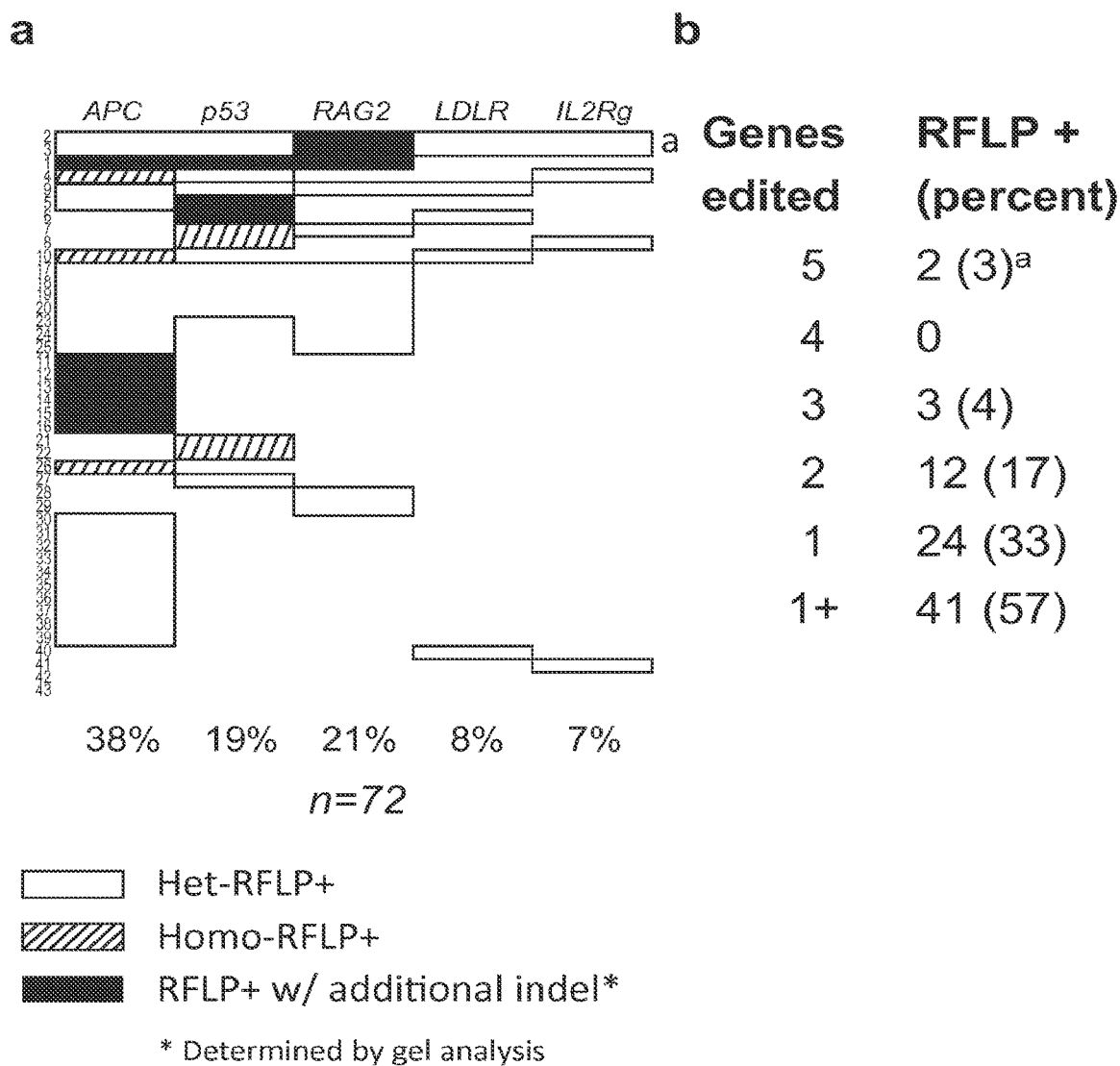
FIG. 6 is a five-gene multiplex data set that shows plots of experimental data for the effect of oligonucleotide HDR template concentration on 5-gene multiplex HDR efficiency. Indicated amounts of TALEN mRNA directed to swine RAG2, IL2Rg, p53, APC and LDLR were co-transfected into pig fibroblasts along with 2 μM (panel a) or 1 μM (panel b) of each cognate HDR template. Percent NHEJ and HDR were measured by Surveyor and RFLP assay. Colony genotypes from 5-gene multiplex HDR: Colony genotypes were evaluated by RFLP analysis. Panel a) Each line represents the genotype of one colony at each specified locus. Three genotypes could be identified; those with the expected RFLP genotype of heterozygous or homozygous HDR as well as those with an RFLP positive fragment, plus a second allele that has a visible shift in size indicative of an insertion or deletion (indel) allele. The percentage of colonies with an edit at the specified locus is indicated below each column. Panel b) A tally of the number of colonies edited at 0-5 loci.
Figure 7:
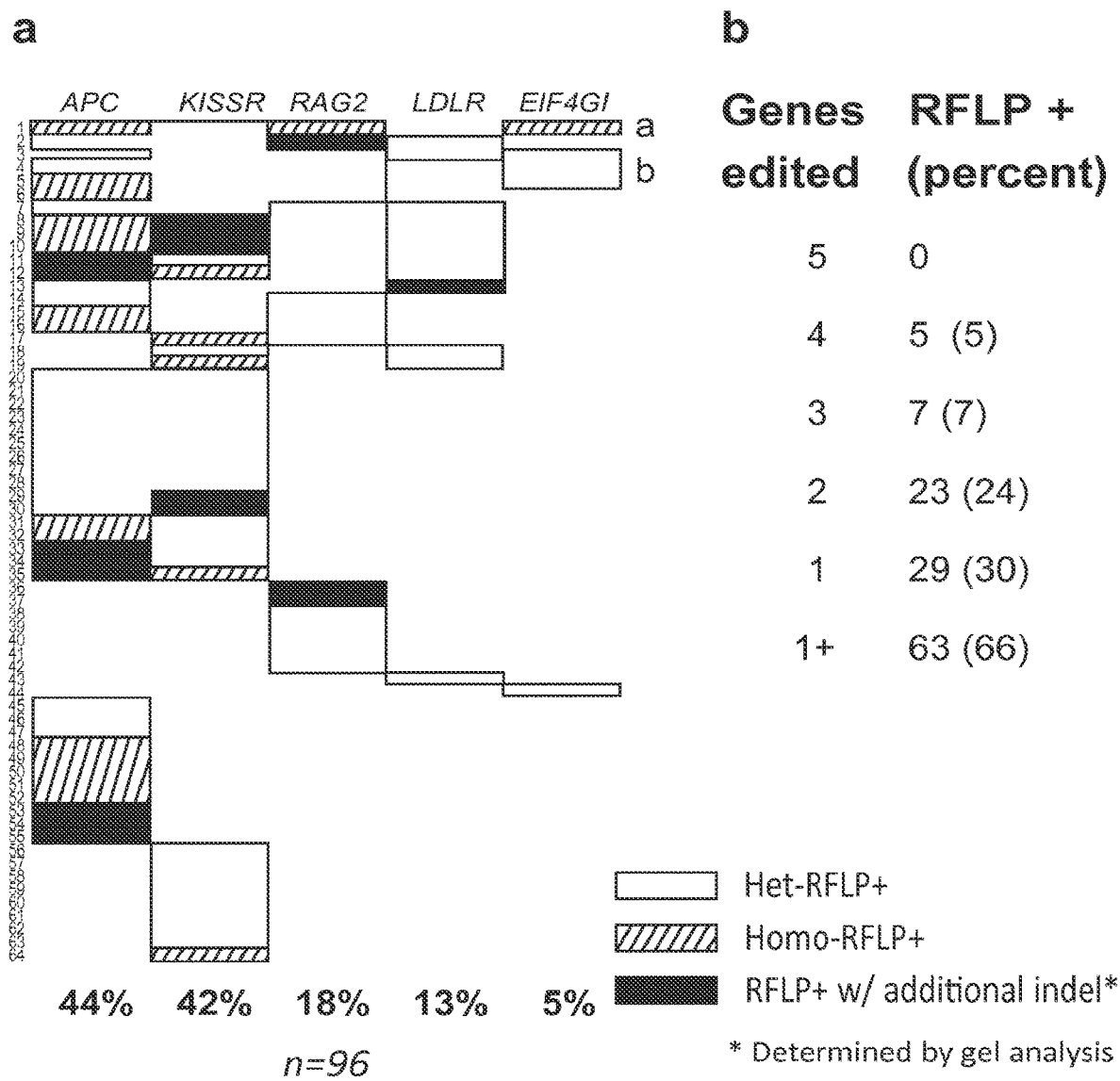
FIG. 7 is another five-gene multiplex data set that shows plots of experimental data for a second experiment involving the effect of oligonucleotide HDR template concentration on Five-gene multiplex HDR efficiency. Colony genotypes of a second 5-gene multiplex trial. Panel a) Each line represents the genotype of one colony at each specified locus. Three genotypes could be identified; those with the expected RFLP genotype of heterozygous or homozygous HDR as well as those with an RFLP positive fragment, plus a second allele that has a visible shift in size indicative of an insertion or deletion (indel) allele. The percentage of colonies with an edit at the specified locus is indicated below each column. Panel b) A tally of the number of colonies edited at 0-5 loci.
Figure 8:
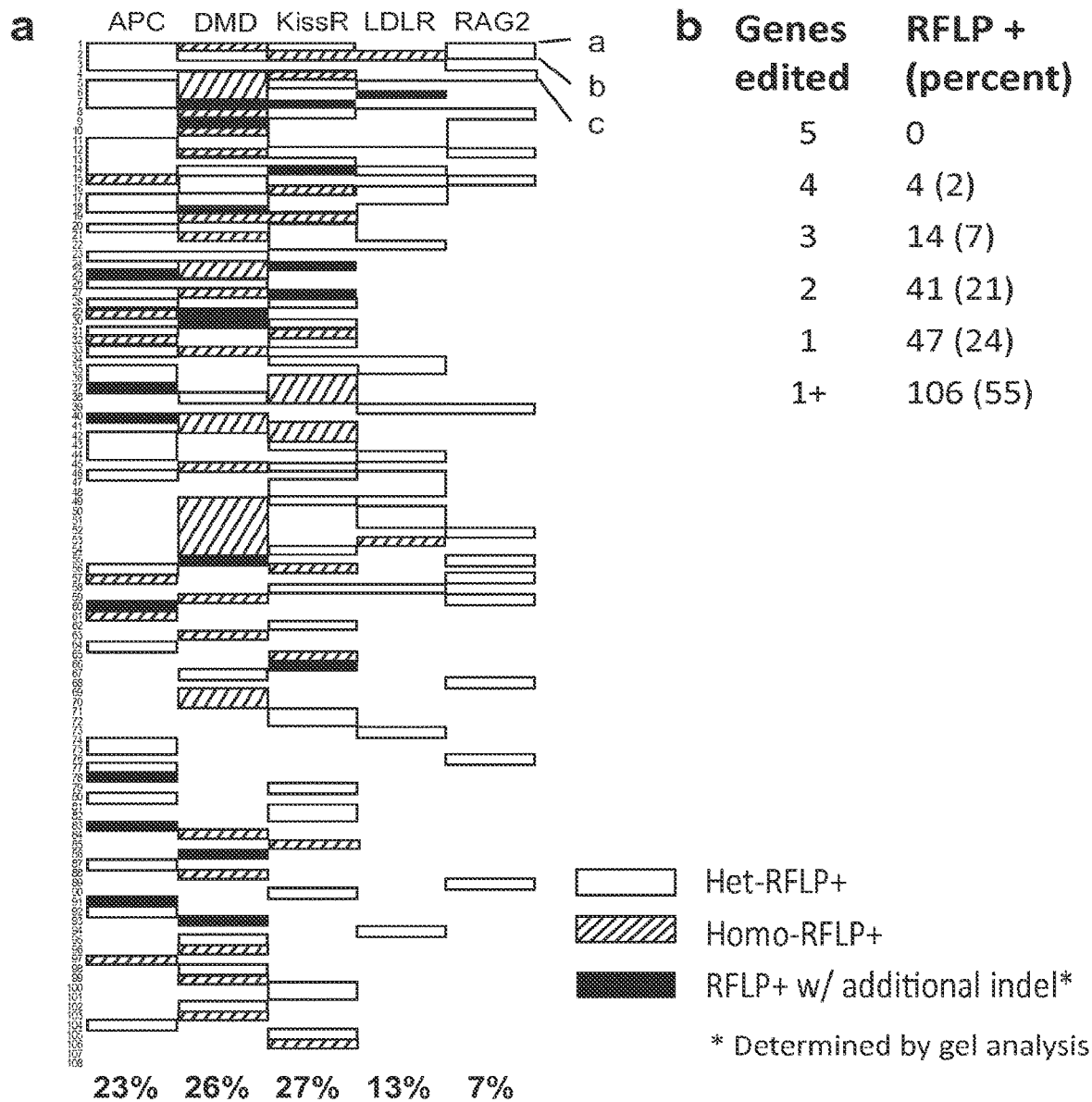
FIG. 8 is another five-gene multiplex trial data set that shows colony genotypes. Panel a) Each line represents the genotype of one colony at each specified locus. Three genotypes could be identified; those with the expected RFLP genotype of heterozygous or homozygous HDR as well as those with an RFLP positive fragment, plus a second allele that has a visible shift in size indicative of an insertion or deletion (indel) allele. The percentage of colonies with an edit at the specified locus is indicated below each column. Panel b) A tally of the number of colonies edited at 0-5 loci.

In Example 1, a non-specific reduction in HDR was observed at high concentration of HDR oligo, thus it was unknown whether 2+ HDR oligos could be effective without non-specific inhibition of HDR. Two concentrations were tested, 1 µM and 2 µM for each target site. While TALEN activity was not significantly altered between the two conditions, HDR was blunted significantly at 2 µM concentration for each template. Clones derived from the 1 µM condition had a variety of genotypes, some of those with edits in each gene and up to 7 alleles (FIG. 6). If treated as independent events, the expected frequency of the genotype denoted by an "a", with 7 alleles edited, is 0.001 percent. Binomial distribution predicts the likelihood of identifying 2+ colonies of such a genotype in a sample size of 72, as was done here, is less than 0.000026 percent. This high rate of success could not be predicted and is unexpected and surprising. This result was replicated with two addition combinations of TALENs/HDR template (FIGS. 7 and 8). As with the results the first trial, colonies were obtained with HDR edits in up to seven alleles and up to four genes (Table A). Several genotypes were recovered at a frequency far greater than anticipated by chance. Although a concern regarding simultaneous double strand break at several loci is induction of unintended chromosomal rearrangements, 50 of 50 karyotypes tested from trial 3 cells were normal (data not shown).

Figure 5:
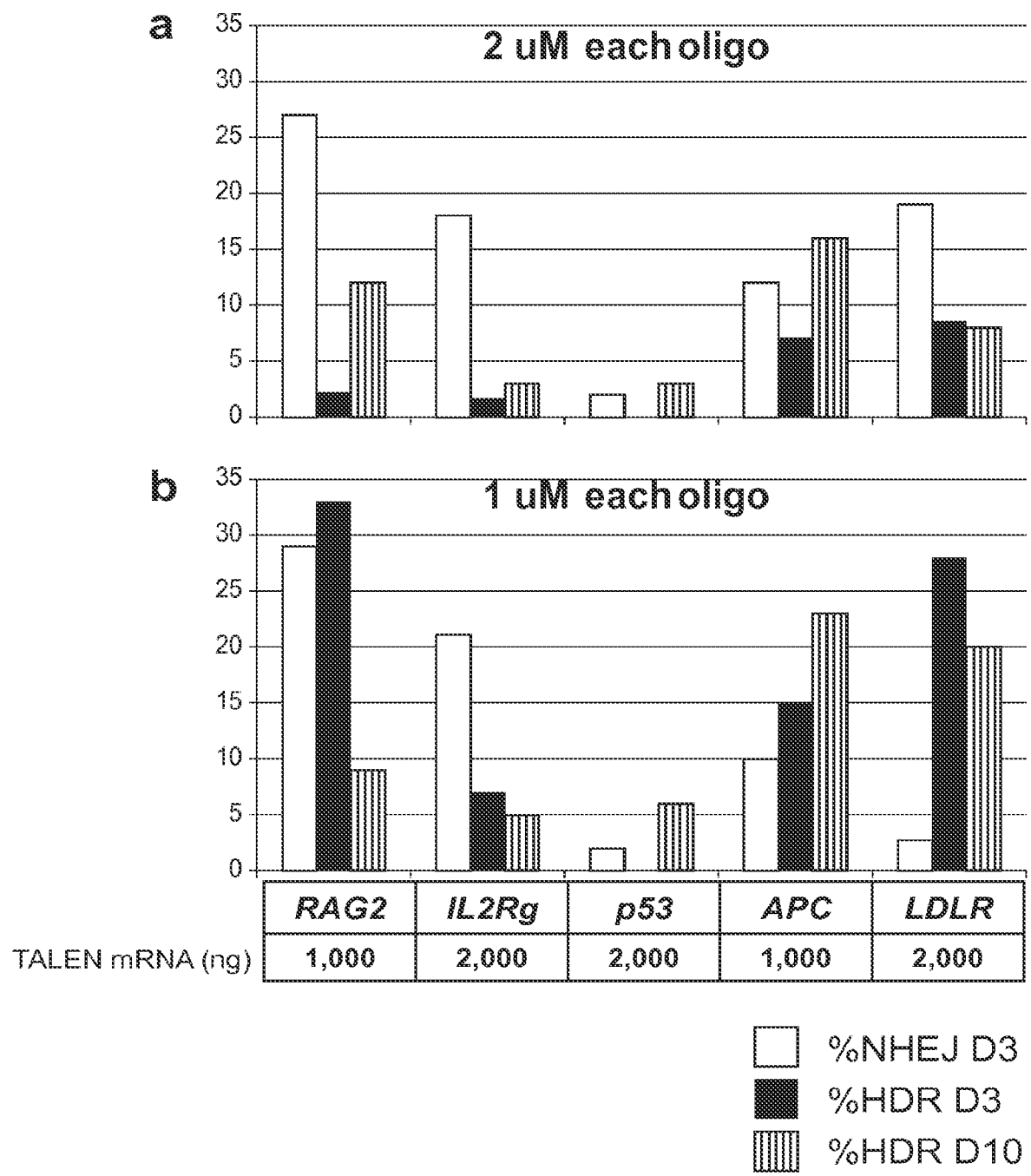
FIG. 5 Effect of Oligonucleotide HDR template concentration on Five-gene multiplex HDR efficiency. Indicated amounts of TALEN mRNA directed to swine RAG2, IL2Rg, p53, APC and LDLR were co-transfected into pig fibroblasts along with 2 μM (panel a) or 1 μM (panel b) of each cognate HDR template. Percent NHEJ and HDR were measured by Surveyor and RFLP assay.

Referring to FIG. 5: Effect of Oligonucleotide HDR template concentration on 5-gene multiplex HDR efficiency. Indicated amounts of TALEN mRNA directed to swine RAG2, IL2Rg, p53, APC and LDLR were co-transfected into pig fibroblasts along with 2 µM (panel a) or 1 µM (panel b) of each cognate HDR template. Percent NHEJ and HDR were measured by Surveyor and RFLP assay. Referring to FIG. 6: Colony genotypes from 5-gene multiplex HDR. Colony genotypes were evaluated by RFLP analysis. Panel a) Each line represents the genotype of one colony at each specified locus. Three genotypes could be identified; those with the expected RFLP genotype of heterozygous or homozygous HDR as well as those with an RFLP positive fragment, plus a second allele that has a visible shift in size indicative of an insertion or deletion (indel) allele. The percentage of colonies with an edit at the specified locus is indicated below each column. Panel b) A tally of the number of colonies edited at 0-5 loci. Referring to FIG. 7: Colony genotypes of a second 5-gene multiplex trial. Panel a) Each line represents the genotype of one colony at each specified locus. Three genotypes could be identified; those with the expected RFLP genotype of heterozygous or homozygous HDR as well as those with an RFLP positive fragment, plus a second allele that has a visible shift in size indicative of an insertion or deletion (indel) allele. The percentage of colonies with an edit at the specified locus is indicated below each column. Panel b) A tally of the number of colonies edited at 0-5 loci. Referring to FIG. 8: Colony genotypes a third 5-gene multiplex trial. Panel a) Each line represents the genotype of one colony at each specified locus. Three genotypes could be identified; those with the expected RFLP genotype of heterozygous or homozygous HDR as well as those with an RFLP positive fragment, plus a second allele that has a visible shift in size indicative of an insertion or deletion (indel) allele. The percentage of colonies with an edit at the specified locus is indicated below each column. Panel b) A tally of the number of colonies edited at 0-5 loci.

Examples 4A-4DD

Example 4A: Develop RAG2/IL2Rg Null (RG-KO) Pig Fibroblasts by Multiplex Gene Editing Male pig fetal fibroblasts will be transfected with TAL-ENs and oligonucleotide templates for disruption of RAG2 and IL2Rg using the inventors' previously defined methods (Tan, W., et al., Efficient nonmeiotic allele introgression in livestock using custom endonucleases. PNAS, 110(41): 16526-16531, 2013.) RG-KO candidates will be identified by, e.g., restriction length polymorphism (RFLP) as confirmed by sequencing. At least about 5 validated RG-KO colonies will be pooled as a resource for cloning and chimera production.

Example 4B: Production of Chimeric Embryos Using RG-KO Host Blastocysts

Host RG-KO embryos and female EGFP-labeled donor cells will be produced using chromatin transfer technology followed by in vitro culture to the blastocyst stage. RG-KO cells from Example 1 may be used. Day-7 inter cell mass clumps from EGFP blastocysts will be injected into day-6 RG-KO embryos prior to embryo transfer to a synchronized sow. Using this approach, Nagashima and colleagues observed chimerism in >50 percent of liveborn piglets (Nagashima, H., et al., Sex differentiation and germ cell production in chimeric pigs produced by inner cell mass injection into blastocysts. Biol Reprod, 70(3):702-707, 2004). The male phenotype is dominant in injection chimeras for both mice and pigs. Therefore, XY RG-KO hosts injected with female donor cells will exclusively transmit male host genetics. Pregnancy checks will be conducted at appropriate times, e.g., days 25, 50, and 100. Pregnant sows at about 100 days of gestation will be monitored 4 times daily prior to C-section derivation of piglets by about day 114.

Example 4C: Determine if Non-Chimeric Offspring are Deficient for T, B and NK Cells Non-chimeric offspring will be tested to determine if they deficient for T, B and NK cells. The following process is one technique for the same. C-section derivation will be conducted on each sow carrying presumptive chimeras and one bred sow carrying wild-type piglets. Umbilical cord blood will be isolated from each piglet immediately after C-section derivation. Cord blood leukocytes will be evaluated by fluorescence-activated cell sorting (FACS) for T, B and NK cell populations as well as donor derived EGFP expression. In addition, chimerism will be evaluated by PCR from cord blood, ear and tail biopsy. This initial analysis will be completed within 6 hours of birth, such that non-chimeric piglets can be monitored closely and humanely euthanized with signs of infection. A portion of non-chimeric animals, or those lacking immune cells, will be euthanized for necropsy.

Example 4D: Identify Chimeric Pigs and Determine Origin of T, B and NK Cells

Chimeric pigs will be tested to determine origin of T, B and NK cells. The following process is one technique for the same. Chimeric piglets will be identified using the methods above. Weekly evaluation of circulating lymphocytes and serum immunoglobulin will be compared between chimeric, non-chimeric and wild-type piglets over a 2-month period. Populations of sorted T, B and NK cells will be evaluated for EGFP expression and microsatellite analysis to confirm donor origin. The maintenance of samples and semen collections from chimeric pigs will be supported by RCI until Phase II funding is available.

Sample Procedures for Examples A-D:

Cord and Peripheral Blood FACS.

Evaluation of blood lymphocytes and EGFP chimerism will be performed as previously described (2) with adaptations for porcine specimens. Cord blood will be collected from each piglet immediately after C-section delivery. A portion of the cord blood will be processed and cryopreserved for potential allograft treatments while the remainder will be used for FACS analysis of lymphocytes. Peripheral blood samples will be collected at 2, 4, 6 and 8 weeks of age by standard methods. RBCs will be removed and approximately 1-2E+5 cells will be distributed into tubes. Aliquots will be labeled with anti-pig antibodies for identification of T cells (CD4 and CD8), B cells (CD45RA ad CD3), NK cells (CD16 and CD3) and myeloid cells (CD3). Antigen expression will be quantified on the LS RII Flow Cytometer (BD Biosciences). Fluorophores will be carefully selected to enable multiplex evaluation of donor derived EGFP cells along with surface antigens. Single cell suspensions from the spleen will be analyzed by the same methods.

Examinations

All major organs and tissues will be grossly examined for appropriate anatomic development and appropriate samples from all major organs and tissues including pancreas, liver, heart, kidneys, lungs, gastrointestinal, immune system (peripheral and mucosal lymph nodes and spleen), and CNS will be collected for DNA isolation. Single cell suspensions will be prepared from the spleen for FACS analysis. Tissues will be prepared for histological examination to further assess chimerism and for any alterations that may be associated with the chimeric state and for the presence of any underlying illness.

Assessment of Chimerism.

Quantitative PCR will be conducted on cord blood, ear, and tail biopsy using primers specific to the EGFP transgene and compared to a standard curve with known ratios of EGFP to wild type-cells. Specimens will also be evaluated for RG-KO alleles via the RFLP assay previously described. Engraftment of EGFP+ cells will be evaluated macroscopically on whole animals and organs during necropsy. Tissues from the major organs will be sectioned for EGFP immunohistochemistry and counterstained with DAPI (4', 6-diamidino-2-phenylindole) to determine the ratio of donor to host cells.

Microsatellite Analysis.

Animals will be screened for informative microsatellites for host and donor genetics from those routinely used in our lab. Samples from tissues and blood (sorted lymphocytes or myeloid lineages, EGFP positive and negative) will be evaluated. Relative quantities of donor versus host cells will be evaluated by multiplexed amplicon sequencing on the MISEQ instrument (Illumina).

Animals

Non-chimeric pigs will be made having an absence of T, B and NK cells in cord and peripheral blood. Chimeric pigs will have levels substantially similar to nearly wild-type levels. Moreover, T, B and NK cell positive chimeras will have substantially normal immune functions and remain healthy when reared in standard conditions.

Example 5 CRISPR/Cas9 Design and Production

Gene specific gRNA sequences were cloned into the Church lab gRNA vector (Addgene ID: 41824) according their methods. The Cas9 nuclease was provided either by co-transfection of the hCas9 plasmid (Addgene ID: 41815) or mRNA synthesized from RCIScript-hCas9. This RCIScript-hCas9 was constructed by sub-cloning the XbaI-AgeI fragment from the hCas9 plasmid (encompassing the hCas9 cDNA) into the RCIScript plasmid. Synthesis of mRNA was conducted as above except that linearization was performed using KpnI.

Example 6 Multiplex Gene Editing with Targeted Endonucleases and HDR

Figure 12:
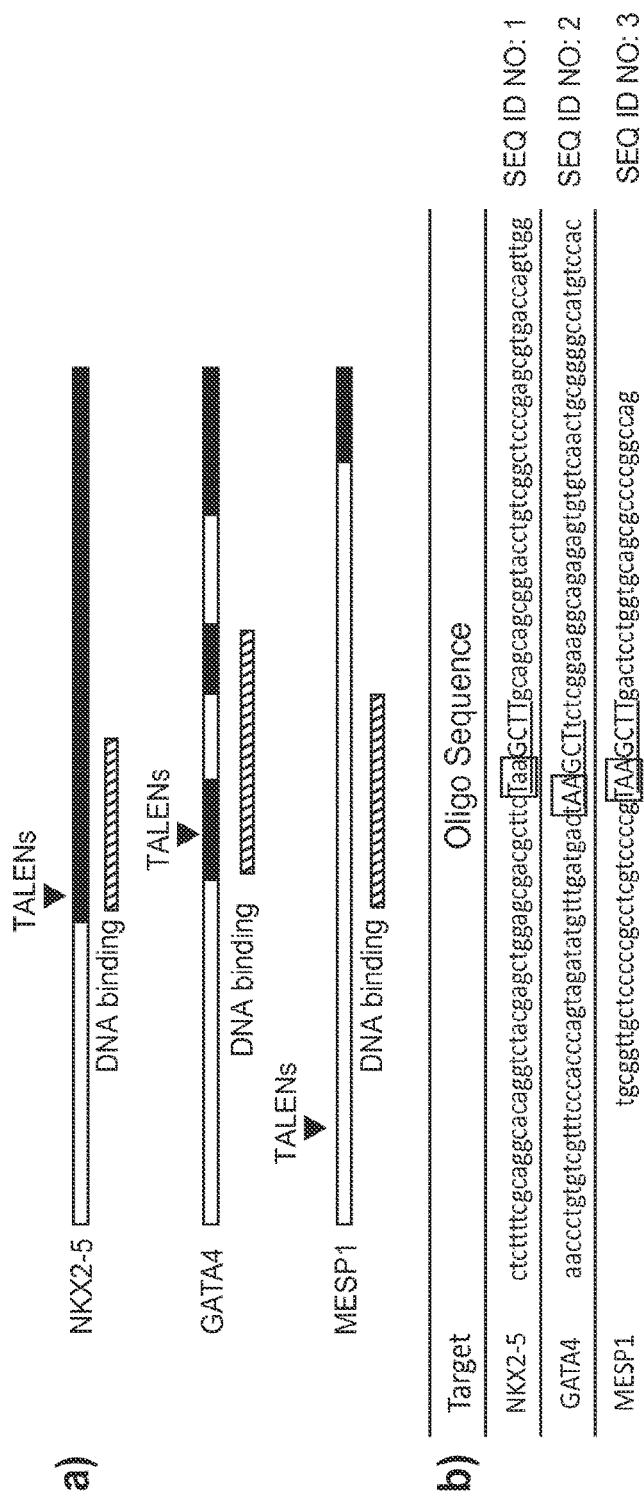
FIG. 12 depicts multiplex editing at three targeted loci of NKX-2, GATA4, and MESP1. Panel a) is a schematic of the experiment, panel b) shows the targeting of the genes, with the NKX2-5, GATA4, and MESP1 listed as SEQ ID NOs: 1-3, respectively. Panel c) depicts the results of an assay for the experiments. Oligo sequences for each target gene. Novel nucleotides are represented by capital letters. The PTC is represented by light color letters in boxes and the novel HindIII RFLP site is underlined.
Figure 12:
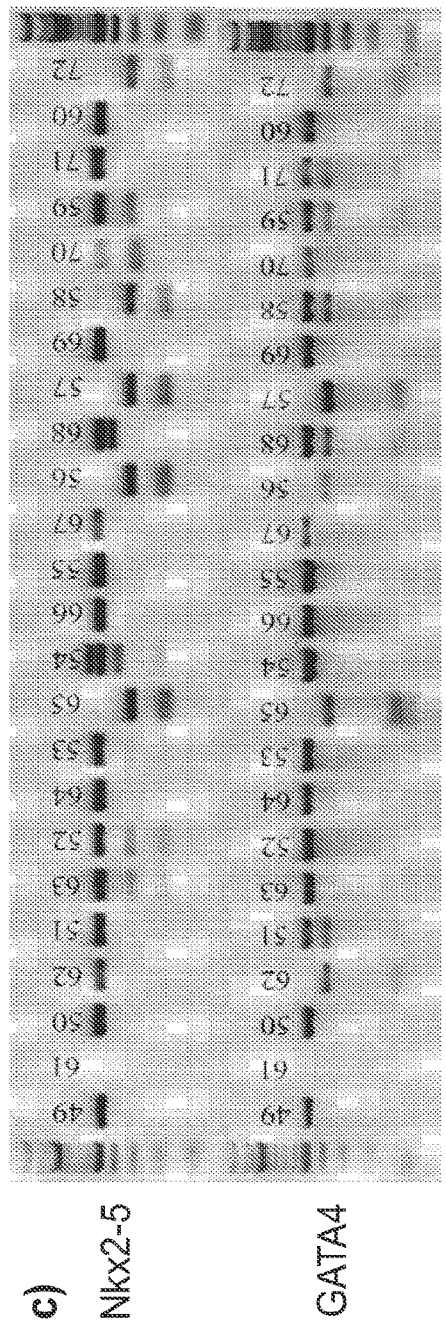

Panel (a) is a schematic of each gene in the multiplex experiment (depicted as a cDNA-exons denoted by alternating shades) and the site targeted by TALENS is indicated. The sequence coding the DNA binding domain for each gene is indicated below. Swine fibroblasts were co-transfected with 1 ug of each TALEN mRNA and 0.1 nMol of each HDR oligo (FIG. 12 panel b), targeting each gene, designed to insert a premature termination codon as well as a novel HindIII RFLP site for genotyping. A total of 384 colonies were isolated for genotyping. The GATA4 and Nkx2-5 RFLP assays were performed (FIG. 12 panel c) and MESP1 was evaluated by sequencing (not shown). Two colonies (2/384, 0.52%) were homozygous HDR knockouts for all three genes. The triple knockouts are labeled with asterisks (FIG. 12 panel c). Additional genotypes can be observed in panel c, example colony 49 with no HDR edits; colony 52 and 63 with heterozygous edits to NKX2-5; colony 59 with heterozygous edits to both NKX2-5 and GATA4 and so on.

Example 7. Multiplex Gene-Editing Using a Combination of TALENs and RGENs

Figure 13:
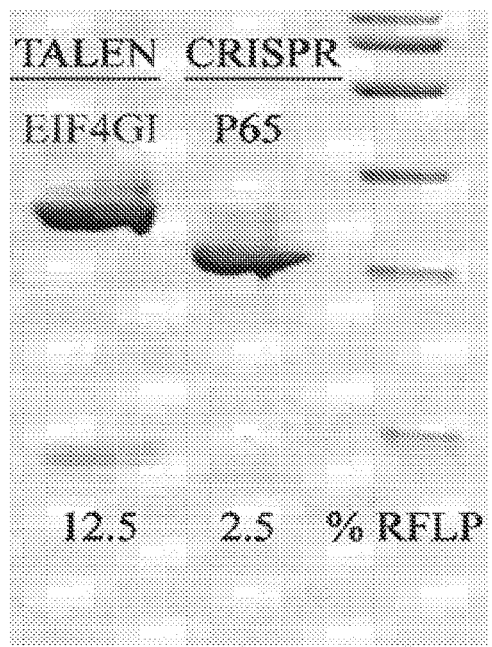
FIG. 13 depicts multiplex gene-editing using a combination of TALENs and RGENs; assay of transfected cells evaluated by RFLP revealed HDR at both sites.

See FIG. 13. Swine fibroblasts were co-transfected with TALENS (1 ug EIF4G 14.1 mRNA)+Cas9/CRISPR components (2 ug Cas9 mRNA+2 ug p65 Gis guide RNA) and 02 nMol of HDR oligo for each gene. Transfected cells were evaluated by RFLP assay revealing HDR at both sites. Cells from this population will be plated for colony isolation and isolates with edits in both genes are identified.

FURTHER DISCLOSURE

Patents, patent applications, publications, and articles mentioned herein are hereby incorporated by reference; in the case of conflict, the instant specification is controlling. The embodiments have various features; these features may be mixed and matched as guided by the need to make a functional embodiment. The headings and subheadings are provided for convenience but are not substantive and do not limit the scope of what is described. The following numbered statements present embodiments of the invention:

1A. A method of making genetic edits in a vertebrate cell or embryo at a plurality of target chromosomal DNA sites comprising introducing into a vertebrate cell or embryo:

a first targeted endonuclease directed to a first target chromosomal DNA site and a first homology directed repair (HDR) template homologous to the first target site sequence; and a second targeted endonuclease directed to a second target chromosomal DNA site and a second HDR template homologous to the second target site sequence, with the first HDR template sequence replacing the native chromosomal DNA sequence at the first target site and the second HDR template sequence replacing the native chromosomal DNA sequence at the second target site sequence.

1B. A method of editing a plurality of alleles of an animal, comprising introducing, into a primary livestock cell or livestock embryo, a plurality of targeted nucleases that each target a different allele locus and a homology directed repair template for each targeted allele locus, with the targeted endonucleases making double stranded breaks in the allele loci cognate to each of the plurality of targeted endonucleases and with the cell copying the homology directed repair (HDR) template nucleic acid sequence into the loci cognate to each HDR template to thereby edit the allele.

2. The method of any of 1 further comprising introducing into the cell or embryo one or more of:

a third, fourth, fifth, sixth, and seventh targeted endonuclease directed to a third, fourth, fifth, sixth, and seventh target chromosomal DNA site, respectively, and a third, fourth, fifth, sixth, and seventh HDR template homologous to the third, fourth, fifth, sixth, and seventh target chromosomal DNA sites, respectively.

3. The method of any of 1-2 wherein the targeted endonuclease comprises a TALENs.

4. The method of any of 1-3 wherein the targeted endonuclease comprises a zinc finger nuclease or a Cas9.

5. The method of any of 1-4 wherein at least the first target chromosomal DNA site is a locus for an allele.

6. The method of 5 wherein at least one of said HDR templates encodes a knockout of the DNA target site cognate to the template.

7. The method of 5 wherein at least one of said HDR templates encodes an exogenous allele for replacement of an allele at the DNA target site cognate to the template.

8. The method of 1 with the cell or embryo being a first species or a first breed of livestock, and a plurality of the edits comprise a replacement of a native allele with an exogenous allele from a second species or a second breed of animal.

9. The method of 1 with the animal being a first breed of animal that has at least three native alleles replaced with corresponding exogenous alleles of a second breed or another species, said exogenous alleles being a replacement of the corresponding native allele without meiotic recombination, wherein the animal is free of exogenous marker genes.

10. The method of 2 wherein at least three, four, five, six, or seven target chromosomal DNA sites are each a locus for a different allele.

11. The method of 10 wherein one or more of the HDR templates encodes a knockout of the DNA target site cognate to the template.

12. The method of 10 wherein at least one of said HDR templates encodes an exogenous allele for replacement of an allele at the DNA target site cognate to the template.

13. The method of any of 1-12 wherein the cell or embryo is homozygous for a plurality of gene edits at the target DNA sites, said edits being encoded by HDR templates cognate to said target DNA sites.

14. The method of any of 1-12 wherein the cell or embryo is heterozygous for a plurality of gene edits at the target DNA sites said edits being encoded by HDR templates cognate to said target DNA sites.

15. The method of any of 11-14 wherein the gene edits comprise a knockout or an introgression of an allele from another breed of animal or another species of animal.

16. The method of any of 11-14 with the cell or embryo being a first species or a first breed of livestock, and a plurality of the edits comprise a replacement of a native allele with an exogenous allele from a second species or a second breed of animal.

17. The method of 16, with DNA sequences of the exogenous allele and the native allele differing at one or more positions, wherein replacement of the native allele with the exogenous allele makes a chromosomal DNA sequence of the cell or embryo identical to the second breed of animal or second species for a distance of at least 200 basepairs (bp) on each side of any of said positions, as measured by an alignment across said positions.

18. The method of 17 with the distance being a number between 200 and 2000 bp.

19. The method of any of 1-17 wherein the cell or embryo is homozygous for a plurality of gene edits at the target DNA sites, said edits being encoded by HDR templates cognate to said target DNA sites.

20. The method of any of 1-17 wherein the cell or embryo is heterozygous for a plurality of gene edits at the target DNA sites said edits being encoded by HDR templates cognate to said target DNA sites.

21. The method of any of 1-20 with the cell or embryo being selected from the group consisting of large vertebrate, livestock, simian, dog, cat, avian, bird, fish, rabbit, pig, cattle, buffalo, goat, sheep, and artiodactyl.

22. The method of any of 1-21 with the cell being selected from the group consisting of zygote, stem cell, adult stem cell, pluripotent cell, progenitor cell, and primary cell.

23. The method of any of 1-21 with the embryo being zygote, blastocyst, morula, or having a number of cells from 1-200.

24. The method of any of 1-23 comprising introducing mRNAs that encode one or more of the endonucleases and/or one or more of the HDR templates.

25. The method of any of 1-24 wherein one or more of the endonucleases are introduced into the cell or embryo as a protein.

26. The method of any of 1-25 wherein
of one or more (e.g., each of) of the endonucleases are provided as mRNAs and are introduced into the cell or embryo from a solution having a concentration from 0.1 ng/ml to 100 ng/ml; artisans will immediately appreciate that all values and ranges within the expressly stated limits are contemplated, e.g., about 20, from about 1 to about 20, from about 0.5 to about 50, and so forth; and/or
of one or more (e.g., each of) of the HDR templates are provided as mRNAs and are introduced into the cell or embryo from a solution having a concentration from about 0.2 µM to about 20 µM.

27. The method of any of 1-26 comprising electroporation for introduction of an endonuclease and/or HDR template.

28. The method of any of 1-27 wherein the endonuclease and/or HDR are introduced by a process selected from the group consisting of chemical-based methods, non-chemical methods, particle-based methods, and viral methods.

29. The method of any of 13-28 comprising introducing one or more vectors into the cell or embryo to express the endonucleases and/or the HDR templates.

30. The method of any of 1-29 wherein the targeted endonucleases are TALENs, or CRISPR, or a combination of TALENs and CRISPR.

31. The method of 30 wherein the edits are gene knockouts.

32. The method of any of 1-31 wherein one or more of the target site sequences are chosen from the following list, or wherein one or more of the exogenous alleles or the native alleles are chosen from the following list: IL2Rgy/–, RAG2–/–, IL2Rg$^{-/-}$; RAG2$^{-/-}$, IL2Rgy/–, RAG2–/–, IL2Rg+/–, RAG2+/–, IL2Rg$^{y/-}$; RAG2$^{+/-}$, IL2Rg$^{+/-}$; RAG2$^{+/-}$, DGAT (diglyceride acyltransferase), ABCG2 (ATP-binding cassette sub-family G member 2), ACAN (aggrecan), AMELY (amelogenin, y-linked), BLG (progestagen-associated endometrial protein), BMP 1B (FecB) (bone morphogenetic protein receptor, type 1B), DAZL (deleted in azoospermia like), Eif4GI (eukaryotic translation initiation factor 4 gamma, 1), GDF8 (growth/differentiation factor 8), Horn-poll locus, IGF2 (insulin-like growth factor 2), CWC15 (CWC15 spliceosome associated protein), KissR/GRP54 (kisspeptin), OFD1Y (Y-linked oral-facial-digital syndrome 1 pseudogene), p65 (v-rel reticuloendotheliosis viral oncogene homolog A), PRLR (prolactin receptor), Prmd14 (PR domain containtin 14), PRNP (prion protein), Rosa, Socs2 (suppressor of cytokine signaling 2), SRY (sex determining region of Chr Y), ZFY (zinc finger protein, y-linked), β-lactoglobulin, callipyg (CLPG), MODY 1 (HNF4α) (hepatocyte nuclear factor 4, alpha), MODY 2 (GCK) (glucokinase), MODY 3 (HNF1α) (hepatocyte nuclear factor 4, alpha), MODY 4 (Pdx1) (pancreatic and duodenal homeobox 1), MODY 5 (HNF-1β) (HNF1 homeobox B), MODY 6 (eurogenic differentiation 1), MODY 7 (KLF 11) (Kruppel-like factor 11), MODY 8 (CEL) (carboxyl ester lipase), MODY 9 (PAX4) (paired box 4), MODY 10 (INS) (insulin), MODY 11 (BLK) (BLK proto-oncogene, Src family tyrosine kinase), APC (adenomatosis polyposis coli), ApoE (apolipoprotein E), DMD (dystrophin muscular dystrophy), GHRHR (growth hormone releasing hormone receptor), HR (hair growth associated), HSD11B2 (hydroxysteroid (11-beta) dehydrogenase 2), LDLR (low density lipoprotein receptor), NF1 (neurofibromin 1), NPPA (natriuretic peptide A), NR3C2 (nuclear receptor subfamily 3, group C, member 2), p53 (cellular tumor antigen p53-like), PKD1 (polycystic kidney disase 1), Rbm20 (RNA binding motif protein 20), SCNN1G (sodium channel, non-voltage gated 1 gamma subunit), tP53 (tumor protein p53), FAH (fumarylacetoacetate hydrolase), HBB (hemoglobin beta), IL2RG (interleukin 2 receptor, gamma chain), PDX1 (pancreatic and duodenal homeobox 1), PITX3 (paired-like homeodomain transcription factor 3), Runx1 (runt-related transcription factor 1), GGTA (bifunctional cephalosporin acylase/gamma-glutamyltranspetidase), VASA (vasa protein), MIWI (piwi-like RNA-mediated gene silencing 1), PIWI (CG6122 gene product from transcript CG6122-RA), DCAF17 (DDB1 and CUL4 associated factor 17), VDR (vitamin D receptor), PNPLA1 (patatin-like phospholipase domain containing 1), HRAS (Harvey rat sarcoma viral oncogene homolog), Telomerasevert, DSP (desmoplakin), SNRPE (small nuclear ribonucleoprotein polypeptide E), RPL21 (ribosomal protein), LAMA3 (laminin, alpha 3), UROD (uroporphyrinogen decarboxylase), EDAR (ectodysplasin-A receptor), OFD1 (oral-facial-digital syndrome 1), PEX7 (peroxisomal biogenesis factor 7), COL3A1 (collagen, type III, alpha 1), ALOX12B (arachidonate 12olipoxygenase 12R type), HLCS (holocarboxylase synthetase (biotin-(proprionyl-CoA-carboxylase) ATP-hydrolysing)) ligase)), NIPAL4 (NIPA-like domain containing 4), CERS3 (ceramide synthase 3), ANTXR1 (anthrax toxin receptor 1), B3GALT6 (UDP-Gal:betaGAl beta 1,3 galactosyltransferase polypeptide 6), DSG4 (desmoglein 4), UBR1 (ubiquitin protein ligase E3 component n-recognin 1), CTC1 (CTS telomere maintenance complex component 1), MBTPS2 (membrane-bound transcription factor peptidase, site 2), UROS (uroporphyrinogen III synthase), ABHD5 (abhydrolase domain containing 5), NOP10 (NOP10 ribonucleoprotein), ALMS1 (Alstrom syndrome protein 1), LAMB3 (laminin, beta 3), EOGT (EGF domain-specific O-linked N-acetylglucosamine (GlcNAc)), SAT1 (spermindine/spermine N1-acetyltransferase 1), RBPJ (recombination signal binding protein for immunoglobulin kappa J region), ARHGAP31 (Rho GTPase activating protein 31), ACVR1 (activin A receptor, type I), IKBKG (inhibitor of kappa light polypeptide gene enhancer in B-cells, kinase gamma), LPAR6 (lysophosphatidic acid receptor 6), HR (hair growth associated), ATR (ATR serine/threonine kinase), HTRA1 (HtrA serine peptidase 1), AIRE (autoimmune regulator), BCS1L (BC1 (ubiquinol-cytochrome c reductase) synthesis-like), MCCC2 (methylcrotonoyl-CoA carboxylase 2 (beta)), DKC1 (dyskeratosis congenital 1, dyskerin), PORCN (porcupine homolog), EBP (emopamil binding protein (sterol isomerase)), SLITRK1 (SLIT and NTRK-like family, member 1), BTK (Bruton agammaglobulinemia tyrosine kinase), DOCK6 (dedicator of cytokinesis 6), APCDD1 (adenomatosis polyposis coli down-regulated 1), ZIP4 (zinc transporter 4 precursor), CASR (calcium-sensing receptor), TERT (telomerase reverse transcriptase), EDARADD (EDAR (ectodysplasin-A receptor)-associated death domain), ATP6VOA2 (ATPase, H+ transporting, lysosomal VO subunit a2), PVRL1 (poliovirus receptor-related 1 (herpesvirus entry mediator C)), MGP (matrix Gla protein), KRT85 (keratin 85, type II), RAG2 (recombination activating gene 2), RAG-1 (recombination activating gene 1), ROR2 (receptor tyrosine kinase-like orphan receptor 2), CLAUDINI (claudin 7), ABCA12 (ATP-binding cassette, subfamily A (ABC1), member 12), SLA-DRA1 (MHC class II DR-alpha), B4GALT7 (xylosylprotein beta 1,4-galactosyltransferase, polypeptide 7), COL7A1 (collagen type VII, alpha 1), NHP2 (NHP2 ribonucleoprotein), GNA11 (guanine nucleotide binding protein (g protein), alpha 11 (Gq class)), WNT5A (wingless-typ MMTV integration site family member 5A), USB1 (U6 snRNA biogenesis 1), LMNA (lamin A/C), EPS8L3 (EPS8-like 3), NSDHL (NAD(P) dependent steroid dehydrogenase-like), TRPV3 (transient receptor potential cation channel subfamily V, member 3), KRAS (Kirsten rat sarcoma viral oncogene homolog), TINF2 (TERF1-interacting nuclear factor 2), TGM1 (tranglutaminase 1), DCLREIC (DNA cross-link repair 1C), PKP1 (plakophilin 1), WRAP53 (WD repeat containing antisense to TP53), KDM5C (lysine (k) specific demethylase 5C), ECM1 (extracellular matrix protein 1), TP63 (tumor protein p63), KRT14 (keratin 14), RIPK4 (receptor-interacting serine-threonine kinase 4), PRKDC (protein kinase, DNA activated, catalytic polypeptide), BCL11a (B-cell CLL/lymphoma 11A (zinc finger protein)), BMI1 (BMI1 proto-oncogene, polycomb ring finger), CCR5 (chemokine (C—C motif) receptor 5 (gene/pseudogene)), CXCR4 (chemokine (C—X—C motif) receptor 4), DKK1 (dickkopf WNT signaling pathway inhibitor 1), ETV2 (ets variant 2), FLI1 (Fli-1 proto-oncogene, ETS transcription factor), FLK1 (kinase insert domain receptor), GATA2 (GATA binding protein 2), GATA4 (GATA binding protein 4), HHEX (hematopoietically expressed homeobox), KIT (kit oncogene), LMX1A (LIM homeobox transcription factor 1 alpha), MYF5 (myogenic factor 5), MYOD1 (myogenic differentiation 1), MYOG (myogenin), NKX2-5 (NK2 homeobox 5), NR4A2 (nuclear receptor subfamily 4, group A, member 2), PAX3 (paired box 3), PDX1 (pancreatic and duodenal homeobox 1), PITX3 (paired-like homeodomain transcription factor 3), Runx1 (runt-related transcription factor 1), RAG2 (recombination activating gene 2), GGTA (bifunctional cephalosporin acylase/gamma-glutamyhtranspeptidase), HANDII (heart-and neural crest derivative expressed protein 2), TBX5 (T-box 5), ETV2 (ets variant 2), PDX1 (pancreatic and duodenal homeobox 1), TBX4 (T-box 4), ID2 (inhibitor of DNA binding 2), SOX2 (SRY (sex determining region Y)-box 2), TTF1/NKX2-1 (NK2 homeobox 1), MESP1 (mesoderm posterior 1), NKX2-5 (HK2 homeobox 5), FAH (fumarylacetoacetate hydrolase), PRKDC (protein kinase, DNA activated, catalytic polypeptide), RUNX1 (runt related transcription factor 1), FLI1(fli-1 proto-oncogene, ETS transcription factor), PITX3 (paired-like homeodomain transcription factor 3), LMX1A (LIM homeobox transcription factor 1 alpha), DKK1 (dickkopf WNT signaling pathway inhibitor 1), NR4A2/NURR1 (nuclear receptor subfamily 4, group A, member 2), FLK1 (kinase insert domain receptor), HHEX1 (hematopoietically-expressed homeobox protein HHEX), BCL11A (B-cell CLL/lymphoma 11A (zinc finger protein), RAG2 (recombination activating gene 2), RAG1 (recombination activating gene 1), IL2RG (interleukin 2 receptor, gamma chain), c-KIT/SCFR (v-kit hardy-Zuckerman 4 feline sarcoma viral oncogene homolog), BMI1 (BMI1 proto-oncogene polycomb ring finger), TBX5 (T-box 5), OLIG1 (oligodendrocyte transcription factor 1), OLIG2 (oligodendrocyte transcription factor 2), heterozygotes thereof, homozygotes therefore, and combinations thereof.

33. A method of making multiplex gene knockouts in a primary vertebrate cell or embryo comprising introducing into the cell or embryo a plurality of TALENs targeted to different target genes in a presence of HDR templates with homology to said different target genes.

34. A method of making an animal comprising of any of 1-33 and further comprising cloning the cell or placing the embryo into a gestational mother.

35. An animal made by a method of any of 1-34.

36. A chimeric embryo or animal made by the method of any of 1-34 wherein the cell is edited and further comprising cloning the cell, making a host embryo from the cell, and adding a donor cell to the host embryo to form the chimeric embryo.

37. A vertebrate embryo chimeric for host cells and donor cells comprising a host embryo with a plurality of host cell genetic edits at different chromosomal DNA sites, and a donor cell integrated with the host cells to form the chimeric embryo.

38. A vertebrate deficiency carrier comprising an embryo with a plurality of multiplex genetic edits at different chromosomal DNA gene sites, the edits providing a genetic niche for complementation by donor cells.

39. The embryo or carrier of any of 37-38 wherein the donor cells are embryonic stem cells, pluripotent stem cells, blastomeres, and the like from primates, rodents, or artiodactyl.
40. The embryo of any of 37-39 wherein the host or carrier cell genetic edits comprise a knockout of a gene or a replacement of a native allele with an exogenous allele of another breed of vertebrate or another species of animal.
41. The embryo of any of 37-41 wherein a number of the host cell genetic edits is, or is at least, 2, 3, 4, 5, 6, or 7.
42. The embryo of any of 37-41 wherein a number of replacements of a native allele with an exogenous allele of another breed of vertebrate or another species of animal is, or is at least, 2, 3, 4, 5, 6, or 7.
43. The embryo of any of 37-42 wherein the embryo is free of expressible reporter genes and/or synthetic genes and/or exogenous fluorescent proteins.
44. The embryo of any of 37-43 wherein all of the gene edits are bi-allelic, at least 2, 3, 4, or 5 of the edits are bi-allelic, wherein at least 2, 3, 4, or 5 of the gene edits are monoallelic, or any combination thereof.
45. The embryo of any of 37-44 with the donor cell being a complement to the host cells.
46. The embryo of any of 37-45 wherein the host embryo is destined for a failure to thrive (FTT) phenotype.
47. The embryo of 46 wherein the donor cell rescues the embryo from the FTT phenotype.
48. The embryo of any of 37-47 wherein the donor cell comprises one or more genetic edits.
49. The embryo of any of 37-47 being selected from the group consisting of large vertebrate, livestock, simian, dog, cat, avian, bird, fish, rabbit, pig, cattle, buffalo, goat, sheep, and artiodactyl.
50. A vertebrate animal chimeric for host cells and donor cells comprising a plurality of host cell genetic edits at different chromosomal DNA sites, and a donor cell integrated with the host cells to form the chimeric animal.
51. The animal of 50 being selected from the group consisting of large vertebrate, livestock, simian, dog, cat, avian, bird, fish, rabbit, pig, cattle, buffalo, goat, sheep, and artiodactyl.
52. A method of making a vertebrate embryo chimeric for host cells and donor cells comprising:
   introducing into a host vertebrate cell:
   a first targeted endonuclease directed to a first target chromosomal DNA site and a first homology directed repair (HDR) template homologous to the first target site sequence; and
   a second targeted endonuclease directed to a second target chromosomal DNA site and a second HDR template homologous to the second target site sequence,
   with the first HDR template sequence replacing the native chromosomal DNA sequence at the first target site and the second HDR template sequence replacing the native chromosomal DNA sequence at the second target site sequence,
   cloning the cell to develop a host embryo, and placing a donor cell in the host embryo.
53. The method of 52 wherein the cell is a primary cell.
54. The method of any of 52-53 being selected from the group consisting of large vertebrate, livestock, simian, dog, cat, avian, bird, fish, rabbit, pig, cattle, buffalo, goat, sheep, and artiodactyl.
55. The method, cell, embryo, or animal of any of 1-54 being free of expressible reporter genes and/or synthetic genes and/or exogenous fluorescent proteins.
56. A chimeric large vertebrate animal comprising host cells and donor cells, with the host cells comprising at least one non-meiotic gene edit to a gametogenic or spermatogenic gene that is complemented by a gene of the donor cells, with the animal comprising gametes with a genotype of the donor cells.
57. The animal of 56 being free of functional gametes with a genotype of the host cells.
58. A chimeric large vertebrate animal comprising host cells and donor cells, with the host cells comprising at least one non-meiotic gene edit to establish a failure to thrive (FTT) host cell genotype, with the FTT genotype being complemented by the donor cells.
59. The animal of 58 wherein the host cells comprise a plurality of non-meiotic gene edits that establish a failure to thrive (FTT) host cell genotype.
60. The animal of any of 58 or 59 wherein the FTT phenotype is immunodeficiency.
61. A large vertebrate animal comprising multiplex gene edits.
62. The animal of 61 being a first breed of pig or a first breed of cattle that has at least three native alleles replaced with corresponding exogenous alleles of a second breed or another species, said exogenous alleles being a replacement of the corresponding native allele without meiotic recombination, wherein the animal is free of exogenous marker genes.
63. The animal of 61 or 62 comprising at least three, four, five, six, or seven of said exogenous replacement alleles, each without meiotic recombination.
64. The animal of any of 61-63 being selected from the group consisting of livestock, simian, dog, cat, avian, bird, fish, rabbit, pig, cattle, buffalo, goat, sheep, and artiodactyl.
65. The animal any of 61-64 having a number of edits from 3 to 25.
66. The animal of any of 61-65 being an F0 generation with respect to the multiplex edits.
67. The animal of any of 61-66 having a number of allele replacements from 2-25.
68. The animal of any of 61-67 having a number of KO gene edits from 2-25.
69. The animal of 61 being a first breed of pig or a first breed of cattle that has at least three native alleles replaced with corresponding exogenous alleles of a second breed or another species, said exogenous alleles being a replacement of the corresponding native allele without meiotic recombination, wherein the animal is free of exogenous marker genes.
70. The animal of 69 comprising at least three, four, five, six, or seven of said exogenous replacement alleles, each without meiotic recombination.

What is claimed is:

1. A method of making gene edits in vitro in a non-human vertebrate cell at two or more gene loci, the method comprising a simultaneous step of introducing into a non-human vertebrate cell:
   a first targeted CRISPR endonuclease system directed to a first target chromosomal DNA site in a genome of the non-human vertebrate cell,
   a first homology directed repair template homologous to a single gene locus in the first target chromosomal DNA site,
   a second targeted CRISPR endonuclease system directed to a second target chromosomal DNA site in the genome of the non-human vertebrate cell, and
   a second homology directed repair template homologous to a single gene locus in the second target chromosomal DNA site,
      wherein the first homology directed repair template sequence independently replaces a native chromosomal DNA sequence at the single gene locus in the first target chromosomal DNA site in the genome of the non-human vertebrate cell and the second homology directed repair template sequence independently replaces a native chromosomal DNA sequence at the single gene locus in the second target chromosomal DNA site in the genome of the non-human vertebrate cell;
   wherein the first target chromosomal DNA site is in a first gene and the second target chromosomal DNA site is in a second gene;
   thereby making a non-human vertebrate cell comprising gene edits at two or more gene loci.

2. The method of claim 1 further comprising introducing into the non-human vertebrate cell one or more of:
   a third, fourth, fifth, sixth, or seventh targeted CRISPR endonuclease system directed to a third, fourth, fifth, sixth, or seventh target chromosomal DNA site, respectively, and a third, fourth, fifth, sixth, or seventh homology directed repair template homologous to a single gene locus in each of the third, fourth, fifth, sixth, or seventh target chromosomal DNA sites, respectively.

3. The method of claim 1, wherein the first targeted CRISPR endonuclease system comprises a Cas9.

4. The method of claim 1, wherein at least one of the first homology directed repair template or the second homology directed repair template encodes a knockout of a DNA target site cognate to the first homology directed repair template or the second homology directed repair template, respectively, or wherein the first homology directed repair template or the second homology directed repair template encodes an exogenous allele for replacement of an allele at the DNA target site cognate to the first homology directed repair template or the second homology directed repair template, respectively.

5. The method of claim 1, wherein the non-human vertebrate cell is from a first species or a first breed of livestock, and the gene edits comprise a replacement of a native allele with an exogenous allele from a second species or a second breed of livestock.

6. The method of claim 1, wherein (i) the non-human vertebrate cell is homozygous or heterozygous for a first gene edit of the gene edits at the first target chromosomal DNA site, the first gene edit being encoded by the first homology directed repair template, or (ii) the non-human vertebrate cell is homozygous or heterozygous for a second gene edit of the gene edits at the second target chromosomal DNA site, the second gene edit being encoded by the second homology directed repair template.

7. The method of claim 1, wherein the non-human vertebrate cell is a cell from a non-human vertebrate selected from the group consisting of simian, dog, cat, bird, fish, rabbit, pig, cattle, buffalo, goat, sheep, and artiodactyl.

8. The method of claim 1, wherein the non-human vertebrate cell is selected from the group consisting of zygote, stem cell, adult stem cell, pluripotent cell, progenitor cell, and primary cell.

9. The method of claim 1, wherein the single gene locus in the first target Interleukin Receptor 2 gamma (IL2RG).

10. The method of claim 1, wherein the gene edits comprise one or more selected from the group consisting of an insertion, a deletion, a substitution, and a combination thereof.

11. The method of claim 10, wherein the gene edits comprise more than one insertion or more than one deletion, or a combination thereof.

12. The method of claim 1, wherein at least one gene edit of the gene edits prevents expression of a functional factor encoded by the first gene and comprises an insertion, deletion, or substitution of one or more bases in a sequence encoded by the first gene and/or a promoter and/or an operator that is necessary for expression of the first gene in the non-human vertebrate cell.

13. The method of claim 1, wherein at least one gene edit of the gene edits disrupts the first gene, and the disruption occurs by removal of at least a portion of the first gene or alteration of the first gene to prevent expression of a functional factor encoded by the first gene.

* * * * *

SEQUENCE LISTING

<160> NUMBER OF SEQ ID NOS: 38

<210> SEQ ID NO 1
<211> LENGTH: 90
<212> TYPE: DNA

```
<213> ORGANISM: Artificial Sequence
<220> FEATURE:
<223> OTHER INFORMATION: Synthetic Homology Directed Repair Template

<400> SEQUENCE: 1
ctcttttcgc aggcacaggt ctacgagctg gagcgacgct tctaagcttg cagcagcggt    60
acctgtcggc tcccgagcgt gaccagttgg                                    90

<210> SEQ ID NO 2
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 2
aaccctgtgt cgtttcccac ccagtagata tgtttgatga ctaagcttct cggaaggcag    60
agagtgtgtc aactgcgggg ccatgtccac                                    90

<210> SEQ ID NO 3
<211> LENGTH: 60
<212> TYPE: DNA
<213> ORGANISM: Artificial Sequence
<220> FEATURE:
<223> OTHER INFORMATION: Synthetic Homology Directed Repair Template

<400> SEQUENCE: 3
tgcggttgct cccccgcctc gtccccgtaa gcttgactcc tggtgcagcg ccccggccag    60

<210> SEQ ID NO 4
<211> LENGTH: 36
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 4

His Asp His Asp His Asp Asn Ile Asn Ile Asn Asn Asn Asn
1               5                   10                  15

Asn Gly Asn Gly His Asp Asn Ile Asn Asn Asn Gly Asn Asn Asn Gly
            20                  25                  30

Asn Gly Asn Gly
        35

<210> SEQ ID NO 5
<211> LENGTH: 40
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 5

His Asp His Asp Asn Ile Asn Ile Asn Asn Asn Gly Asn Asn His Asp
1               5                   10                  15

Asn Ile Asn Ile Asn Gly Asn Gly His Asp Asn Ile Asn Gly Asn Asn
            20                  25                  30

Asn Gly Asn Ile His Asp Asn Gly
        35                  40

<210> SEQ ID NO 6
<211> LENGTH: 36
<212> TYPE: PRT
<213> ORGANISM: Artificial Sequence
```

<220> FEATURE:
<223> OTHER INFORMATION: Synthetic Repeat-Variable Diresidue (RVD) Code

<400> SEQUENCE: 6

Asn Ile His Asp His Asp Asn Gly Asn Gly His Asp His Asp Asn Gly
1               5                   10                  15

His Asp His Asp Asn Gly His Asp Asn Gly His Asp His Asp Asn Asn
            20                  25                  30

His Asp Asn Gly
        35

<210> SEQ ID NO 7
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 7

His Asp Asn Gly Asn Ile Asn Ile Asn Asn His Asp Asn Gly Asn Asn
1               5                   10                  15

His Asp Asn Gly Asn Gly Asn Gly Asn Gly Asn Asn Asn Ile Asn Ile
            20                  25                  30

Asn Gly

<210> SEQ ID NO 8
<211> LENGTH: 36
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 8

Asn Asn Asn Asn Asn Ile Asn Ile Asn Asn Asn Ile Asn Ile Asn Asn
1               5                   10                  15

Asn Gly Asn Ile Asn Gly His Asp Asn Ile Asn Asn His Asp His Asp
            20                  25                  30

Asn Ile Asn Gly
        35

<210> SEQ ID NO 9
<211> LENGTH: 32
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 9

Asn Asn Asn Ile His Asp His Asp His Asp Asn Ile Asn Asn Asn Ile
1               5                   10                  15

Asn Ile Asn Gly Asn Gly Asn Gly His Asp Asn Gly Asn Asn Asn Gly
            20                  25                  30

<210> SEQ ID NO 10
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 10

Asn Asn Asn Asn His Asp Asn Ile His Asp His Asp His Asp Asn Asn
1               5                   10                  15

Asn Gly Asn Asn Asn Gly His Asp His Asp Asn Asn His Asp Asn Asn
            20                  25                  30

His Asp

<210> SEQ ID NO 11
<211> LENGTH: 30
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 11

His Asp Asn Ile Asn Gly Asn Asn Gly Asn Ile His Asp Asn Gly
1               5                   10                  15

His Asp Asn Gly Asn Asn Asn Ile His Asp Asn Gly Asn Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 12

Asn Asn His Asp Asn Gly His Asp Asn Gly Asn Ile His Asp Asn Gly
1               5                   10                  15

His Asp Asn Gly Asn Ile His Asp His Asp His Asp His Asp
            20                  25                  30

<210> SEQ ID NO 13
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 13

Asn Asn His Asp Asn Ile His Asp Asn Ile Asn Gly Asn Asn Asn Ile
1               5                   10                  15

Asn Ile Asn Asn Asn Gly His Asp Asn Asn His Asp His Asp His Asp
            20                  25                  30

Asn Ile

<210> SEQ ID NO 14
<211> LENGTH: 36
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 14

His Asp His Asp Asn Asn Asn Gly His Asp His Asp Asn Gly Asn Gly
1               5                   10                  15

Asn Gly Asn Asn His Asp His Asp Asn Ile Asn Ile His Asp His Asp
            20                  25                  30

Asn Gly Asn Gly
        35

<210> SEQ ID NO 15
<211> LENGTH: 36
<212> TYPE: PRT

```
<213> ORGANISM: Artificial Sequence
<220> FEATURE:
<223> OTHER INFORMATION: Synthetic Repeat-Variable Diresidue (RVD) Code

<400> SEQUENCE: 15

Asn Gly Asn Asn Asn Asn Asn Asn Asn Asn Asn His Asp His Asp
1               5                   10                  15

His Asp Asn Ile His Asp Asn Asn Asn Gly Asn Gly Asn Asn
                20                  25                  30

His Asp Asn Gly
        35

<210> SEQ ID NO 16
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 16

His Asp Asn Gly His Asp His Asp Asn Gly Asn Ile His Asp Asn Ile
1               5                   10                  15

Asn Ile Asn Asn Asn Gly Asn Asn Asn Asn Ile Asn Gly Asn Gly
            20                  25                  30

Asn Gly

<210> SEQ ID NO 17
<211> LENGTH: 36
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 17

His Asp Asn Asn Asn Asn Asn Ile His Asp His Asp His Asp Asn Asn
1               5                   10                  15

Asn Gly His Asp His Asp Asn Gly Asn Gly Asn Asn His Asp Asn Ile
            20                  25                  30

His Asp Asn Gly
        35

<210> SEQ ID NO 18
<211> LENGTH: 30
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 18

Asn Asn Asn Asn Asn Ile His Asp Asn Gly Asn Asn Asn Ile His Asp
1               5                   10                  15

His Asp Asn Ile His Asp Asn Gly Asn Ile Asn Gly Asn Gly
            20                  25                  30

<210> SEQ ID NO 19
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 19

Asn Ile Asn Asn Asn Ile Asn Asn Asn Ile Asn Ile Asn Gly Asn Asn
```

```
                1               5                  10                  15
Asn Gly Asn Asn Asn Asn Asn Gly His Asp His Asp Asn Ile Asn Asn
                20                  25                  30

His Asp

<210> SEQ ID NO 20
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 20

His Asp Asn Asn His Asp Asn Ile Asn Asn Asn Asn His Asp Asn Ile
1               5                  10                  15

His Asp Asn Ile Asn Asn Asn Asn Asn Gly His Asp Asn Gly Asn Ile
                20                  25                  30

His Asp

<210> SEQ ID NO 21
<211> LENGTH: 30
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 21

Asn Ile His Asp His Asp Asn Asn His Asp Asn Gly Asn Asn His Asp
1               5                  10                  15

Asn Gly Asn Asn His Asp Asn Gly Asn Gly Asn Asn Asn Ile
                20                  25                  30

<210> SEQ ID NO 22
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 22

Asn Asn His Asp Asn Asn Asn Asn Gly Asn Gly Asn Asn His Asp
1               5                  10                  15

Asn Gly His Asp His Asp His Asp His Asp His Asp Asn Asn His Asp
                20                  25                  30

His Asp

<210> SEQ ID NO 23
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 23

Asn Asn Asn Asn His Asp His Asp Asn Asn Asn Asn Asn Asn Asn Asn
1               5                  10                  15

His Asp Asn Asn His Asp Asn Gly Asn Asn His Asp Asn Ile His Asp
                20                  25                  30

His Asp

<210> SEQ ID NO 24
```

```
<211> LENGTH: 30
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 24

Asn Ile Asn Gly Asn Asn Asn Gly Asn Gly Asn Gly Asn Asn Asn Ile
1               5                   10                  15

Asn Gly Asn Asn Asn Ile His Asp Asn Gly Asn Gly His Asp
            20                  25                  30

<210> SEQ ID NO 25
<211> LENGTH: 34
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 25

Asn Asn Asn Asn His Asp His Asp His Asp His Asp Asn Asn His Asp
1               5                   10                  15

Asn Ile Asn Asn Asn Gly Asn Gly Asn Asn Asn Ile His Asp Asn Ile
            20                  25                  30

His Asp

<210> SEQ ID NO 26
<211> LENGTH: 23
<212> TYPE: PRT
<213> ORGANISM: Artificial Sequence
<220> FEATURE:
<223> OTHER INFORMATION: Synthetic Repeat-Variable Diresidue (RVD) Code

<400> SEQUENCE: 26

Cys Gly Thr Cys Ala Cys Cys Ala Ala Cys Gly Gly Thr Cys Thr Cys
1               5                   10                  15

Cys Thr Cys Thr Cys Gly Gly
            20

<210> SEQ ID NO 27
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 27
ttccactcta cccccccaa aggttcagtg ttttgtgtaa gcttcaatgt tgagtacatg      60
aattgcactt gggacagcag ctctgagctc                                     90

<210> SEQ ID NO 28
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 28
ctctaaggat tcctgccacc ttcctcctct ccgctaccca gactaagctt tgcacattca    60
aaagcagctt agggtctgaa aacatcagt                                      90

<210> SEQ ID NO 29
<211> LENGTH: 90
```

```
<212> TYPE: DNA
<213> ORGANISM: Artificial Sequence
<220> FEATURE:
<223> OTHER INFORMATION: Synthetic Homology Directed Repair Template

<400> SEQUENCE: 29
ccagatcgcc aaagtcacgg aagaagtatc agccattcat ccctcccagt gaagcttaca      60
gaaattctgg gtcgaccacg gagttgcact                                      90

<210> SEQ ID NO 30
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 30
agctcgccac ccccgccggg cacccgtgtc cgcgccatgg ccatctaagc ttaaagaagt      60
cagagtacat gcccgaggtg gtgaggcgct                                      90

<210> SEQ ID NO 31
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 31
gtgctgcgtg ccctttactg ctctactcta cccctacca gcctaagctt gtgctgggcg       60
acttcatgtg caagttcctc aactacatcc                                      90

<210> SEQ ID NO 32
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 32
cccagacttc actccgtcct ttgccgactt cggccgacca gcccttagca accgtgggcc      60
cccaaggggt gggccaggtg gggagctgcc                                      90

<210> SEQ ID NO 33
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 33
ccgagacggg aaatgcacct cctacaagtg gatttgtgat ggatccgaac accgagtgca      60
aggacgggtc cgctgagtcc ctggagacgt                                      90

<210> SEQ ID NO 34
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 34
aaagtggcct ggcccaaccc ctggactgac cactcgagta ttgaagcacg taagtatgct      60
```

```
ggaccacatt ctctatggct gtagacattc                                      90

<210> SEQ ID NO 35
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 35
ctcttttcgc aggcacaggt ctacgagctg gagcgacgct tctaagcttg cagcagcggt     60
acctgtcggc tcccgagcgt gaccagttgg                                     90

<210> SEQ ID NO 36
<211> LENGTH: 60
<212> TYPE: DNA
<213> ORGANISM: Artificial Sequence
<220> FEATURE:
<223> OTHER INFORMATION: Synthetic Homology Directed Repair Template

<400> SEQUENCE: 36
tgcggttgct cccccgcctc gtcccgtaa gcttgactcc tggtgcagcg ccccggccag      60

<210> SEQ ID NO 37
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 37
aaccctgtgt cgtttcccac ccagtagata tgtttgatga ctaagcttct cggaaggcag     60
agagtgtgtc aactgcgggg ccatgtccac                                     90

<210> SEQ ID NO 38
<211> LENGTH: 90
<212> TYPE: DNA
<213> ORGANISM: Artificial Sequence
<220> FEATURE:
<223> OTHER INFORMATION: Synthetic Homology Directed Repair Template

<400> SEQUENCE: 38
gctcccactc ccctgggggc ctctgggctc accaacggtc tcctcccggg ggacgaagac     60
ttctcctcca ttgcggacat ggacttctca                                     90
```